US008949084B2

(12) United States Patent
Baym et al.

(10) Patent No.: US 8,949,084 B2
(45) Date of Patent: *Feb. 3, 2015

(54) DETERMINING A NEXT VALUE OF A SYSTEM-SIMULATION PARAMETER IN RESPONSE TO A REPRESENTATION OF A PLOT HAVING THE PARAMETER AS A DIMENSION

(75) Inventors: Michael H. Baym, Cambridge, MA (US); Philip Andrew Eckhoff, Bellevue, WA (US); Daniel Jay MacDonald, Seattle, WA (US); Nathan P. Myhrvold, Bellevue, WA (US); Karima R. Nigmatulina, Bellevue, WA (US); Charles Whitmer, North Bend, WA (US); Lowell L. Wood, Jr., Bellevue, WA (US)

(73) Assignee: Tokitae LLC, Bellevue, WA (US)

( * ) Notice: Subject to any disclaimer, the term of this patent is extended or adjusted under 35 U.S.C. 154(b) by 134 days.

This patent is subject to a terminal disclaimer.

(21) Appl. No.: 13/199,044

(22) Filed: Aug. 16, 2011

(65) Prior Publication Data
US 2013/0046517 A1 Feb. 21, 2013

(51) Int. Cl.
G06F 17/50 (2006.01)
G06F 17/10 (2006.01)
G06F 17/17 (2006.01)
G06F 19/00 (2011.01)

(52) U.S. Cl.
CPC .......... G06F 17/5009 (2013.01); G06F 17/175 (2013.01); G06F 2217/10 (2013.01); G06F 19/3437 (2013.01)
USPC .................................................. 703/2; 703/6

(58) Field of Classification Search
None
See application file for complete search history.

(56) References Cited

U.S. PATENT DOCUMENTS

| 2003/0233197 | A1 | 12/2003 | Padilla et al. |
| 2004/0088406 | A1 | 5/2004 | Corley et al. |
| 2008/0172214 | A1 | 7/2008 | Col et al. |
| 2009/0055150 | A1 | 2/2009 | Prior et al. |
| 2009/0112541 | A1 | 4/2009 | Anderson et al. |
| 2010/0010788 | A1* | 1/2010 | De Crecy .......................... 703/2 |
| 2010/0125241 | A1 | 5/2010 | Prud'homme et al. |
| 2010/0138160 | A1 | 6/2010 | Jacquez et al. |
| 2011/0307438 | A1* | 12/2011 | Fernandez Martinez ....... 706/52 |
| 2013/0046516 | A1* | 2/2013 | Baym et al. ....................... 703/2 |
| 2013/0046517 | A1* | 2/2013 | Baym et al. ....................... 703/2 |

OTHER PUBLICATIONS

Smith, T., et al. "Towards a Comprehensive Simulation Model of Malaria Epidemiology and Control" Parasitology, vol. 135, pp. 1507-1516 (2008) available from doi:10.1017/S0031182008000371.*

(Continued)

Primary Examiner — Kamini S Shah
Assistant Examiner — Jay B Hann
(74) Attorney, Agent, or Firm — Lane Powell PC; Bryan A. Santarelli

(57) ABSTRACT

An embodiment of an apparatus includes a simulator, generator, and determiner. The simulator is configured to simulate a system and to propagate at least one state of the simulated system through time in response to a value of a parameter, and the generator is configured to generate a representation of a region of a plot having dimensions that respectively correspond at least to the parameter and to a characteristic of a state of the simulated system. And the determiner is configured to determine a next value of the parameter in response to the representation of the region.

68 Claims, 16 Drawing Sheets

(56) References Cited

OTHER PUBLICATIONS

Gemperli, A., et al. "Malaria Mapping Using Transmission Models: Application to Survey Data from Mali" Am. J. Epidemiology, vol. 163, No. 3, pp. 289-296 (2005).*
Synonyms of "region" from Thesaurus.com (accessed 2013).*
Definition of "plot" from dictionary.reference.com (accessed 2013).*
Definition of "plot" from mathworld.wolfram.com/Plot.html (accessed 2013).*
Definition of "distribution" from dictionary.reference.com (accessed 2013).*
PCT International Search Report; International App.: PCT/US12/00359; Nov. 5, 2012; pp. 1-2.
PCT Written Opinion of the International Searching Authority; International App.: PCT/US12/00359; Nov. 5, 2012; pp. 1-20.
Philip Eckhoff, "A Malaria Eradication-Directed Model of Mosquito Life Cycle and Ecology", Intellectual Ventures, LLC, PMB 502, 227 Bellevue Way, Bellevue WA 98004-5721, pp. 28.
Philip Eckhoff, "A Model of *P. falciparum* Infection With Innate and Adaptive Host Immunity",, Intellectual Ventures, LLC, PMB 502, 227 Bellevue Way, Bellevue WA 98004-5721, pp. 41.
Philip Eckhoff, William H. Gates, Nathan Myhrvold, Lowell Wood, "Computer-Based Modeling in Support of Global Eradication of Infectious Disease: Principles and Practice", Intellectual Ventures, LLC, PMB 502, 227 Bellevue Way, Bellevue WA 98004-5721, pp. 25.
Nicole Cancré Adama Tall, Christophe Rogier, Joseph Faye, Ousmane Sarr, Jean-François Trape, André Spiegel, and Frédéric Bois "Bayesian Analysis of an Epidemiologic Model of Plasmodium Falciparum Malaria Infection in Ndiop, Senegal", American Journal of Epidemiology, vol. 152, No. 8, pp. 760-770.
Thomas Smith, Gerry F. Killeen, Nicolas Maire, Amanda Ross, Louis Molineaux, Fabrizio Tediosi, Guy Hutton, Jam Utzinger, Klaus Dietz, and Marcel Tanner, "Mathematical Modeling of the Impact of Malaria Vaccines on the Clinical Epidemiology and Natural History of Plasmodium Falciparum Malaria: Overview", Am. J. Trop. Med. Hyg., 75(Suppl 2), 2006, pp. 1-10.
Abramson, I.S.; "On Bandwidth Variation in Kernel Estimates—A Square Root Law"; The Annals of Statistics; Bearing dates of Oct. 1981, Mar. 1982 and 1982; pp. 1217-1223; vol. 10, No. 4.
Altman, N.S.; "An Introduction to Kernel and Nearest-Neighbor Nonparametric Regression"; The American Statistician; Bearing a date of Aug. 1992; pp. 175-185; vol. 46, No. 3; American Statistical Association.
Altman et al.; "Bandwidth Selection for Kernel Distribution Function Estimation"; Journal of Statistical Planning and Inference; Bearing dates of Oct. 5, 1993, Aug. 15, 1994 and 1995; pp. 195-214; vol. 46; Elsevier Science B.V.
Altman et al.; "Consistent Bandwidth Selection for Kernel Binary Regression"; Journal of Statistical Planning and Inference; Bearing dates of Aug. 3, 1995, Oct. 20, 1997 and 1998; pp. 121-137; vol. 70; Elsevier Science B.V.
Ankenman et al.; "Stochastic Kriging for Simulation Metamodeling"; Proceedings of the 2008 Winter Simulation Conference; Bearing a date of 2008; pp. 362-370; IEEE.
Baesler et al.; "Multi-Response Simulation Optimization Using Stochastic Genetic Search Within a Goal Programming Framework"; Proceedings of the 2000 Winter Simulation Conference; Bearing a date of 2000; pp. 788-794.
Baesler et al.; "Multi-Objective Simulation Optimization for a Cancer Treatment Center"; Proceedings of the 2001Winter Simulation Conference; Bearing a date of 2001; pp. 1405-1411.
Barton et al. "Chapter 18—Metamodel-Based Simulation Optimization"; Handbook in OR & MS; Bearing a date of 2006; pp. 535-574; vol. 13; Elsevier B.V.
Barton, R.R.; "Simulation Metamodels"; Proceedings of the 1998 Winter Simulation Conference; Bearing a date of 1998; pp. 167-174.
Bernardo, et al.; Bayesian Theory-Table of Contents; Bearing a date of 2000; 12 Total Pages; vol. 62; John Wiley & Sons, Ltd.
Bernardo, J.M.; "Expected Information as Expected Utility"; The Annals of Statistics; Bearing dates of Aug. 1976, Oct. 1977 and 1979; pp. 686-690; vol. 7, No. 3.
Besag, J.E.; "Nearest-Neighbour Systems and the Auto-Logistic Model for Binary Data"; Journal of the Royal Statistical Society. Series B (Methodological); Bearing dates of Feb. 1971, Sep. 1971 and 1972; pp. 75-83; vol. 34, No. 1; Royal Statistical Society.
Blanning, R.W.; "The Construction and Implementation of Metamodels"; Simulation; Bearing a date of Jun. 1975; pp. 177-184; vol. 24; Simulation Councils, Inc.
Blower et al.; "Sensitivity and Uncertainty Analysis of Complex Models of Disease Transmission: An HIV Model, as an Example"; International Statistical Review; Bearing a date of 1994; pp. 229-243; vol. 62, No. 2; International Statistical Institute.
Box et al.; "On the Experimental Attainment of Optimum Conditions" Journal of the Royal Statistical Society. Series B (Methodological); Bearing dates of Nov. 29, 1950 and 1951; pp. 1-45; vol. 13, No. 1.
Breman et al. "Conquering the Intolerable Burden of Malaria: What's New, What's Needed: A Summary"; Am. J. Trop. Med. Hyg.; Bearing a date of 2004; pp. 1-15; vol. 71, Suppl. 2; The American Society of Tropical Medicine and Hygiene.
Carson et al. "Simulation Optimization: Methods and Applications"; Proceedings of the 1997 Winter Simulation Conference; Bearing a date of 1997; pp. 118-126.
Castiglione et al. "Optimization of HAART with Genetic Algorithms and Agent-Based Models of HIV Infection"; Bioinformatics, Bearing dates of May 3, 2007, Aug. 7, 2007 and 2007; pp. 3350-3355; vol. 23, No. 24; Oxford University Press.
Chaloner et al.; "Bayesian Experimental Design: A Review"; Statistical Science; Bearing a date of 1995; pp. 273-304; vol. 10, No. 3.
Chick, S.E.; "Bayesian Ideas and Discrete Event Simulation: Why, What and How"; Proceedings of the 2006 Winter Simulation Conference; Bearing a date of 2006; pp. 96-106; IEEE.
Chick, S.E.; "Bayesian Methods for Discrete Event Simulation"; Proceedings of the 2004 Winter Simulation Conference; Bearing a date of 2004; pp. 89-100.
Chick et al.; "Joint Criterion for Factor Identification and Parameter Estimation"; Proceedings of the 2002 Winter Simulation Conference; Bearing a date of 2002; pp. 400-406.
Dancik et al.; "Parameter Estimation and Sensitivity Analysis in an Agent-Based Model of *Leishmania Major* Infection"; J. Theor. Biol.; Bearing a date of Feb. 7, 2010; pp. 398-412; vol. 262, No. 3.
Degroot, M.H.; Optimal Statistical Decisions Table of Contents; Bearing dates of 1970 and 2004; 17 Total Pages; Wiley-Interscience.
Donohue, J.M.; "Experimental Designs for Simulation"; Proceedings of the 1994 Winter Simulation Conference; Bearing a date of 1994; pp. 200-206.
Duintjer Tebbens et al.; "Uncertainty and Sensitivity Analyses of a Decision Analytic Model for Posteradication Polio Risk Management"; Risk Analysis; Bearing a date of 2008; pp. 855-876; vol. 28, No. 4; Society for Risk Analysis.
Duintjer Tebbens et al.; "Uncertainty and Sensitivity Analyses of a Dynamic Economic Evaluation Model for Vaccination Programs"; Medical Decision Making; Bearing a date of Mar.-Apr. 2008; pp. 182-200; vol. 28.
Ellis et al.; "Parameterization and Sensitivity Analysis of a Complex Simulation Model for Mosquito Population Dynamics, Dengue Transmission, and their Control"; Am. J. Trop. Med. Hyg.; Bearing a date of 2011; pp. 257-264; vol. 85, No. 2; The American Society of Tropical Medicine and Hygiene.
Fang et al.; "Global Response Approximation with Radial Basis Functions"; Engineering Optimization; Bearing a date of Jun. 2006; pp. 407-424; vol. 38, No. 4; Taylor & Francis.
Ferguson et al.; "Planning for Smallpox Outbreaks"; Nature; Bearing a date of Oct. 16, 2003; pp. 681-685; vol. 425; Nature Publishing Group.
Fillinger et al.; "Integrated Malaria Vector Control with Microbial Larvicides and Insecticide-Treated Nets in Western Kenya: A Controlled trial"; Bull World Health Organ; Bearing dates of Jun. 9, 2008, Oct. 31, 2008, Nov. 25, 2008, Jul. 7, 2009 and 2009; pp. 655-665; vol. 87.

(56) References Cited

OTHER PUBLICATIONS

Fraser et al.; "Pandemic Potential of a Strain of Influenza a (H1N1): Early Findings"; Science, Bearing a date of Jun. 19, 2009; pp. 1557-1561; vol. 324.
Fu, M.C.; "Optimization for Simulation: Theory vs. Practice"; INFORMS Journal on Computing; Bearing a date of Summer 2002; pp. 192-215; vol. 14, No. 3.
Fu, M.C.; "Optimization via Simulation: A Review"; Annals of Operations Research; Bearing dates of Nov. 1992, Apr. 1993 and 1994; pp. 199-248; vol. 53.
Fu, M.C.; "Simulation Optimization: A Review, New Developments, and Applications"; Proceedings of the 2005 Winter Simulation Conference; Bearing a date of 2005; 14 Total Pages.
Ghosh, A.K.; "On Optimum Choice of $k$ in Nearest Neighbor Classification"; Computational Statistics & Data Analysis; Bearing dates of Oct. 20, 2004, Mar. 7, 2005, Jun. 17, 2005, Jul. 19, 2005 and 2006; pp. 3113-3123; vol. 50; Elsevier B.V.
Gimnig et al.; "Effect of Permethrin-Treated Bed Nets on the Spatial Distribution of Malaria Vectors in Western Kenya"; Am. J. Trop. Med. Hyg.; Bearing a date of 2003; pp. 115-120; vol. 68, Suppl 4; The American Society of Tropical Medicine and Hygiene.
Gimnig et al.; "Impact of Permethrin-Treated Bed Nets on Entomologic Indices in an Area of Intense Year-Round Malaria Transmission"; Am. J. Trop. Med. Hyg.; Bearing a date of 2003; pp. 16-22; vol. 68, Suppl 4; The American Society of Tropical Medicine and Hygiene.
Grassly et al.; "New Strategies for the Elimination of Polio From India"; Science; Bearing a date of Nov. 17, 2006; pp. 1150-1153; vol. 314, printed on Feb. 17, 2012.
Griffith, D.A.; "A Spatial Filtering Specification for the Autologistic Model"; Environment and Planning A; Bearing dates of Oct. 8, 2003, Dec. 31, 2003 and 2004; pp. 1791-1811 (1 Total Page); vol. 36, No. 10 (Abstract Only).
Hachicha et al.; "A Comprehensive Literature Classification of Simulation Optimisation Methods"; MPRA Paper; Bearing dates of May 24-26, 2010; pp. 1-13.
Hall et al.; "A Geometrical Method for Removing Edge Effects From Kernel-Type Nonparametric Regression Estimators"; Journal of the American Statistical Association; Bearing a date of Sep. 1991; pp. 665-672; vol. 86, No. 415.
Hall et al.; "Nonparametric Kernel Regression Subject to Monotonicity Constraints"; The Annals of Statistics; Bearing dates of Mar. 1999, Dec. 2000 and 2001; pp. 624-647; vol. 29, No. 3.
Harp et al.; "An Agent-Based Approach to Global Uncertainty and Sensitivity Analysis"; Computers & Geosciences; Bearing dates of Feb. 2, 2011, May 6, 2011, Jun. 29, 2011, Jul. 28, 2011 and 2012; pp. 19-27; vol. 40; Elsevier Ltd.
Hazelton, M.L.; "Bias Reduction in Kernel Binary Regression"; Computational Statistics & Data Analysis; Bearing dates of Apr. 10, 2006, Jun. 13, 2006, Jun. 18, 2006, Jul. 28, 2006 and 2007; pp. 4393-4402; vol. 51; Elsevier B.V.
Hearne, J.W.; "An Automated Method for Extending Sensitivity Analysis to Model Functions"; Natural Resource Modeling; Bearing a date of May 2010; pp. 107120; vol. 23, No. 2; Wiley Periodicals, Inc.
Helton et al.; "A Comparison of Uncertainty and Sensitivity Analysis Results Obtained with Random and Latin Hypercube Sampling"; Reliability Engineering and System Safety; Bearing dates of Oct. 16, 2003, Sep. 3, 2004, Nov. 21, 2004 and 2005; pp. 305-330; vol. 89; Elsevier Ltd.
Helton et al.; "A Sampling-Based Computational Strategy for the Representation of Epistemic Uncertainty in Model Predictions With Evidence Theory"; Comput. Methods Appl. Mech. Engrg.; Bearing dates of Nov. 1, 2005, Oct. 30, 2006, Mar. 27, 2007 and 2007; pp. 3980-3998; vol. 196; Elsevier B.V.
Helton et al.; "Illustration of Sampling-Based Methods for Uncertainty and Sensitivity Analysis"; Risk Analysis; Bearing a date of 2002; pp. 591-622; vol. 22, No. 3; Society for Risk Analysis.
Helton et al.; "Latin Hypercube Sampling and the Propagation of Uncertainty in Analyses of Complex Systems"; Reliability Engineering & System Safety; Bearing dates of Jan. 28, 2003, Feb. 25, 2003 and 2003; pp. 23-69; vol. 81; Elsevier Science Ltd.
Helton et al.; "Sensitivity Analysis in Conjunction with Evidence Theory Representations of Epistemic Uncertainty"; Reliability Engineering and System Safety; Bearing dates of Jan. 19, 2006 and 2006; pp. 1414-1434; vol. 91; Elsevier Ltd.
Helton et al.; "Survey of Sampling-Based Methods for Uncertainty and Sensitivity Analysis"; Reliability Engineering and System Safety; Bearing dates of Jan. 18, 2006 and 2006; pp. 1175-1209; vol. 91; Elsevier Ltd.
Helton, J.C.; "Uncertainty and Sensitivity Analysis for Models of Complex Systems"; Computational Methods in Transport: Verification and Validation; Bearing a date of 2008; pp. 207-228.
Henderson, R.H.; "The World Health Organization's Plan of Action for Global Eradication of Poliomyelitis by the Year 2000"; Annals New York Academy of Sciences; Bearing dates of Dec. 17, 2006 and 1989; pp. 69-85; printed on Apr. 16, 2012.
Hoeting et al.; "An Improved Model for Spatially Correlated Binary Responses"; Journal of Agricultural, Biological, and Environmental Statistics; Bearing a date of Mar. 2000; pp. 102-114; vol. 5, No. 1; American Statistical Association and the International Biometric Society.
Hong et al.; "A Brief Introduction to Optimization Via Simulation"; Proceedings of the 2009 Winter Simulation Conference; Bearing a date of 2009; pp. 75-85; IEEE.
Hora et al.; "A Distribution-Free Test for the Relationship Between Model Input and Output When Using Latin Hypercube Sampling"; Reliability Engineering and System Safety; Bearing dates of Jun. 11, 2002, Oct. 14, 2002 and 2003; pp. 333-339; vol. 79; Elsevier Science Ltd.
Huffer et al.; "Markov Chain Monte Carlo for Autologistic Regression Models with Application to the Distribution of Plant Species"; Biometrics; Bearing a date of Jun. 1998; pp. 509-524; vol. 54, No. 2.
Jin et al.; "An Efficient Algorithm for Constructing Optimal Design of Computer Experiments"; Journal of Statistical Planning and Inference; Bearing dates of Feb. 10, 2003, Feb. 5, 2004, Jul. 23, 2004 and 2005; pp. 268-287; vol. 134; Elsevier B.V.
Jin et al.; "On Sequential Sampling for Global Metamodeling in Engineering Design"; Proceedings of DETC'02 ASME 2002 Design Engineering Technical Conferences and Computers and Information in Engineering Conference; Bearing dates of Sep. 29-Oct. 2, 2002; pp. 1-10.
Johnson et al.; "An Uncertainty Analysis and Sensitivity Analysis of the ASSA2002 AIDS and Demographic Model"; Centre for Actuarial Research; Bearing a date of Mar. 2006; pp. 1-98.
Jones et al.; "A Brief Survey of Bandwidth Selection for Density Estimation"; Journal of the American Statistical Association; Bearing a date of Mar. 1996; pp. 401-407; vol. 91, No. 433.
Jourdan et al.; "A New Criterion Based on Kullback-Leibler Information for Space Filling Designs"; Bearing a date of Apr. 16, 2009; pp. 1-15.
Jourdan et al.; "Optimal Latin Hypercube Designs for the Kullback-Leibler Criterion"; AStA Adv Stat Anal; Bearing dates of Aug. 28, 2009, Feb. 25, 2010 and 2010; pp. 341-351; vol. 94.
Kelsall et al.; "Spatial Variation in Risk of Disease: A Nonparametric Binary Regression Approach"; Appl. Statist.; Bearing dates of Dec. 1996, Jan. 1998 and 1998; pp. 559-573; vol. 47, Part 4; Royal Statistical Society.
Khuri et al.; "Response Surface Methodology"; WIREs Computational Statistics; Bearing dates of Mar./Apr. 2010; pp. 128-149; vol. 2; John Wiley & Sons, Inc.
Killeen et al.; "The Potential Impact of Integrated Malaria Transmission Control on Entomologic Inoculation Rate in Highly Endemic Areas"; Am. J. Trop. Med. Hyg.; Bearing a date of 2000; pp. 545-551; vol. 62, No. 5; The American Society of Tropical Medicine and Hygiene.
Kleijnen et al.; "Application-Driven Sequential Designs for Simulation Experiments: Kriging Metamodelling"; Journal of the Operational Research Society; Bearing dates of Aug. 3, 2004 and 2004; 8 Total Pages; Operational Research Society Ltd.

(56) References Cited

OTHER PUBLICATIONS

Kleijnen, J.P.C.; "An Overview of the Design and Analysis of Simulation Experiments for Sensitivity Analysis"; European Journal of Operational Research; Bearing dates of Aug. 1, 2003, Jan. 28, 2004, Mar. 25, 2004 and 2005; pp. 287-300; vol. 164; Elsevier B.V.

Kleijnen, J.P.C.; "Chapter 6: Experimental Design for Sensitivity Analysis, Optimization, and Validation of Simulation Models"; Handbook of Simulation: Principles, Methodology, Advances, Applications, and Practice; Bearing a date of 1998; pp. 173-223; John Wiley & Sons, Inc.

Kleijnen, J.P.C.; "Design and Analysis of Monte Carlo Experiments"; Bearing a date of 2004; pp. 1-20.

Kleijnen, J.P.C.; "Design of Experiments: Overview"; Proceedings of the 2008 Winter Simulation Conference; Bearing a date of 2008; pp. 479-488; IEEE.

Kleijnen, J.P.C.; "Kriging Metamodeling in Simulation: A Review"; European Journal of Operational Research; Bearing dates of Feb. 16, 2007, Oct. 5, 2007, Oct. 17, 2007 and 2009; pp. 707-716; vol. 192; Elsevier B.V.

Kleijnen et al.; "Stochastics and Statistics: Constrained Optimization in Expensive Simulation: Novel Approach"; European Journal of Operational Research; Bearing dates of Jan. 26, 2009, May 1, 2009, May 15, 2009 and 2010; pp. 164-174; vol. 202; Elsevier B.V.

Law et al.; Simulation Modeling and Analysis-Table of Contents: Third Edition; Bearing a date of 2000; 11 Total Pages; McGraw-Hill.

Lempert et al.; "Confronting Surprise"; Social Science Computer Review; Bearing a date of Winter 2002; pp. 420-440; vol. 20, No. 4; Sage Publications.

Lin, GE; "A Spatial Logit Association Model for Cluster Detection"; Geographical Analysis; Bearing a date of Oct. 2003; pp. 329-340; vol. 35, No. 4.

Lindley, D.V.; "On a Measure of the Information Provided by an Experiment"; The Annals of Mathematical Statistics; Bearing a date of Aug. 2, 1955; pp. 986-1005.

Liu et al.; "Relative Entropy Based Method for Global and Regional Sensitivity Analysis in Probabilistic Design"; Proceedings DETC'04 ASME 2004 International Design Engineering Technical Conferences & Computers and Information in Engineering Conference; Bearing dates of Sep. 28-Oct. 3, 2004; pp. 1-10.

Loftsgaarden et al.; "A Nonparametric Estimate of a Multivariate Density Function"; The Annals of Mathematical Statistics; Bearing a date of Jun. 1965; pp. 1049-1051; vol. 36, No. 3.

Lollini et al.; "Discovery of Cancer Vaccination Protocols with a Genetic Algorithm Driving an Agent Based Simulator"; BMC Bioinformatics; Bearing a date of Jul. 20, 2006; pp. 1-9; vol. 7, No. 352.

Longini Jr. et al.; "An Optimization Model for Influenza A Epidemics"; Mathematical Biosciences; Bearing dates of Sep. 15, 1977 and 1978; pp. 141-157; vol. 38; Elsevier North-Holland, Inc.

Losina et al.; "The 'Art' of Linkage: Pre-Treatment Loss to Care after HIV Diagnosis at Two PEPFAR Sites in Durban, South Africa"; PLoS One; Bearing a date of Mar. 2010; pp. 1-8; vol. 5, Issue 3.

Makler-Pick, et al.; "Sensitivity Analysis for Complex Ecological Models—A New Approach"; Environmental Modelling & Software; Bearing dates of Sep. 3, 2009, Jun. 27-28, 2010, Aug. 17, 2010 and 2011; pp. 124-134; vol. 26; Elsevier Ltd.

Marino et al.; "A Methodology for Performing Global Uncertainty and Sensitivity Analysis in Systems Biology"; J. Theor. Biol.; Bearing a date of Sep. 7, 2008; pp. 178-196; vol. 254, No. 1.

Marrel et al.; "Global Sensitivity Analysis of Stochastic Computer Models with Joint Metamodels"; Statistics and Computing; Bearing a date of Nov. 6, 2011; pp. 1-15; Springer.

McKay et al.; "A Comparison of Three Methods for Selecting Values of Input Variables in the Analysis of Output from a Computer Code"; Technometrics; Bearing a date of May 1979; pp. 239-245; vol. 21, No. 2.

Morris, M.D.; "Factorial Sampling Plans for Preliminary Computational Experiments"; Technometrics, Bearing a date of May 1991; pp. 161-174; vol. 33, No. 2.

Nadaraya, E.A.; "On Non-Parametric Estimates of Density Functions and Regression Curves"; Theory of Probability and its Applications; Bearing a date of Jul. 2, 1964; pp. 186-190; vol. 10, Issue 1.

Neddermeijer et al.; "A Framework for Response Surface Methodology for Simulation Optimization"; Proceedings of the 2000 Winter Simulation Conference; Bearing a date of 2000; pp. 129-136.

Okell et al.; "Modelling the Impact of Artemisinin Combination Therapy and Long-Acting Treatments on Malaria Transmission Intensity"; PLoS Medicine; Bearing a date of Nov. 2008; pp. 1617-1628; vol. 5, Issue 11.

Okell et al.; "Reduction of Transmission from Malaria Patients by Artemisinin Combination Therapies: A Pooled Analysis of Six Randomized Trials"; Malaria Journal; Bearing a date of Jul. 9, 2008; pp. 1-13; vol. 7, No. 125.

Olafsson et al.; "Simulation Optimization"; Proceedings of the 2002 Winter Simulation Conference; Bearing a date of 2002; pp. 79-84.

Pappalardo et al.; "Genetic Algorithm Against Cancer"; Bearing a date of 2006; pp. 223-228.

Pappalardo et al.; "Vaccine Protocols Optimization: In Silico Experiences"; Biotechnology Advances; Bearing dates of Jun. 14, 2009, Oct. 13, 2009, Sep. 30, 2009 and 2010; pp. 82-93; vol. 28; Elsevier Inc.

Park et al.; "Comparison of Data-Driven Bandwidth Selectors"; Journal of the American Statistical Association; Bearing a date of Mar. 1990; pp. 66-72; vol. 85, No. 409.

Patel et al.; "Finding Optimal Vaccination Strategies for Pandemic Influenza Using Genetic Algorithms"; Journal of Theoretical Biology; Bearing dates of May 6, 2004, Sep. 23, 2004, Nov. 22, 2004, Jan. 20, 2005 and 2005; pp. 201-212; vol. 234; Elsevier Ltd.

Pennisi et al.; "Optimal Vaccination Schedules Using Simulated Annealing"; Bioinformatics; Bearing dates of Mar. 31, 2008, Jun. 3, 2008, Jun. 5, 2008 and 2008; pp. 1740-1742; vol. 24, No. 15; Oxford University Press.

Penny et al.; "What Should Vaccine Developers Ask? Simulation of the Effectiveness of Malaria Vaccines"; PLoS One; Bearing a date of Sep. 2008; pp. 1-14; vol. 3, Issue 9.

Ribeiro et al.; "A Stochastic Model for Primary HIV Infection: Optimal Timing of Therapy"; AIDS; Bearing dates of Sep. 16, 1998, Nov. 12, 1998, Nov. 18, 1998 and 1999; pp. 351-357; vol. 13; Lippincott Williams & Wilkins.

Riggs et al.; "A Comparison of Random vs. Chemotaxis Driven Contacts of T Cells with Dendritic Cells During Repertoire Scanning"; J. Theor. Biol.; Bearing a date of Feb. 21, 2008; pp. 732-751 (33 Total Pages); vol. 250, No. 4.

Roberts, L.; "Polio: No Cheap Way Out"; Science; Bearing a date of Apr. 20, 2007; pp. 362-363; vol. 316; AAAS.

Rodgers et al.; "Thirteen Ways to Look at the Correlation Coefficient"; The American Statistician; Bearing a date of Feb. 1988; pp. 59-66; vol. 42, No. 1.

Ross et al.; "Modelling the Epidemiological Impact of Intermittent Preventive Treatment Against Malaria in Infants"; PLoS One; Bearing a date of Jul. 2008; pp. 112; vol. 3, Issue 7.

Sabin et al.; "Live, Orally Given Poliovirus Vaccine: Effects of Rapid Mass Immunization on Population Under Conditions of Massive Enteric Infection with other Viruses"; The Journal of the American Medical Association; Bearing a date of Aug. 6, 1960; pp. 1521-1526; vol. 173, No. 14; Bulletin of the World Health Organization.

Sabuncuoglu et al.; "Simulation Metamodelling with Neural Networks: An Experimental Investigation"; International Journal of Production Research; Bearing a date of 2002; pp. 2483-2505; vol. 40, No. 11; Taylor & Francis; printed on Mar. 14, 2012.

Sacks et al.; "Design and Analysis of Computer Experiments"; Statistical Science; Bearing a date of Nov. 1989; pp. 409-423; vol. 4, No. 4.

Salk, J.E.; "Considerations in the Preparation and Use of Poliomyelitis Virus Vaccine"; The Journal of the American Medical Association; Bearing a date of Aug. 6, 1955; pp. 1239-1248; vol. 158, No. 14.

Samples et al.; "Parameter Sweeps for Exploring Parameter Spaces of Genetic and Evolutionary Algorithms"; Studies in Computational Intelligence; Bearing a date of 2007; pp. 161-184; Springer-Verlag Berlin Heidelberg.

Schuëller et al.; "A Critical Appraisal of Reliability Estimation Procedures for High Dimensions"; Probabilistic Engineering Mechanics; Bearing dates of Jan. 22, 2004, May 11-12, 2004 and 2004; pp. 463-474; vol. 19; Elsevier Ltd.

(56) References Cited

OTHER PUBLICATIONS

Scott et al.; "Multi-Dimensional Density Estimation"; Bearing a date of Aug. 31, 2004; pp. 1-39; Elsevier Science.

Segovia-Juarez et al.; "Identifying Control Mechanisms of Granuloma Formation During M. Tuberculosis Infection Using an Agent-Based Model"; Journal of Theoretical Biology; Bearing a date of Aug. 26, 2004; pp. 357-376; vol. 231; Elsevier Ltd.

Shi et al.; "Particle Swarm Optimization: Developments, Applications and Resources"; Evolutionary Computation: Proceedings of the 2001 Congress; Bearing a date of 2001; pp. 81-86; vol. 1; IEEE.

Silverman, B.W.; Density Estimation for Statistics and Data Analysis-Table of Contents; Monographs on Statistics and Applied Probability; Bearing a date of 1986; 6 Total Pages; vol. 26; Chapman & Hall.

Smith et al.; "A Note on Bayes Designs for Inference Using a Hierarchical Linear Model"; Biometrika; Bearing a date of 1980; pp. 613-619; vol. 67, No. 3; printed on Mar. 14, 2012.

Stover, J.; "HIV Models to Inform Health Policy"; Curr. Opin. HIV AIDS; Bearing a date of 2011; pp. 108-113; vol. 6; Lippincott Williams & Wilkins.

Stover, J.; "Projecting the Demographic Consequences of Adult IV Prevalence Trends: The Spectrum Projection Package"; Sex Transm Infect; Bearing a date of 2004; pp. i14-i18; vol. 80, Suppl 1.

Swisher et al.; "A Survey of Simulation Optimization Techniques and Procedures"; Proceedings of the 2000 Winter Simulation Conference; Bearing a date of 2000; pp. 119-128.

Tekin et al.; "Simulation Optimization: A Comprehensive Review on Theory and Applications"; IIE Transactions; Bearing dates of Jan. 2001, Mar. 2004 and 2004; pp. 1067-1081; vol. 36, No. 11; printed on Mar. 14, 2012.

Thompson et al.; "Using System Dynamics to Develop Policies that Matter: Global Management of Poliomyelitis and Beyond"; System Dynamics Review; Bearing dates of Sep. 2008, Oct. 2008 and Winter 2008; pp. 433-449; vol. 24, No. 4; John Wiley & Sons, Ltd.

Trucano et al.; "Calibration, Validation, and Sensitivity Analysis: What's What"; Reliability Engineering and System Safety; Bearing a date of Jan. 19, 2006; pp. 1331-1357; vol. 91, Elsevier Ltd.

Van Beers et al.; "Customized Sequential Designs for Random Simulation Experiments: Kriging Metamodeling and Bootstrapping"; European Journal of Operational Research; Bearing dates of Apr. 27, 2006, Feb. 26, 2007, Mar. 27, 2007 and 2008; pp. 1099-1113; vol. 186; Elsevier B.V.

Van Beers et al.; "Kriging Interpolation in Simulation: A Survey"; Proceedings of the 2004 Winter Simulation Conference; Bearing a date of 2004; pp. 113-121.

Van Beers, W.C.M.; "Kriging Metamodeling in Discrete-Event Simulation: An Overview"; Proceedings of the 2005 Winter Simulation Conference; Bearing a date of 2005; pp. 202-208.

Wahba, G.; Spline Models for Observational Data-Table of Contents; Bearing a date of 1990; 5 Total Pages; Society for Industrial and Applied Mathematics.

Wand et al.; Kernel Smoothing-Table of Contents; Monographs on Statistics and Applied Probability; Bearing a date of 1995; 5 Total Pages; vol. 60; CRC Press.

Wang et al.; "Reliability Assessment Using Discriminative Sampling and Metamodeling"; Bearing a date of 2005; pp. 1-10; SAE International.

Wang et al.; "Review of Metamodeling Techniques in Support of Engineering Design Optimization"; Journal of Mechanical Design; Bearing a date of Apr. 2007; pp. 370-380; vol. 129; ASME.

Watson, G.S.; "Smooth Regression Analysis"; Sankhyā: The Indian Journal of Statistics, Series A; Bearing a date of Dec. 1964; pp. 359-372; vol. 26, No. 4; Springer.

Wu et al.; "Modelling the Distribution of Plant Species Using the Autologistic Regression Model"; Environmental and Ecological Statistics; Bearing dates of Aug. 1995, Aug. 1996 and 1997; pp. 49-64; vol. 4; Chapman & Hall.

Zou et al.; "An Indicator Response Surface Method for Simulation-Based Reliability Analysis" Journal of Mechanical Design; Bearing a date of Jul. 2008; pp. 071401-1 to 071401-11; vol. 130; printed on Mar. 14, 2012.

Zou et al.; "An Indicator Response Surface-Based Monte Carlo Method for Efficient Component and System Reliability Analysis"; Proceedings of the DETC'03 ASME 2003 Design Engineering Technical Conferences and Computers and Information in Engineering Conference; Bearing dates of Sep. 2-6, 2003; pp. 1-10; ASME; printed on Mar. 14, 2012.

Joseph et al.; "Bayesian Estimation of Disease Prevalence and the Parameters of Diagnostic Tests in the Absence of a Gold Standard"; American Journal of Epidemiology; bearing a date of 1995; pp. 263-272; vol. 141, No. 3; The Johns Hopkins University School of Hygiene and Public Health.

* cited by examiner

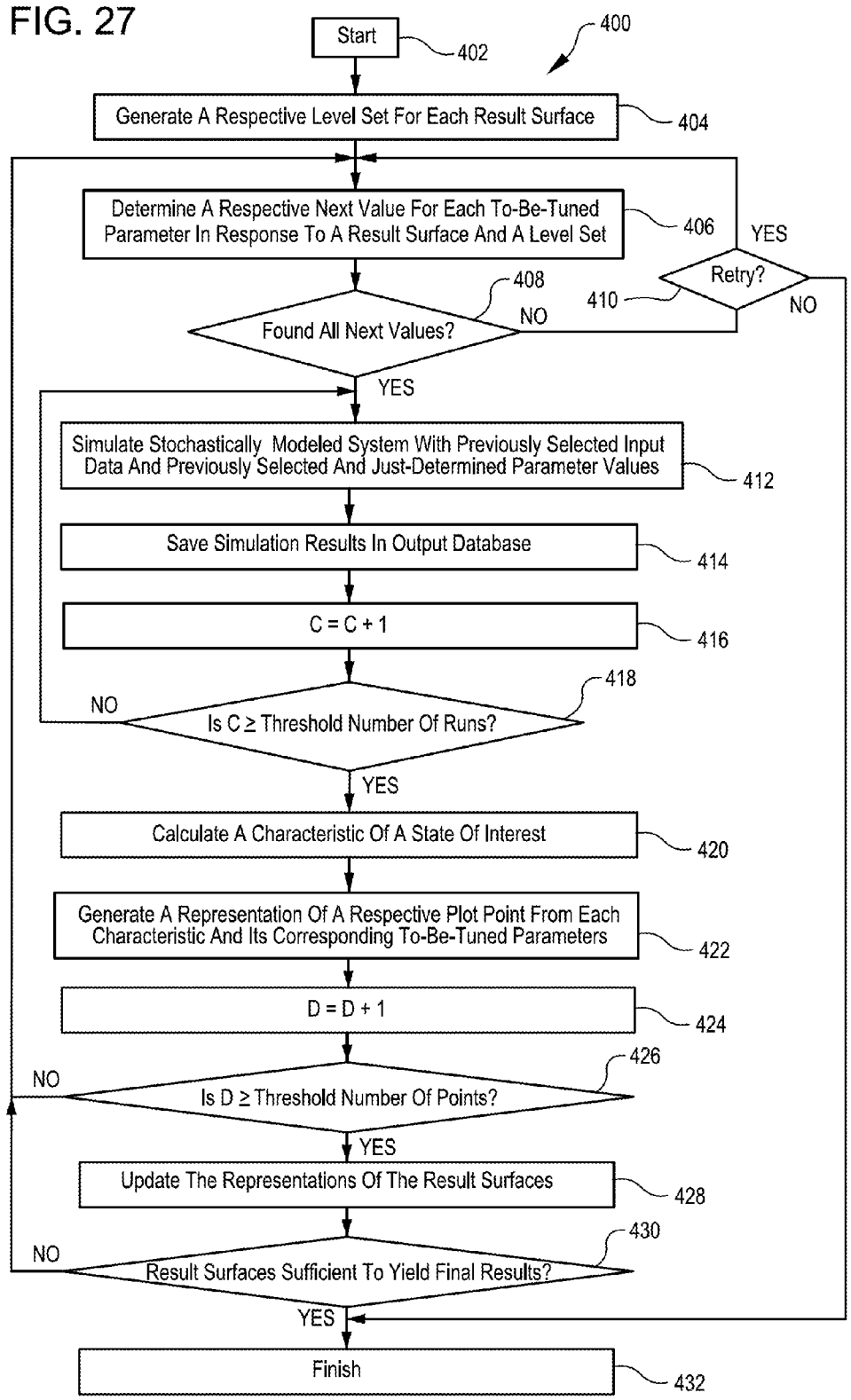

DETERMINING A NEXT VALUE OF A SYSTEM-SIMULATION PARAMETER IN RESPONSE TO A REPRESENTATION OF A PLOT HAVING THE PARAMETER AS A DIMENSION

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/199,040, titled DETERMINING A NEXT VALUE OF A PARAMETER FOR SYSTEM SIMULATION, naming Michael H. Baym, Philip Andrew Eckhoff, Daniel Jay MacDonald, Nathan P. Myhrvold, Karima R. Nigmatulina, Charles Whitmer, Lowell L. Wood, Jr. as inventors, filed Aug. 16, 2011, which is filed on the same date as the instant application, or is an application of which a currently co-pending application is entitled to the benefit of the filing date;

For purposes of the USPTO extra-statutory requirements, the present application constitutes a continuation-in-part of U.S. patent application Ser. No. 13/199,039, titled DETERMINING A NEXT VALUE OF A SYSTEM-SIMULATION PARAMETER IN RESPONSE TO REPRESENTATIONS OF PLOTS HAVING THE PARAMETER AS A DIMENSION, naming Michael H. Baym, Philip Andrew Eckhoff, Daniel Jay MacDonald, Nathan P. Myhrvold, Karima R. Nigmatulina, Charles Whitmer, Lowell L. Wood, Jr. as inventors, filed Aug. 16, 2011, which is filed on the same date as the instant application, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

An embodiment of an apparatus includes a simulator, generator, and determiner. The simulator is configured to simulate a system and to propagate at least one state of the simulated system through time in response to a value of a parameter, and the generator is configured to generate a representation of a region of a plot having dimensions that respectively correspond at least to the parameter and to a characteristic of a state of the simulated system. And the determiner is configured to determine a next value of the parameter in response to the representation of the region.

Such a generator may be configured to generate a representation of a result surface having at least the parameter and state characteristic as dimensions, and, as compared to existing simulation techniques, such a determiner may use the representation of the result surface to lead one to discover more quickly a range of parameter values that corresponds to a sought-after result, or to discard more quickly a range of parameter values that does not correspond to a sought-after result. For example, when simulating a disease-transmission system, such a determiner may use a representation of a result surface to lead one more quickly to a range of values for a disease-remediation parameter (e.g., the percentage of the population vaccinated) that corresponds to a sought-after probability of eliminating a disease from a region; or, such a determiner may use a representation of a result surface to lead one to discover more quickly a range of values for the disease-remediation parameter that is insufficient to eliminate the disease from the region. In addition, the determiner may allow one to focus on a feature (e.g., peak, valley, slope, or plateau) of a result surface for the purpose of obtaining information such as a sensitivity of a sought-after result to a parameter.

BRIEF DESCRIPTION OF THE FIGURES

FIG. 27 is a flow chart of an embodiment of a technique for using a simulation-result surface to determine a next value of a parameter for system simulation, for running a simulation of a system in response to the next value of the parameter, and for updating the result surface.

DETAILED DESCRIPTION

Figure 1:
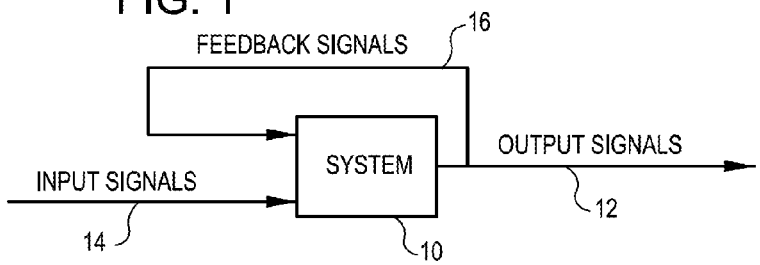
FIG. 1 is a block diagram of an embodiment of a system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

One or more embodiments are described with reference to the drawings, wherein like reference numerals may be used to refer to like elements throughout. In the following description, for purposes of explanation, numerous specific details are set forth in order to provide a thorough understanding of the one or more embodiments. It may be evident, however, that one or more embodiments may be practiced without these specific details. In other instances, well-known structures and devices are shown in block diagram form in order to facilitate describing one or more embodiments.

Organizations such as the World Health Organization (WHO), have, for many years, tried to eradicate certain human diseases such as malaria, polio, and guinea worm, from the planet. But to date, the only human disease that is known to have been eradicated by human intervention is smallpox—rinderpest, an animal-specific disease, has also been eradicated by human intervention.

Therefore, to assist these organizations in developing cost-effective disease-eradication or disease-elimination campaigns that have good probabilities of success, scientists have developed simulation apparatuses/tools (hereinafter simulation tools) for simulating disease-transmission systems. In general, the goal of a disease-eradication campaign is eradication of a disease from the entire planet, and the goal of a disease-elimination campaign is eradication of a disease from one or more regions of the planet; that is, elimination of a disease from the entire planet may be called eradication. But "eradication" and "elimination" are used interchangeably herein to mean removal of a disease from one or more regions of the planet, or from the entire planet.

Such a simulation tool typically includes a model of a disease-transmission system, where this system model includes one or more complex microsimulations of phenomena that compose the system. Typically, such a microsimulation defines a relationship between a phenomenon to be simulated and the environment in which the phenomenon is immersed. For example, a microsimulation may define the life cycle of a malaria parasite (there is more than one such parasite) while inside a mosquito host in terms of the weather of the region in which the mosquito resides. Or, a microsimulation may define the life cycle of a malaria parasite while inside a human host in terms of the immunity level of the host (e.g., is the host vaccinated, was the host previously infected), or it may define the transmission of a malaria parasite from human to mosquito and from mosquito to human in terms of the level of interaction between humans and mosquitos (e.g., percentage of bed-net coverage, percentage of sleeping quarters with screens) in a region of interest.

To determine whether or not a disease-elimination campaign is likely to be successful, one first provides the simulation tool with values of the parameters (e.g., vaccination coverage, education, campaign duration) of the campaign.

Next, the simulation tool simulates the disease-transmission system in response to the input campaign parameters, and generates one or more campaign output results, such as the probability that the number of individuals infected with the disease at the end of the campaign is zero (i.e., successful elimination).

Then, if the campaign results are satisfactory, then one may use the simulated campaign-parameter values in an actual campaign knowing that these values are likely to yield a sought-after result (e.g., a 99% or higher probability of elimination).

Alternatively, if the campaign results are not satisfactory, then one may re-simulate the disease-transmission system with a different set of campaign-parameter values, and repeat this procedure until he/she finds a set of values that corresponds to a sought-after result, or until he/she determines that no such set of values is likely to exist.

Unfortunately, as discussed below in more detail, this hit-or-miss procedure of trying different sets of campaign-parameter values may require a total simulation time that is relatively long, and that may be impractical.

More specifically, an elimination-campaign simulation tool may simulate a disease-transmission system by simulating a large number of individual stochastic states/events at discrete times over the campaign period, where the probabilities of states/events occurring or not occurring may be weighted according to parameterized data. For example, the simulation tool may, as part of a simulation, predict whether a particular in-silico (i.e., simulated) individual within a particular region will become infected with a malaria parasite at a particular time based on a probability of infection that depends on factors such as the region's weather, whether the individual has a bed net, whether the bed net is treated with a mosquitocide, and the probability that the individual will use the bed net if he/she has one. The number of simulated individuals infected at any given simulation time is a state of the simulated system, as is the number of individuals that are not infected at any given simulation time. Furthermore, when an uninfected individual becomes infected is an event of the simulated system, as is when an infected individual becomes uninfected.

Due to the large number states/events and other complex phenomena that compose the simulated disease-transmission system, the time that a simulation tool requires to run a simulation may be significant, particularly when the tool is simulating a campaign on a very large scale (e.g., over a large geographical area, over a large population, or over a long campaign period). For example, just a single simulation at a particular set of campaign-parameter values may take hours, days, or even weeks depending on the tool's computing power, and one may need to run many (e.g., 100, 1000, or even more) simulations to determine within a reasonable statistical certainty whether the set of campaign-parameter values corresponds to a sought-after result (e.g., a 99% or higher probability of eradicating the disease).

Therefore, designers of tools for simulating disease-transmission systems and other complex systems (e.g., weather systems, economic systems) continue to search for ways to reduce the overall time that a simulation tool requires to simulate a system sufficiently for a particular purpose, such as for determining whether a particular set of input-parameter values corresponds to a sought-after result.

As discussed below, an embodiment of a simulation tool may decrease its overall simulation time by reducing the time that that the tool takes to discover whether there exists a range of input-parameter values that corresponds to a sought-after result, and, if such a range exists, by reducing the time that the tool takes to characterize this range. For example, an embodiment of a simulation tool may select a next set of input-parameter values based on simulation results yielded by one or more preceding sets of input-parameter values.

Before discussing such an embodiment of a simulation tool in more detail, some general system-related concepts, and system-simulation-related concepts, are discussed.

FIG. 1 is a block diagram of a feedback system 10, which has one or more states S and generates one or more output signals 12 in response to one or more input signals 14 and one or more feedback signals 16. As discussed below, depending on the system 10, the output, input, and feedback signals 12, 14, and 16 may be electromagnetic or other types of signals, or may be quantities other than signals.

If the system 10 is a continuous-time system, then the values of its states S may vary smoothly with time; such a system is sometimes called an analog system.

In contrast, if the system 10 is a discrete-time system, then the values of its states S change at discrete time intervals; such a system is sometimes called a digital system.

The output signals 12 are the signals that constitute the values of one or more of the states S at the output of the system 10. If the system 10 is a continuous-time system, then the output signals 12 may be analog signals, whereas if the system 10 is a discrete-time system, then the output signals may be digital signals having values or levels that change from discrete-time interval to discrete-time interval. Furthermore, there may be more states S than there are output signals 12; that is, not every state need be an output of the system 10.

The input signals 14 may also be analog or digital signals, and are, or represent, stimuli in response to which the system 10 generates the output signals 12. In other words, the input signals 14 "drive" the system 10.

The feedback signals 16 are equal to, or are otherwise derived from, one or more of the output signals 12. For example, a feedback signal 16 may be related to a corresponding output signal 12 by a scalar (e.g., 5, ½), may be a linear (e.g., derivative, integral) or non-linear function of the corresponding output signal, or may be a combination of multiple output signals 12 or signals derived from such output signals. Furthermore, although shown as being derived from the output signals 12, one or more of the feedback signals 16 may be derived from intermediate state values that the system 10 generates but does not provide as output signals. For example, if the system has multiple stages, then a feedback signal 16 may be derived from the output of one of the stages other than the last stage.

The system 10 may be linear system, which has a behavior that one may predict almost exactly for virtually any set of initial conditions and virtually any values of the input signals 14, or the system may be a non-linear system (sometimes called a chaotic system), which has a behavior that one may not predict exactly for virtually any set of initial conditions and virtually any values of the input signals. A significant number of predictable linear systems (e.g., a cruise-control system for a vehicle, a temperature-control system for a building) are designed by humans, and a significant number of the more-difficult-to-predict non-linear systems are naturally occurring systems (e.g., weather systems), or are human-built or human-influenced systems over which humans may have only partial control (e.g., economic systems, disease-transmission systems).

An example of a relatively simple linear system 10 is a cruise-control system for maintaining the speed of a vehicle at a relatively constant value, where an output signal 12 is a signal that represents the actual speed of the vehicle, an input signal 14 is a signal that represents the desired speed of the vehicle, and a feedback signal 16 equals the output signal.

In operation, the cruise-control system 10 generates the output signal 12 such that the difference between the input and feedback signals 14 and 16 stably tends toward zero.

For example, suppose the input signal 14 indicates a desired speed of 60 miles per hour (mph), and at an arbitrary initial time the output signal 12 and feedback signal 16 indicate an actual speed of 50 mph. In response to this initial condition, the cruise-control system 10 increases the speed of the vehicle until the output and feedback signals 12 and 16 indicate a speed of 60 mph, and thereafter maintains the speed of the vehicle at 60 mph.

Similarly, suppose the input signal 14 indicates a desired speed of 60 miles per hour (mph), and at an arbitrary initial time the output signal 12 and feedback signal 16 indicate an actual speed of 70 mph. In response to this condition, the cruise-control system 10 decreases the speed of the vehicle until the output and feedback signals 12 and 16 indicate a speed of 60 mph, and thereafter maintains the speed of the vehicle at 60 mph.

Consequently, regardless of the initial speed of the vehicle and other initial conditions of the system, and regardless of subsequent conditions (e.g., different incline of road, different weather) of the system, the cruise-control system 10 exhibits the predictable (and sought-after) behavior of bringing the speed of the vehicle to 60 mph, and thereafter maintaining the speed at 60 mph.

An example of a non-linear system 10 is a human-disease-transmission system, such as described above, that governs the spread of a disease such as malaria or polio among humans in a given region. In such a system, the input signals 14 represent the values of actual quantities such as average rainfall and average temperature for the region, the percentage of the region's population who are vaccinated, and the timing of the vaccinations, the output signals 12 represent the actual values of system states such as the number of individuals infected with a disease, the number of individuals immune to the disease, and the location of each individual, and the feedback signals 16 represent the output signals or a subset thereof.

In operation, unlike in a linear system, the output signals 12 may not converge to predictable target values that are independent of the initial conditions and the subsequent conditions of the system during the time period of interest; instead, the values of the output signals 12 at the end of a time period of interest may depend heavily not only on the initial conditions of the system, but also on the subsequent conditions of the system that develop during the time period of interest.

For example, consider a disease-transmission system having input signals with given values and where one of the output signals 12 represents the number of infected individuals at the end of a disease-elimination-campaign period of ten years. Even assuming given values for the input signals 14, the number of infected individuals at the end of the campaign period may depend heavily on the number of individuals infected at the beginning of the campaign period (an initial condition), and may also depend heavily on the weather and the migration patterns of the individuals in the region of interest during the campaign period (subsequent conditions).

Consequently, even assuming unchanging input signals 14, the number of infected individuals at the end of an elimination-campaign period may vary significantly depending on the initial and subsequent conditions of the system.

Figure 2:
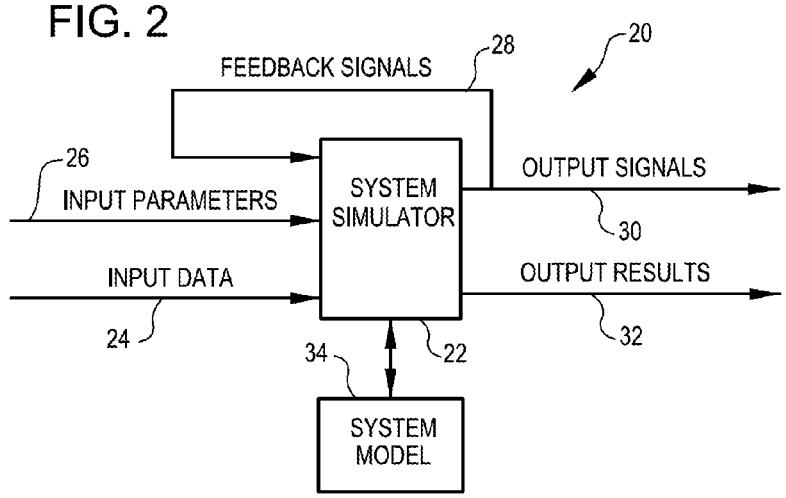
FIG. 2 is a block diagram of an apparatus/tool for simulating a system.

FIG. 2 is a block diagram of an embodiment of a system-simulation tool 20 for simulating a system such as the system 10 of FIG. 1. The tool 20 includes a system simulator 22, which receives input data 24, input parameters 26, and feedback signals 28, and which generates output signals 30 and output results 32 in response to a system model 34.

The simulator 22 may include a computing apparatus (e.g., a computing system having one or more processors) that operates under the control of the system model 34, which may include software, firmware, hardware, or a combination or sub-combination thereof, that causes the simulator to act, at least in an algorithmic sense, as the system being simulated.

The simulator 22 simulates a system by propagating the states of the simulated system through time at discrete time steps. This may be true even if the system being simulated is a continuous-time system such as a cruise-control system. Because there are conventional techniques for generating a discrete-time model of a continuous-time system, such techniques are not further described.

The input data 24 are signals that represent input information that an operator of the tool 20 does not manipulate for purposes of the simulation. For example, where the system being simulated is a cruise-control system, such input data may include the weight of the vehicle and the power profile of the engine. Or, where the system being simulated is a disease-transmission system, the input data 24 may include population and hours-of-daylight data for a region.

The input parameters 26 are signals that represent input information that an operator of the tool 20 may manipulate for purposes of the simulation. For example, where the system being simulated is a cruise-control system, such input information may include the terrain (e.g., flat, mountainous) over which a vehicle will travel during the simulation. Or, where the simulated system is a disease-transmission system, the input parameters 24 may include the percentage of the population to receive a vaccination during the simulation period, and the timing of these vaccinations.

The feedback signals 28 may be equal to, or derived from, the output signals 30 and output results 32.

The output signals 30 represent the values of one or more of the states S of the simulated system after each discrete time step. For example, if the system being simulated is a cruise-control system, then one of the output signals 30 may represent the simulated speed of the simulated vehicle. Or, if the system being simulated is a disease-transmission system, then one of the output signals 30 may represent the number of individuals infected with a disease.

The output results 32 include information that may be derived from the output signals 30, and thus from one or more of the states S, of the simulated system. For example, if the system being simulated is a cruise-control system, then an output result 32 may be the time required for the vehicle to re-attain the cruising speed set by an input signal 24 in response to a sudden change in terrain (e.g., from flat road to steep incline). Or, if the system being simulated is a disease-transmission system, then an output result 32 may be whether a disease is eradicated (i.e., the number of infected individuals is zero) at the end of a disease-elimination campaign period, or may be the probability that the elimination-campaign eradicated the disease.

The system model 34 mathematically defines the system to be simulated. For example, if the system to be simulated is a linear system, then the system model 34 may include a set of linear equations that mathematically define the behavior of the simulated system regardless of the system's configuration. Or, if the system to be simulated is a non-linear system, then, as further discussed below, the system model 34 may define all the possible configurations of the simulated system, and may define the respective behaviors of the simulated system for each of these possible system configurations. Alternatively, the system model 34 may define the probabilities by which the system simulator 22 may select system configurations for simulation, and may define the behaviors of the simulated system for each of these selected configurations. Furthermore, although the system model 34 is described in the singular, it may include multiple models or microsimulations that together form the system model as described above.

Figure 3:
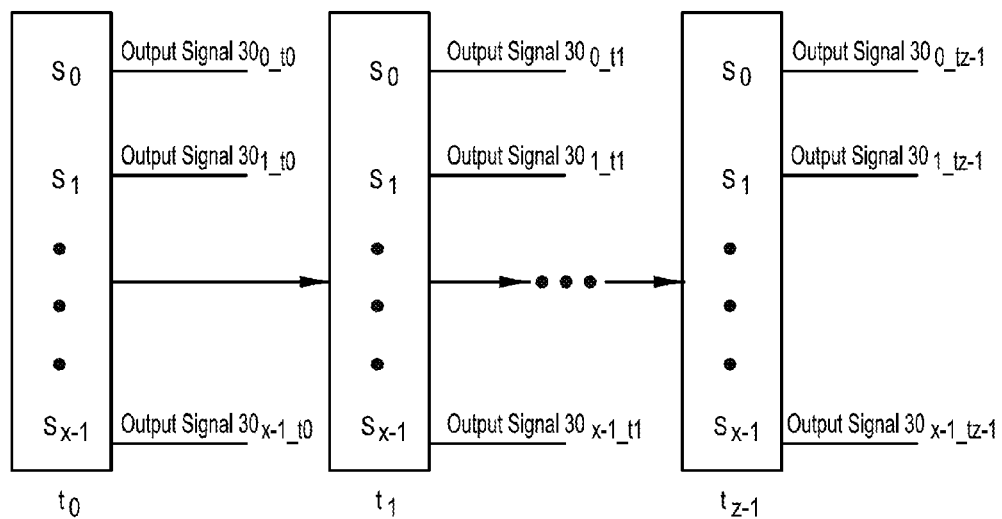
FIG. 3 is a timing diagram of the states of a system model as an embodiment of the apparatus of FIG. 2 propagates the states through time.

FIG. 3 is a timing diagram of the x states $S_1$-$S_{x-1}$ of the system simulated by the simulator 22 (FIG. 2) and defined by the system model 34 (FIG. 2) at each of the z time steps $t_0$-$t_{z-1}$ through which the simulator propagates the states. The interval between each time step may be constant such as in constant-time-interval simulation, or it may vary from step to step such as in event-based-time-interval simulation. Furthermore, the output signals 30, and thus the output results 34 (not shown in FIG. 3), may have different values at each time step.

The operation of the simulation tool 20 is now discussed in conjunction with FIGS. 2 and 3.

An operator of the simulation tool 20 first selects the input-data signals 24 and the values of the input-data signals (e.g., from an input data base), and selects the input parameters 24 and the values of the input parameters (e.g., enters them via a user interface). The operator may also be able to select the feedback signals 28 that are fed back to the input of the simulator 22.

Next, the simulator 22 simulates the system by effectively propagating the states S of the simulated system, as defined by the system model 34, through a period of time $t_0$-$t_{z-1}$, discrete time step by discrete time step.

Still referring to FIG. 2, modeling and simulation of a non-linear system is further discussed.

As discussed above in conjunction with FIG. 1, the output signals 12 of a non-linear system 10 may depend heavily on the initial conditions and the subsequent conditions of the system. For example, for a disease-transmission system, the number of infected individuals at the end of a disease-elimination campaign period may depend heavily on the number of individuals infected at the beginning of the campaign period (an initial condition), and may also depend heavily on the migration patterns of the individuals and the weather in the region of interest during the campaign period (subsequent conditions).

One potential way to simulate a non-linear system is to assume a particular configuration of the system, where the particular configuration includes known values of all initial conditions and of all subsequent conditions at each time step t of the simulation period.

Then, by propagating the states S of the so-configured system through time in response to the model 34, the simulator 22 may yield the output signals 30 and output results 32 for this particular system configuration.

For example, if the simulated system is a disease-transmission system, then one may assume a particular system configuration that includes a particular number of infected individuals at the beginning of a disease-elimination campaign, and a particular respective location for each individual at each time step of the simulation period.

But simulating a non-linear system 10, such as a disease-transmission system, based on a single system configuration is akin to trying to predict the future. For example, it would be difficult to impossible to predict exactly where each individual will be at the beginning of a campaign period, and how each individual will travel and interact with other individuals during the campaign period. Therefore, it would be difficult to impossible to predict what system configuration will exist during an actual campaign period.

Another potential way to simulate a non-linear system is for the simulation tool 20 to determine all possible configurations of the system, and then to simulate the system for each of these possible configurations. For example, if the non-linear system to be simulated is a disease-transmission system, then the simulation tool 20 would provide all possible outcomes of a disease-elimination campaign. And from these outcomes, the tool 20 may evaluate the level of success of the campaign. For example, the tool may calculate the probability of success as the ratio of the number of simulated system configurations in which a disease is eradicated (i.e., zero infected individuals at the end of the campaign period) to the total number of possible system configurations.

A problem with this simulate-all-configurations approach is that, at least for a large non-linear system, it may be impractical or impossible to determine each and every possible configuration of the system. For example, in a disease-transmission system that includes 100,000 people, and for a simulator 22 that operates with discrete time steps spaced apart by a constant interval equal to one day, it would be impractical or impossible to determine each possible set of locations for these 100,000 people each day over a campaign period such as 1-10 years.

And even if one could determine all possible configurations of a system, the time that the simulator 22 would need to simulate all of these configurations may be too long to be practical.

To illustrate the complexity of determining all possible configurations of a large non-linear system and simulating the system at each of these configurations, consider the game of chess. A chess board has thirty two pieces (e.g., individuals) and sixty four squares (e.g., locations). It has been estimated that the number of possible sets of chess moves (e.g., configurations of the locations of individuals), where each set of moves constitutes a complete game of chess (e.g., a disease-elimination campaign period) is approximately $10^{120}$. To put this number in perspective, the total number of atoms in the observable universe has been estimated at "only" around $10^{80}$! So one may see how expanding the number of chess pieces to 100,000 and expanding the chess board to many hundreds or thousands of square miles, increases the number of possible configurations to a number that makes the all-configurations approach impractical for all but the most simple non-linear systems.

Another potential technique for simulating a non-linear system is to determine a statistically independent subset of all possible configurations of the system, to use the simulation tool 20 to simulate each of the possible configurations in the subset, and to extrapolate the simulation results for this subset of configurations to all possible configurations. This technique is somewhat similar to forecasting election results by polling. For example, one brute-force way to forecast a presidential election is to phone every registered voter in the U.S. and to ask each voter for which candidate he/she will vote; but this would require over 200 million phone calls! Therefore, pollsters phone a small, statistically independent subset of registered voters (e.g., 1000 voters who represent all major political demographics), and then use statistics, and perhaps other mathematical techniques, to estimate the outcome of the election within a certain error bound.

One way to implement this statistical technique is to model a non-linear system as a stochastic (i.e., probabilistic) system, and to simulate the system by assuming that at each time step the configuration of the system is based on probabilities that items (e.g., individuals) of the system will act in a particular manner.

For example, one may assume that in a disease-transmission system, the locations of the individuals in the system at any time step depends on a respective probability for each individual that the individual will travel from on location to another location during the interval between the current time step and the immediately prior time step.

Figure 4:
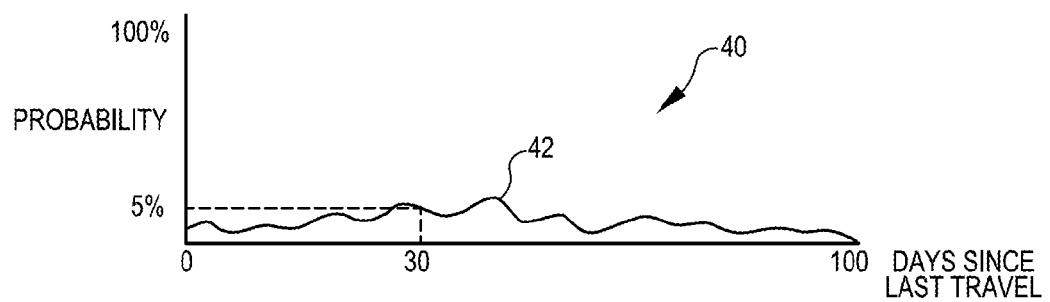
FIG. 4 is a plot of a probability that an individual will travel versus the time since the individual last traveled.

FIG. 4 is a plot 40 of a distribution of the probability that an individual will travel between the current and immediately prior time steps versus the number of days since the individual last traveled, where the area under the probability curve 42 equals one. For example, according to the curve 42, the probability that the individual will travel if it has been 30 days since he/she last traveled is approximately 5%.

Figure 5:
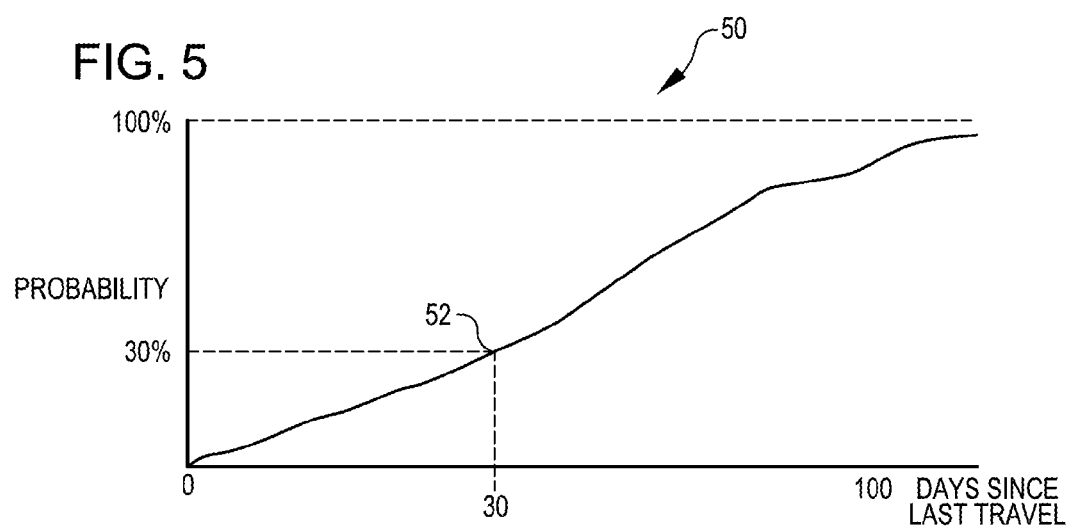
FIG. 5 is a plot of a probability that at least one individual in a region will travel by a particular time.

FIG. 5 is a plot 50 of a distribution of the probability that an individual will travel by any particular day from the day he/she last traveled, where the curve 52 is the integral of the curve 42 of FIG. 4; in some applications, the plot 50 may be more useful for system simulation than the plot 40. For example, the plot of FIG. 5 indicates that there is an approximately 30% chance that an individual will travel to a different location within the 30 days following the day he last travelled.

Referring to FIGS. 2 and 5, the simulator 22 may simulate the locations of individuals at any time step by simulating the migration of the individuals according to the probability curve 52. For example, focusing on a single individual who last traveled thirty days prior to a relative time step $t_0$, the simulator 22 generates a random number from 0-1, and from the random number determines whether the individual has traveled in the interval between $t_0$ and $t_1$. Because at thirty days the probability curve 52 indicates a probability of 30%, if the random number is less than or equal to 0.3, then the simulator 22 determines that the individual has traveled in the interval between $t_0$ and $t_1$; but if the random number is greater than 0.3, then the simulator 22 determines that the individual has not travelled in the interval between $t_0$ and $t_1$. The simulator 22 may simulate the movement of the remaining simulated individuals in a similar manner.

By simulating the movement of individuals and the actions of other system items in such a probabilistic manner, the simulator 22 simulates the system in one of the possible system configurations, where the simulator selects the simulated system configuration by randomly drawing from probability-distribution curves such as the curve 52 for individual migration. Such a technique is sometimes called a Monte Carlo technique, or a Monte Carlo based technique.

To simulate a statistically independent subset of all the possible system configurations, the simulator 22 may repeat the above procedure for a number of times (e.g., 100, 1,000, 10,000) that is sufficient to yield a statistically independent subset of system configurations. That is, the simulator 22 may "run" through the simulation with the same input-data and input-parameter values for a number of times that is sufficient to yield simulation results from a statistically independent subset of the possible system configurations.

The randomness involved in the simulator's selection of the system configurations to be simulated helps to insure statistical independence of the selected configurations, while the probability weighting of this randomness helps to insure that more weight is given to more likely configurations than to less likely configurations. For example, if the simulation period is ten years, it is very unlikely that none of the 100,000 individuals in a disease-transmission system will travel from one location to another during the simulation period. Therefore, although it is possible that the simulator 22 may randomly select such a configuration, the chances of this are much less likely than the chances that the simulator 22 will randomly select a configuration in which at least some of the individuals travel during the simulation period.

Referring to FIG. 2, as described above, depending upon the size of the simulated non-linear system and the computing power of the simulation tool 20, even a single run through a system simulation by the simulator 22 may consume a significant amount of execution time (e.g., a few minutes, a few hours, a few days, or even a few weeks).

And taking into account that the simulator 22 may execute multiple (e.g., 100, 1,000, 10,000) simulation runs to yield a statistically sufficient set of output signals 30 and output results 32 for a single set of input-data and input-parameter values, it may take a significant amount of time for one using the simulator to find a set of input-data and input-parameter values that corresponds to a sought-after result (e.g., a greater than 99% probability of disease elimination), or to determine that such a set of input values does not exist. For example, assume that the simulator 22 is simulating a disease-transmission system to determine if there is a range of percentages of the number of individuals vaccinated that will lead to elimination of a disease, and, if such a range exists, to find this range. Also assume that but for the input parameter 26 that represents the percentage of vaccination coverage, the values of the input-data signals 24 and the values of the other input-parameters 26 remain constant. To determine and identify such a range of the percentage of vaccination coverage, one may run the simulator 22 with a pre-selected number of different percentage-of-vaccination values, for example, one hundred percentage values from 1% to 100% in steps of one percent. One may see which of these percentage values corresponds to the highest probability of disease elimination, and then he/she may investigate some fractional percentages around this highest-probability percentage value to identify the boundaries of a range of percentage values that corresponds to a sought-after probability of elimination. But at perhaps 10,000 or more simulation runs per simulated percentage value, such a simulation protocol may take a significant amount of time. And if there are multiple significantly different percentages that yield a sought-after result, then one may decide to investigate fractional percentages around all of these different percentages to develop the boundaries of multiple ranges of suitable vaccination-percentage values. Furthermore, consider that value of more than one input parameter may be changeable (e.g., vaccination percentage, vaccination timing, and bed-net coverage), thus geometrically increasing the number of combinations of input-parameter values that may be simulated. Consequently, using such a methodical technique to hone in on a set of input-parameter values that corresponds to a sought-after result, or to determine that no such set of input-parameter values exists, may take an impractically long time.

Figure 6:
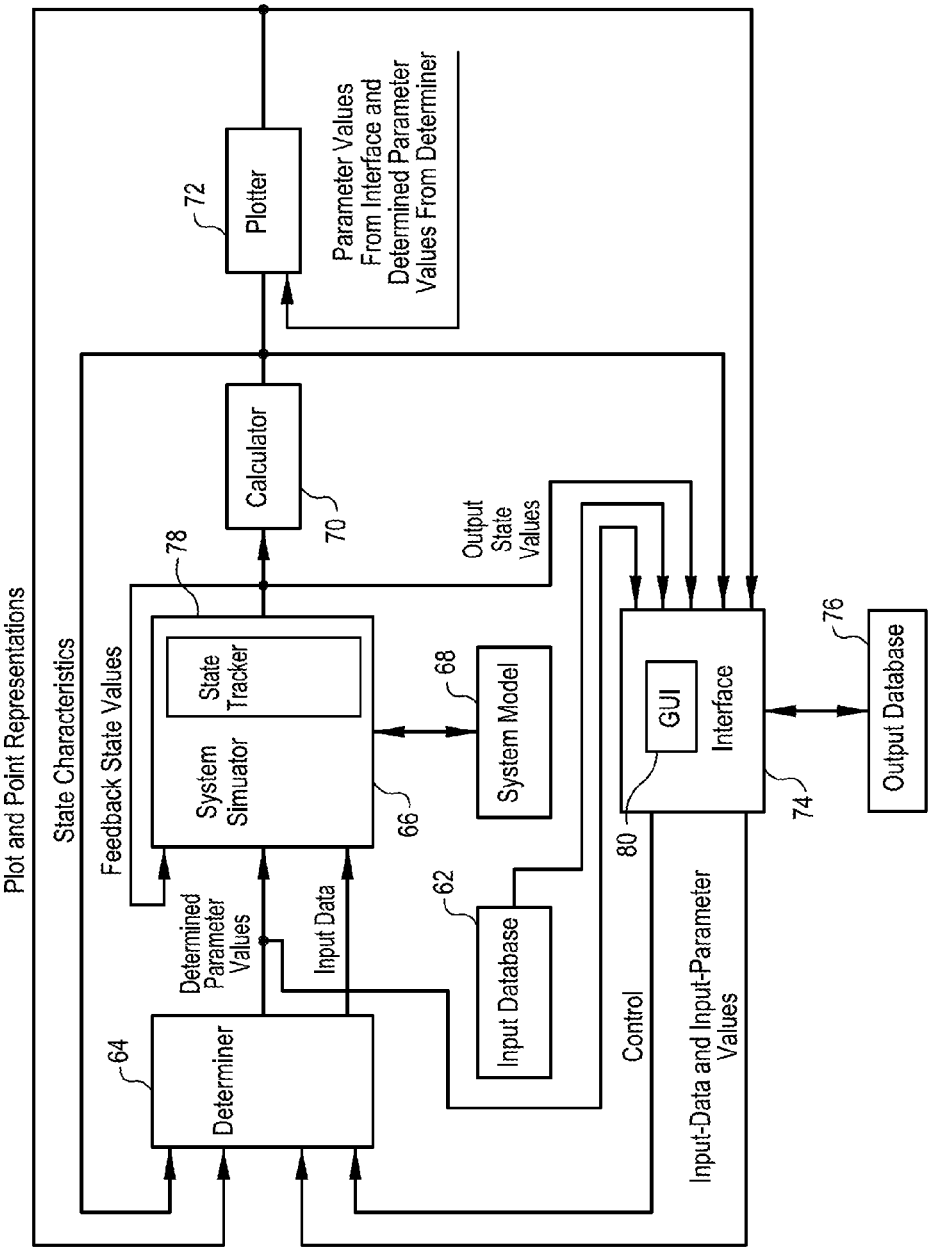
FIG. 6 is a block diagram of an embodiment of an apparatus/tool for simulating a stochastic system.

FIG. 6 is a block diagram of an embodiment of a simulation tool 60 that, compared to a conventional simulation tool, may decrease the time required to identify a set of input-parameter values that corresponds to a sought-after result, or may decrease the time required to determine that no such set of input-parameter values exists.

The simulation tool 60 includes an input database 62, a next-parameter-value determiner 64, a system simulator 66, a system model 68, a state-characteristic calculator 70, a plotter 72, an interface 74, and an output database 76. The simulator tool 60 may be installed on, or may include, a computing apparatus that is configured by software, firmware, hardware, or a combination or sub-combination of software, firmware, and hardware, to perform the functions of the simulation tool, including the functions of the input database 62, determiner 64, simulator 66, system model 68, calculator 70, plotter 72, interface 74, and output database 76. These and other components of the simulation tool 60 may be separately identifiable software or firmware modules or circuits, or they may be logical components of modules or circuits that perform the functions of more than one of these components. For example, the simulation tool 60 may include means for performing the functions of these and other tool components, and these means may be may be separately identifiable software or firmware modules or circuits, or they may be modules or circuits that perform the functions of more than one of these tool components.

The input database 62 stores input data regarding the system to be simulated, the conditions of the environment in which the system is disposed, and other quantities that may influence the system. For example, the input database 62 may store, e.g., topographical information, weather information, and sunrise/sunset information, for a geographical region. In an embodiment, the input database 62 may store data that an operator of the tool 60 does not wish to manipulate as an input parameter, e.g., because such data (e.g., topographical information) is fixed and not manipulatable in the real world.

The next-parameter-value determiner 64 determines a next value of one or more input parameters in a manner that, compared to a conventional simulation tool, allows the simulation tool 60 to hone in more quickly on a set of parameter values that corresponds to a sought-after result, or to determine more quickly that no such set of parameter values exists; for example, the determiner may allow the simulation tool to hone in on a set of parameter values, or to determine that no such set of values exists, with fewer simulation runs than a conventional simulation tool. The determiner 64 may determine such next-parameter values in response to one or more state-characteristic values from the calculator 70, and from the representations of one or more result-surface plots and one or more level sets (described below) from the plotter 72. The operation of the determiner 64 is described in more detail below in conjunction with FIGS. 10-27.

The system simulator 66 includes a state tracker 78, and, referring to FIG. 3, propagates the x states $S_0$-$S_{x-1}$ of the simulated system through time in z discrete steps $t_0$-$t_{z-1}$ in response to one or more input-data values and one or more input-parameter values from the determiner 64, and one or more output-state values fed back to the input of the simulator. The simulator 66 propagates the states S through time by determining the respective value that each state S has at each time step t in response to the system model 68. For example, for the simulation of a malaria-transmission system, the model 68 may define influences that environmental conditions or other quantities have on the number of infected individuals (a state of the simulated system) at a time t; examples of such conditions and quantities include the number of infected individuals at the previous time step t−1, the number of infected mosquitos at t−1, the temperature and rainfall at t−1, the bed-net coverage at t−1, the percentage of individuals vaccinated at t−1, and the migration of individuals during the interval between t−1 to t. And from these defined influences and the values of these system-influencing conditions and quantities, the simulator 66 may calculate the number of infected individuals at time t; for example, the higher the temperature and rainfall at t−1, the more infected mosquitos, and thus the more infected individuals, at t. The simulator 66 may calculate the values of the other states of the simulated system in a similar manner. Furthermore, the intervals between the steps t may be uniform, or they may vary if event-based timing is used. Moreover, although not shown in FIG. 3, the simulator 66 may propagate some of the states S through time in uniform time steps, and may, at least effectively, propagate other states S through time in event-based non-uniform time steps. The operation of the system simulator 66 is discussed in more detail below in conjunction with FIGS. 23-27 according to an embodiment.

The state tracker 78 keeps track of the current value of each state S of the simulated system. For example, if a state S is the number of individuals infected, then the state tracker 78 stores this number, which the simulator 66 updates at each time step. The state tracker is further described below in conjunction with FIGS. 7 and 8 according to an embodiment.

The system model 68 may include one or more microsimulations, and may include software, firmware, hardware, or a combination or sub-combination of software, firmware, and hardware, that defines a system to be simulated by the simulator 66. For example, for a malaria-transmission system, the system model 68 may stochastically define the system states, and may define system phenomena that affect the system states such as the migration patterns of individuals, the life cycle of a malaria parasite within a human host, the life cycle of a malaria parasite within a mosquito host, the life cycle of a mosquito, the interaction between individuals and mosquitos, and the infection of individuals by mosquitos and of mosquitos by individuals. The system model 68 may also stochastically define dependencies of such system phenomena on environmental conditions and other system-influencing quantities such as temperature, rainfall, humidity, the number of infected individuals at a time step, and the number of infected mosquitos at a time step.

The calculator 70 calculates one or more characteristics of, or one or more characteristics that are otherwise related to, one or more states S of the simulated system. For example, after a number of runs of the simulator 66 at a particular set of input-parameter and input-data values for a simulated disease-elimination campaign, the calculator 70 may calculate the probability that the simulated campaign eradicated the disease, i.e., the probability that at the end of the campaign period, the number of infected individuals (and for malaria, the number of infected mosquitos) is zero. The calculator 70 may also calculate the statistical variance of, or the statistical uncertainty in, this probability. The calculator 70 may make its calculation using any suitable function such as a Bayesian prior, a beta function or incomplete beta function, which are subsets of a Bayesian prior, or a binomial distribution, which is a subset of an incomplete beta function. The operation of the calculator 70 using a binomial distribution is further described below in conjunction with FIG. 9 according to an embodiment.

The plotter 72 generates representations of one or more plots based on one or more of the following: the values of one or more state characteristics from the calculator 70, one or more input-parameter values from the determiner 64 and the interface 74, and one or more state values output from the simulator 66—"representation" indicates that the plotter 72 need not generate an actual visual plot (although it may), but that it may instead generate a representation of a plot in, e.g., computer memory, which the simulator tool 60 includes or to which the simulator tool otherwise has access. Alternatively, the plotter 72 may receive the input-parameter values from one, not both, of the determiner 64 and interface 74. For example, the plotter 72 may generate a representation of an N-dimensional result surface having respective input parameters as N−1 of these dimensions, and having a state characteristic as the remaining dimension. As a more detailed example, assume that for a malaria-transmission system, an operator of the tool 60 is investigating the relationship among vaccination coverage (an input parameter), bed-net coverage (another input parameter), and the probability of eradicating malaria (a state characteristic). The plotter 72 may generate a representation of an N=3-dimensional result surface having vaccination coverage as a first dimension, bed-net coverage as a second dimension, and probability of elimination as a third dimension. The plotter 72 may also generate a representation of one or more level sets for this result surface, and the determiner 64 may use such a result surface and level set to determine a respective next value of the vaccination-coverage parameter, the bed-net use parameter, or of both of these parameters. Furthermore, the plotter 72 may generate other types of plots, such as a topographical plot of a region showing a time progression of the distribution of infected individuals within the region. Operation of the plotter 72, including the generation of result surfaces and level sets, is further described below in conjunction with FIGS. 10-22 according to an embodiment.

The interface 74 interfaces other components of the simulation tool 60 to each other, and includes a graphical user interface (GUI) 80, which allows an operator to configure and to use the simulation tool.

The interface 74 may also store in the output database 76 a "snap shot" of the values of the states S of the simulated system at each time step t of the simulation period. These snap shots may allow an operator to see the development of one or more states of the simulated system as the simulator 66 propagates these states through time, and may facilitate an operator's step-by-step analysis of a simulation run or an operator's step-by-step comparison of multiple simulation runs.

Furthermore, the interface 74 may store in the output database 76 for each simulation run the state characteristics generated by the calculator 70 and the representations of the spatial points and result surfaces generated by the plotter 72.

Moreover, the interface 74 may store in the output database 76 for each simulation run the set of input-data and input-parameter values provided to the simulator 66 for the simulation run. Because this set of input values, or a subset of this set of input values, may be the coordinates of a representation of a spatial point that is generated by the plotter 72, this set of input values is sometimes referred to as the "simulation point" of the simulation run. And an operator of the simulation tool 60 may be described as using the tool to find a simulation point that corresponds to a sought-after result. Furthermore, the interface 74 may provide this set of input values to the determiner 64 for a next simulation run that may use the same set, or a slightly modified set, of input values. Providing the set of input values from a prior simulation run to the determiner 64 may eliminate the need to re-enter, manually or otherwise, all of the input-data values from the input database 64 and all of the unmodified input-parameter values via the GUI 80.

In addition, the interface 74 and GUI 80 may allow a user to configure, control, or otherwise interact with the simulation tool 60.

Furthermore, the interface 74 may allow an operator to select input-data and input-parameter values to be input to the simulator 66. For example, if an operator would like to simulate a malaria-transmission system in Madagascar, then he/she may use the interface 74 to configure the simulation tool 62 such that Madagascar-relevant input data (e.g., weather-related data, population data) from the input database 62 is provided to the simulator 66.

Moreover, an operator may select via the interface 74 input parameters to be used in a simulation, and may also select values of these input parameters. For example, for simulating a malaria-transmission system, an operator may select vaccination coverage and bed-net coverage as input parameters, and may select initial values for these coverages.

In addition, an operator may configure the system model 68 via the interface 74. For example, there is more than one malaria parasite, and one parasite may behave differently under given conditions than another parasite. Therefore, an operator may configure the model 68 for a particular malaria parasite. Or, if individuals of one type (e.g., child vs. adult) react, on average, differently to a malaria parasite than individuals of another type, then an operator may provide the model 68 with the percentages of each type of individual in a region of interest (alternatively, these percentages may come from the input database 62).

Furthermore, an operator may configure the determiner 64 via the interface 74. For example, an operator may specify the parameter or parameters for which the determiner 64 will determine a next value after a set of simulation runs, and may also specify an algorithm or other criteria that the determiner uses to determine such next value(s). An example of such an algorithm is described below in conjunction with FIGS. 10-22 according to an embodiment.

Moreover, an operator may, via the interface 74, specify one or more state characteristics and configure the calculator 70 to generate the values of the specified one or more characteristics.

In addition, an operator may, via the interface 74, specify one or more plots and configure the plotter 72 to generate representations of the specified one or more plots.

Furthermore, an operator may configure, via the interface 74, the GUI 80 to display tool-generated quantities such as one or more state values from the simulator 66, one or more state-characteristic values from the calculator 70, or one or more plots from the plotter 72.

The output database 76 may store the state-value snapshots from the simulator 66, the state-characteristic values from the calculator 70, the representations of the points and plots from the plotter 72, and the sets of input-data and input-parameter values input to the simulator as described above, and may also store other data.

Still referring to FIG. 6, alternate embodiments of the simulation tool 60 are contemplated. For example, the system model 68 may be part of the system simulator 66.

Figure 7:
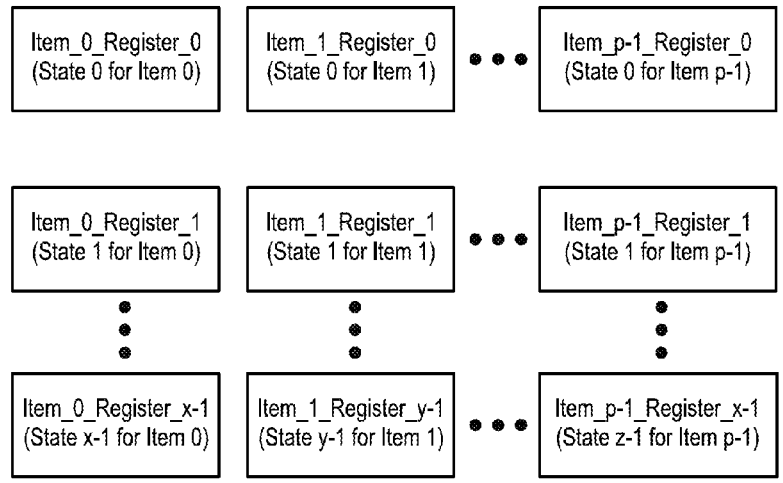
FIG. 7 is a block diagram of an embodiment of the state tracker of FIG. 6, where the state tracker tracks the states of a system model on a per-item basis.

FIG. 7 is a block diagram of an embodiment of the state tracker 78 (FIG. 6) for an embodiment of the system simulator 66 (FIG. 6) that tracks states S of a simulated system on a per-item basis, i.e., by the items that have one or more of the tracked states.

As discussed above in conjunction with FIG. 6, the simulated system includes items (e.g., individuals, mosquitos) each having one or more states S (e.g., infected, immune, vaccinated, item location).

The state tracker 78 saves the values of these states as the simulator 66 propagates these states through time, and updates the values of these states at each time step t.

To track states on a per-item basis, the state tracker 78 includes one set of memory locations for each item in the simulated system, where the number of memory locations in the set is the number of states S that the item may have; not all items need have the same number of states, and not all memory locations need be the same size. Each of such memory locations may be disposed in a respective state-memory register. Therefore, if there are p items included in the simulated system, then the state tracker 78 includes the following number of state registers:

Number of state registers=[$x$=the number of states $S$ for item__0]+[$y$=the number of states $S$ for item__1]+ . . . +[$z$=the number of states $S$ for item__$p$−1])    (1)

For example, assume that the system being simulated is a malaria-transmission system, item__0 is an individual of the simulated system, item__1 is a mosquito of the simulated system, each individual has the states "infected (yes/no)", "vaccinated (yes/no)", "location (identity of location)", and "recovered (yes/no)," and each mosquito has the states "infected (yes/no)" and "able to infect a human (yes/no)."

In this example, the state tracker 78 may include for item__0 and every other simulated individual three one-bit state registers for the states "infected," "vaccinated," and "recovered," and a multi-bit state register for "location" (assuming that there are more than two possible locations), and may include for item__1 and every other simulated mosquito two one-bit state registers for the states "infected" and "able to infect a human."

As discussed above in conjunction with FIG. 6, in an embodiment, at each time step t the simulator 66 updates the values of the states S stored in the registers of state tracker 78, and the interface 74 stores a snapshot of these state values in the output database 76 by loading the contents of the state-tracker registers into the output database.

Still referring to FIG. 7, alternate embodiments of the per-item state tracker 78 are contemplated. For example, instead of including a state register for each state of each simulated item, the tracker 78 may include one state register per item, where each state register includes a respective register location for each state of the item.

Figure 8:
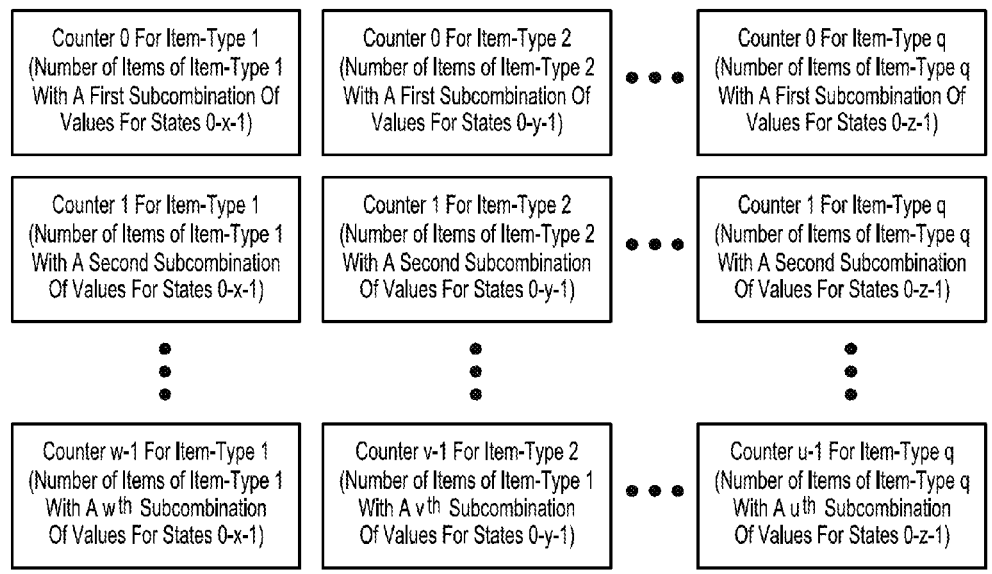
FIG. 8 is a block diagram of an embodiment of the state tracker of FIG. 6, where the state tracker tracks the states of a system model on a compartmentalized basis.

FIG. 8 is a block diagram of an embodiment of the state tracker 78 of FIG. 6 for an embodiment of the system simulator 66 (FIG. 6) that tracks the states S of a simulated system on a compartmentalized basis.

As discussed above in conjunction with FIGS. 6-7, the system simulator 66 simulates a system that includes items (e.g., individuals, mosquitos) each having one or more states S (e.g., "infected," "immune," "vaccinated," "location").

The state tracker 78 saves the values of these states as the simulator 66 propagates these states through time, and updates the values of these states at each time step t.

To track these states on a compartmentalized basis, the state tracker 78 includes one set of counters for each type of item modeled, where the number of counters in the set equals the number of possible combinations of state values that an item of the corresponding type may have; not all item types need have the same number of possible combinations of state values, and not all counters need be the same size. Each of such counters stores the number of items having the corresponding state-value combination, and may be configured as a conventional counter or as a respective memory register. Therefore, if there are q item types included in the system model, then the state tracker 78 includes the following number of state-value-combination counters:

Number of state-value-combination counters=[$w$=the number of possible state-value combinations for item_type_0]+[$v$=the number of possible state-value combinations for item_type_1]+ . . . +[$u$= the number of possible state-value combinations for item_type_$q$−1]     (2)

For example, suppose that the system being simulated is a malaria-transmission system, item_type_0 includes simulated individuals, item_type_1 includes simulated mosquitos, each individual has the states "infected (yes/no)", "vaccinated (yes/no)", "location (identity of one of three locations)", and "previously infected (yes/no)," and each mosquito has the states "infected (yes/no)" and "able to infect a human (yes/no)," where the possible values for each state are within the parentheses.

In this example, for each item in item_type_0, i.e., for each simulated individual, there are three states each having two possible values and one state having three possible values; therefore, each individual may have one of 2·2·2·3=24 possible state-value combinations at each time step t, and the state tracker 78 includes twenty four state-value counters for item_type_0. And, at each time step t, each counter stores the number of individuals having the corresponding state-value combination. For example, one possible state-value combination that an individual may have is "infected=yes", "vaccinated=yes", "location=Antananarivo, Madagascar", and "previously infected=yes;" therefore, the counter corresponding to this state-value combination updates and stores the number of individuals that have this combination of state values at each time step t.

Similarly, for each item in item_type_1, i.e., for each modeled mosquito, there are two states each having two possible values; therefore, each mosquito may have one of 2·2=4 possible state-value combinations at each time step t, and the state tracker 78 includes four state-value counters for item_type_1. And at each time step t, each counter updates and stores the number of mosquitos having the corresponding state-value combination. For example, one possible state-value combination that a mosquito may have is "infected=yes" and "able to infect a human=no;" therefore, the item_type_1 counter corresponding to this state-value combination updates and stores the number of mosquitos that have this combination of state values at each time step t.

At each time step t, after the simulator 66 updates the values of the counters, the interface 74 stores a snapshot of these counter values in the output database 76 by loading the contents of the counters into the output database as described above in conjunction with FIG. 6.

Still referring to FIG. 8, alternate embodiments of the compartmentalized state tracker 78 are contemplated. For example, instead of including one set of counters for each item type, the state tracker 78 may include one set of counters for each item type in each geographic location (this would allow one to omit location as a state for that item type) or other grouping. Furthermore, where the values of some states are mutually exclusive, this may reduce the number of possible combinations of state values, and thus may allow one to reduce or "prune" the number of counters in the state tracker 78. For example, for a disease-transmission system, if a state of a simulated individual state is "infected," and another state is "recovered," then both of these states for an individual may not simultaneously have a value of "yes"; therefore, there may be no need for the state tracker 78 to include a counter for any state-value combination where the values of both of these states is "yes".

Referring to FIGS. 7-8, in an embodiment, whether to implement a per-item state tracker 78 or a compartmentalized state tracker may depend on the system being simulated. For example, if the simulated system includes a relatively small number of items, then a per-item state tracker 78 may occupy less memory than a compartmentalized state tracker; conversely, if the simulated system includes a relatively large number of items, then a compartmentalized state tracker 78 may occupy less memory than a per-item state tracker.

Figure 9:
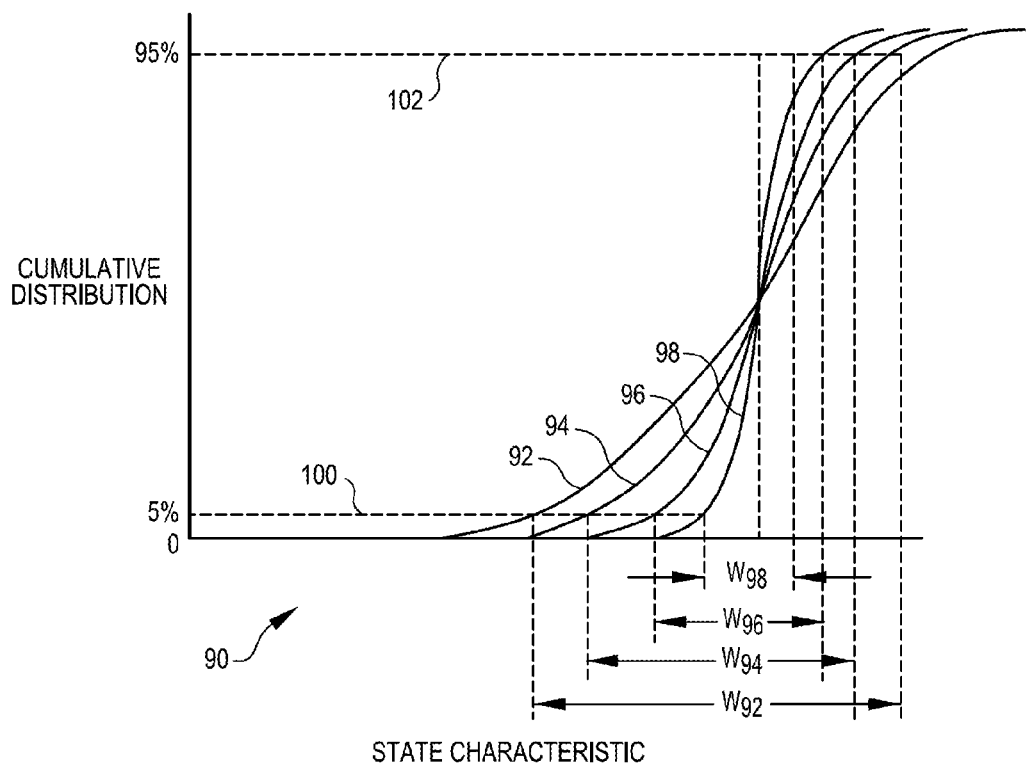
FIG. 9 is a plot of binomial distributions for a state characteristic.

FIG. 9 is a plot 90 of a cumulative distribution function that, in an embodiment, yields binomial-distribution curves 92-98, which the calculator 70 of FIG. 6 may generate and may use to calculate a state-characteristic value in response to one or more corresponding state values from the simulator 66, where the state-characteristic value represents a probability.

The cumulative distribution is the dimension along the vertical axis of the plot 90, and the state characteristic is the dimension along the horizontal axis. For example, the state characteristic may be the probability of disease-elimination by the end of an elimination-campaign period, where the corresponding state is the number of infected individuals at the end of the campaign period.

In an example where the state characteristic is the probability of successful elimination, the calculator 70 generates a representation of the curve 92 from the number of successful eliminations and the number of unsuccessful eliminations over a number of simulation runs at a set of input-data and input-parameter values (i.e., at a simulation point). The curve 92 has a mean equal to r, which is the value of the state characteristic, and, has a width $w_{92}$ between, for example, its 5% height 100 and its 95% height 102. The plotter 72 may generate a representation of the curve 92 suitable for display via the GUI 80 (FIG. 6).

The curve 94, a representation of which the calculator 70 generates from the numbers of elimination successes and failures over a greater number of simulation runs than from which it generates the representation of the curve 92, also has a mean equal to r and has a width $w_{94}$ between its 5% height and 95% height.

Similarly, the curve 96, a representation of which the calculator 70 generates from the numbers of elimination successes and failures over a greater number of simulation runs than from which it generates the representation of the curve 94, also has a mean equal to r, and has a width $w_{96}$; and the curve 98, a representation of which the calculator generates from the numbers of elimination successes and failures over a greater number of simulation runs than from which it generates the representation of the curve 96, also has a mean equal to r, and has a width $w_{98}$.

Consequently, the more simulation runs on which a binomial-distribution curve is based, the narrower its width w.

Furthermore, a binomial-distribution curve's width w is proportional to the statistical uncertainty in, the standard deviation σ of, and the statistical variance $σ^2$ of, the value r of the state characteristic; therefore, in general, the greater the number of simulation runs on which a binomial-distribution curve is based, the lower the statistical uncertainty in, and the smaller the standard deviation σ and the variance $σ^2$ of, r. Statistical uncertainty is dependent on the standard deviation and the variance, and may be expressed as a function of one or both of the standard deviation and variance. For example, if r=99.5% probability of success, the standard deviation σ=√10.15%, and the variance $σ^2$=0.15%, then the statistical uncertainty in r may be expressed as ±√0.15% if the statistical uncertainty is expressed as a function of σ, or may be expressed as ±0.15% if the statistical uncertainty is expressed as a function of $σ^2$.

Therefore, an operator of the simulation tool 60 may configure the system simulator 66 to generate a number of simulation runs per each simulation point sufficient to yield the state-characteristic value r having a statistical uncertainty that is less than an uncertainty threshold, and having a standard deviation σ that is less than a standard-deviation threshold or having a variance $σ^2$ that is less than a variance threshold.

Referring to FIGS. 6 and 9, operation of an embodiment of the calculator 70 is described for an example where the modeled system is a disease-transmission system and the state characteristic is the probability of successful disease elimination at the end of the elimination-campaign period at a single simulation point.

First, the simulator 66 runs a number, e.g., 100, 1,000, 10,000, of simulations of the modeled system at the simulation point. A result that each of these simulations yields is a respective number of infected individuals at the end of the elimination campaign, where the respective number either equals zero (successful elimination) or does not equal zero (unsuccessful elimination campaign).

Next, the calculator 70 labels as successes all simulation runs yielding a number of infected individuals equal to 0, and labels as failures all simulation runs yielding this number not equal to zero. For example, the number of successes may be represented by a and the number of failures may be represented by b such that a+b equals the number of simulations runs.

Then, from a and b, the calculator 70 calculates the probability of success=mean r=a/(a+b), and generates a representation of a binomial-distribution curve, such as one of the curves 92-98, according to one or more known equations. Furthermore, an operator may configure the tool 60 such that plotter 72 and GUI 80 cause the curve to be displayed on a display device that may be part of, or coupled to, the GUI.

Next, from the representation of the binomial-distribution curve, the calculator 70 calculates the statistical uncertainty in, and the standard deviation σ or variance $σ^2$ of, the probability of success r.

Then, the calculator 70 compares the statistical uncertainty and standard deviation or variance to respective thresholds that a user may have entered via the GUI 80. If either the uncertainty or standard deviation/variance is greater than its corresponding threshold, then the calculator 70 may instruct the simulator 66 to run additional simulations at the corresponding simulation point in an effort to reduce the uncertainty and/or standard deviation/variance below the corresponding thresholds, or may instruct the plotter 72 to ignore this simulation point when generating or updating a result surface (generating and updating a result surface are described below). Alternatively, if the uncertainty and standard deviation/variance are less than or equal to the corresponding thresholds, then the calculator 70 may pass the probability of success and the identity of the simulation point to the plotter 72 for use in generating or updating a result surface as described below.

Still referring to FIGS. 6 and 9, in an embodiment, the calculator 70 may calculate one or more categories of uncertainty other than statistical uncertainty, and may represent these other categories as respective state characteristics, or may generate one or more state characteristics that each represent a combination of two or more of these uncertainty categories. Conventional algorithms may be used for generating values for other categories of uncertainty such as those described below, and for combining these values. Furthermore, the calculator 70 may compare one or more of these uncertainty values to one or more respective thresholds, and may instruct the simulator 66 to run additional simulations at the corresponding simulation point in an effort to reduce these one or more uncertainties below the corresponding thresholds, or may instruct the plotter 72 to ignore this simulation point when generating or updating a result surface. Alternatively, if the one or more uncertainty values are less than or equal to the corresponding thresholds, then the calculator 70 may pass the probability of success and the identity of the simulation point to the plotter 72 for use in generating or updating a result surface.

Stochastic uncertainty is a measure of the uncertainty in a particular simulation result. For example, suppose that the result is the number of individuals who are infected at the end of an elimination campaign. If all of the simulations yield numbers of remaining infected individuals between 0-10, then the stochastic uncertainty that the number of remaining infected individuals is no more than 10 is relatively low. But the stochastic uncertainty that the number of remaining infected individuals is no more than five may depend on the probability distribution of the number of remaining infected individuals between 1 and 10. The stochastic uncertainty may be independent of the probability of success. For example, if all simulation runs yield a number of remaining infected individuals being either 1 or 2, then the stochastic uncertainty in the number of remaining infected individuals is relatively low, but the current estimate of the probability of success in eradicating the disease is zero because no simulations yield zero remaining infected individuals. The calculator 70 may conventionally calculate a value of stochastic uncertainty.

Parameter uncertainty is a measure of the uncertainty of a simulation result based on the uncertainty in input data or in an input parameter. For example, it may not be accurately known in what percentage of individuals a vaccine is effective in inducing immunity to a disease. So even if the vaccination coverage (i.e., the percentage of individuals vaccinated) is accurately known, there may be uncertainty in the number of individuals that the vaccination makes immune. If a simulation result such as the number of individuals infected at the end of an elimination-campaign period is sensitive to the number of individuals made immune by vaccination, then the uncertainty in the effectiveness of the vaccine may impart a significant uncertainty to the calculated value of the probability of successful elimination of the disease. But an operator may use the simulation tool 60 to simulate and account for the possible effect of parameter uncertainty on a simulation result. For example, he/she may simulate a wide range of vaccination coverage under the assumption that all vaccinations induce immunity, and see to what range of immunity percentages the disease elimination is sensitive. For example, if vaccination-induced immunity of 60% or greater corresponds to a sought-after probability of success that is relatively insensitive to small changes in the value of vaccination-induced immunity, and it is known that conservatively, the vaccine induces immunity in 90% of individuals, then vaccination coverage of about 67% or greater corresponds to the sought-after probability of successful elimination even if 10% of the vaccinated individuals do not become immune. Using the simulation tool 60 to simulate the possible effects of parameter uncertainty on a simulation result is further described below in conjunction with FIGS. 20-21 according to an embodiment. Furthermore, the calculator 70 may calculate a value of parameter uncertainty.

Coverage uncertainty is the uncertainty in whether a particular intervention will be utilized. For example, if a malaria-elimination campaign calls for issuing bed nets to all children under 10 years old, then the uncertainty is a measure of how many of these children will actually receive a bed net, and how many of the children receiving a bed net will actually use it. A value for coverage uncertainty may be determined empirically from actual data (e.g., distribute bed nets to children and see how may children receive and use them), and an operator may effectively input this value to the simulation tool 60 (FIG. 6) so that the simulator 66 may account for it in simulations. For example, he/she may simulate a wide range of bed-net coverage under the assumption that all distributed bed nets will be used, and see to what bed-net coverage percentages disease elimination is sensitive. For example, if bed-net coverage of 50% or greater corresponds to a sought-after probability of successful elimination that is relatively insensitive to small changes in the value of bed-net coverage, and it is known that conservatively, 90% of children to whom a bed net is distributed will receive and use the bed net, then bed-net coverage of about 56% or greater corresponds to the sought-after probability of successful elimination even if 10% of the children to whom a bed net is distributed do not receive or use it. Using the simulation tool 60 to simulate the possible effects of coverage uncertainty on a simulation result is further described below in conjunction with FIGS. 20-21 according to an embodiment. Furthermore, the calculator 70 may calculate a value of coverage uncertainty.

Model-assumption uncertainty is the uncertainty in a simulation outcome caused by an uncertainty in an assumption built into the system model 68 (FIG. 6). Model-assumption uncertainty is similar to parameter and coverage uncertainty, but it may be difficult to account for in simulations without the ability to modify the system model. For example, for a malaria-transmission system, the model 68 may assume that a mosquito must live at least ten days before it is able to infect a human. But a simulation result such as probability of successful elimination of malaria may be sensitive to a variation in the minimum number of days that a mosquito must live before being able to infect a human. Without the ability to change this number of days in the model, an operator may be unable to investigate the sensitivity of the probability of successful elimination to this number of days as described above for parameter and coverage uncertainty. Therefore, the model 68 may be designed to allow an operator of the simulation tool 60 to vary one or more model assumptions so that he/she may determine a set of input-parameter values that correspond to a sought-after result even if a model assumption is at a worst-case value. Furthermore, the calculator 70 may calculate a value of model-assumption uncertainty.

Still referring to FIG. 9, alternate embodiments of the calculator 70 are contemplated. For example, the calculator 70 may pass the state-characteristic value r and corresponding simulation point to the plotter 72 regardless of the uncertainty in, or standard deviation/variance of, r. Furthermore, because a cumulative distribution function is a type of beta function, which is a type of Bayesian prior, instead of calculating a cumulative distribution function of a state-characteristic-probability value r to yield a binomial-distribution curve, the calculator 70 may calculate a representation of another type of beta function or Bayesian prior of r. Moreover, although described as calculating a probability, the calculator 70 may calculate a state-characteristic value other than a probability, and may do so using a function other than a cumulative distribution function. In addition, instead of comparing the one or more uncertainties in, and the standard deviation/variance of, r to respective thresholds, the calculator 70 may compare only one or none of the one or more uncertainties and standard deviation/variance to a respective threshold; furthermore, the calculator may analyze r in a manner that does not even involve uncertainty, standard deviation, or variance.

Figure 10:
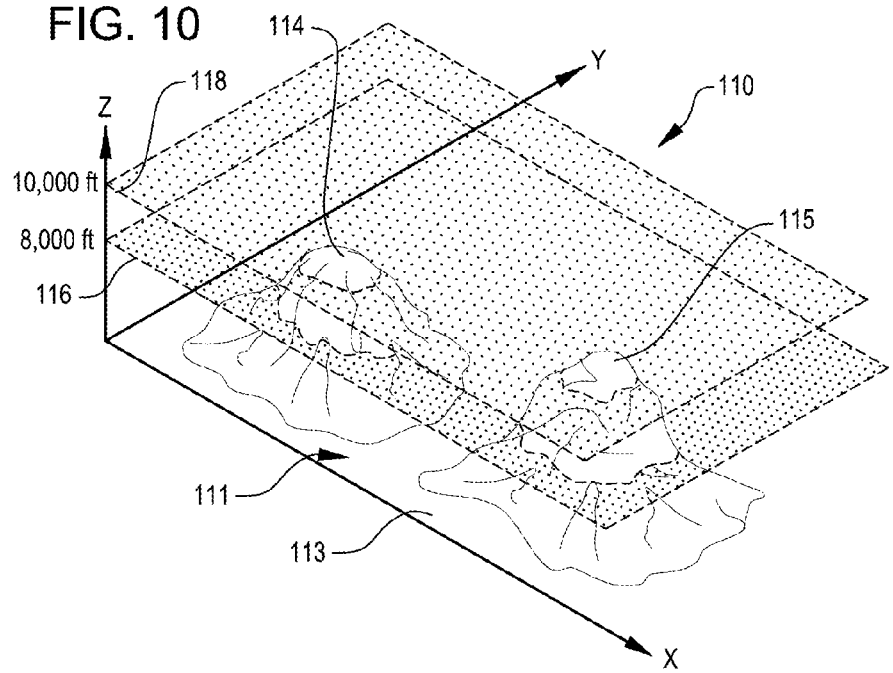
FIG. 10 is a topological plot of a land mass.

FIG. 10 is a plot 110 of a three-dimensional topographical map 111, which is used to explain an embodiment of a level set. The x and y axes respectively represent longitude and latitude, and the z axis represents altitude (z=0 is sea level).

Figure 11:
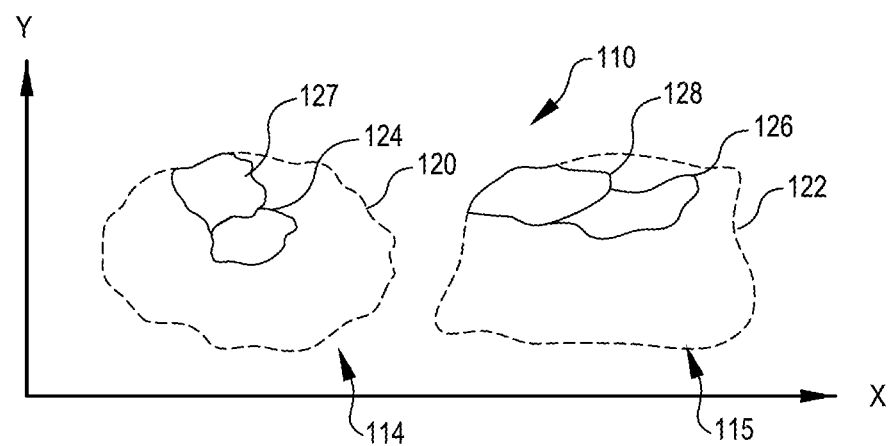
FIG. 11 is a plan view of the plot of FIG. 10.

FIG. 11 is a plan view of the plot 110 of FIG. 10 in the x-y plane.

Referring to FIGS. 10 and 11, the map 111 is of a landmass 113 having two mountains 114 and 115.

Suppose one would like an indication of the following: 1) the portions (if any) of the landmass 113 having an altitude greater than 10,000 feet, 2) the portions (if any) of the landmass having an altitude greater than 8,000 feet, 3) the portions (if any) of the landmass having an altitude between 8,000 feet and 10,000 feet, and 4) the portions (if any) of the landmass having an altitude between 8,000 and 10,000 feet with a slope in the z dimension of at least 25°.

Referring to FIG. 10, one way to generate such an indication is to insert into the map 111 an imaginary plane 116 at z=8,000 feet and another imaginary plane 118 at z=10,000.

Referring to FIG. 11, the dashed curves 120 and 122 represent the intersection of the 8,000-foot plane 116 with the landmass 111 at the mountains 114 and 115, the solid curves 124 and 126 represent the intersection of the 10,000-foot plane 120 with the landmass at the mountains, and the curves 127 and 128 (which include portions of the curves 120 and 124, and 122 and 126, respectively) represent the portions of the mountains having slopes of at least 25° between the 8,000- and 10,000-foot planes.

Consequently, the portions of the landmass 113 within the curves 124 and 126 are at altitudes greater than 10,000 feet, the portions of the landmass within the curves 120 and 122 are at altitudes greater than 8,000 feet, the portions of the landmass between the pairs of curves 120, 124 and 122, 126 are at altitudes between 8,000 and 10,000 feet, and the portions of the landmass within the curves 127 and 128 are at altitudes between 8,000 and 10,000 feet and have slopes of 25° or more.

Therefore, the points of the landmass 113 that form the curves 124 and 126 may be collectively referred to as a 10,000-foot "level set;" that is, the 10,000-foot level set is the set of points of the landmass at the 10,000-foot level. Furthermore, the points of the landmass 113 within, i.e., bounded by, the curves 124 and 126 may be referred to as a 10,000-foot "level-set region;" that is, the 10,000-foot level-set region is the set of points of the landmass above the 10,000-foot level.

Similarly, the points of the landmass 113 that form the curves 120 and 122 may be collectively referred to as an 8,000-foot level set, the points of the landmass between the curve pairs 120,124 and 122,126 may be referred to as an 8,000-10,000-foot level-set region, the curves 127 and 128 may be referred to as a 8,000-10,000-foot-with-25°-slope boundary, and the points of the landmass within the curves 127 and 128 may be referred to as the 8,000-10,000-foot-with-at-least-25°-slope region. Furthermore, notice that, for example, the 10,000-foot level-set region is within the 8,000 level-set region such that one level-set region may include another level-set region, and a level set may bound more than one level-set region.

Moreover, the collection of all level sets that may appear as part of the topographical map 111, or that one may otherwise use in conjunction with the topographical map, may be referred to as a "separatrix" of the map. For example, the altitude curves or contours that appear on a topographical map collectively form an altitude separatrix of the map, and the depth curves or contours that appear on a depth chart of a body of water collectively form a depth separatrix of the chart. Technically, a topographical map may include an infinite number of level sets, although only a small subset of these level sets may be identified or otherwise used.

Referring to FIGS. 12-22, embodiments of the following are described: a technique for generating a representation of an initial version of a result surface, examples of result surfaces, a technique for generating a representation of a level set relative to a result surface, a technique for selecting a next value of one or more input parameters in response to representations of a result surface and a level set, and a technique for updating a representation of a result surface and a representation of a level set.

A result surface is an N-dimensional surface (N may be greater than, equal to, or less than two) having P dimensions that are respective input parameters and having SC dimensions that are state-characteristics such that N=P+SC.

For example, where the simulation tool 60 (FIG. 6) is simulating a malaria-transmission system, the plotter 72 may generate a representation of a result surface having the following N=3 dimensions: vaccination coverage, bed-net coverage (both input parameters), and probability of successful elimination of malaria at the end of the campaign period (state characteristic).

Figure 12:
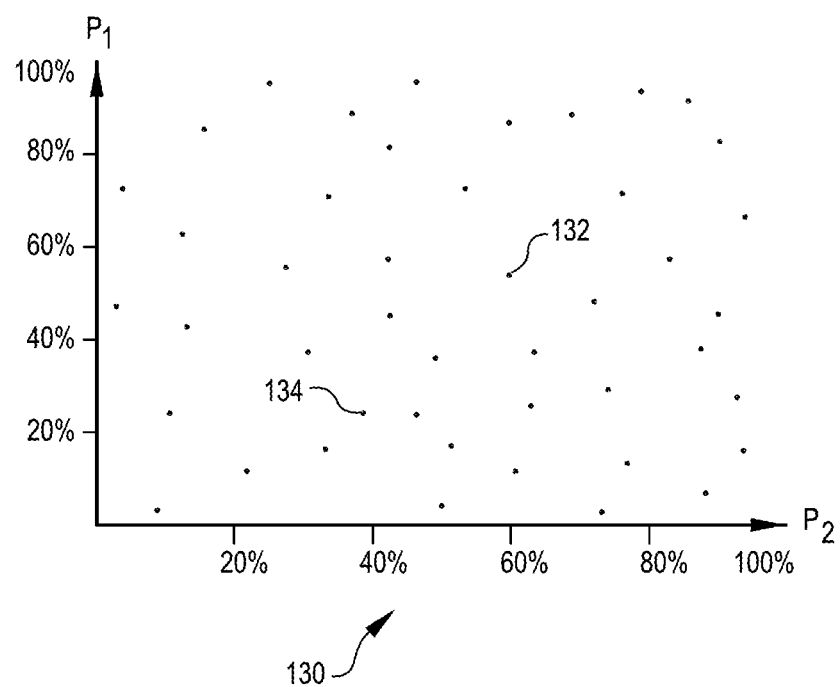
FIG. 12 is a plot of initial parameter points that are randomly generated by an embodiment of the determiner of FIG. 6.

FIG. 12 is a plan view of a plot 130 of simulation points having coordinates that the determiner 64 (FIG. 6) may randomly generate, and from which the plotter 72 (FIG. 6) may generate a representation of an initial version of an N=3-dimensional result surface.

For example purposes, the plot 130 is described as having a first dimension $P_1$ corresponding to malaria-vaccination coverage, a second dimension $P_2$ corresponding to bed-net coverage, and a third dimension SC (normal to the $P_1$-$P_2$ plane) corresponding to the probability of successful malaria elimination, where each of these dimensions has possible values ranging from 0% to 100%.

To reduce the processing time and complexity involved in generating and updating a representation of a result surface, the plot 130 may not include all of the dimensions of a simulation point. For example, a simulation point may include, in addition to $P_1$, $P_2$, and SC, other dimensions that correspond to input-data values and input-parameter values that the simulation tool 60 (FIG. 6) holds constant during a simulation; examples of such held-constant input values include, e.g., the average temperature and the average rain fall for a region. But because the values of these other dimensions are held constant for the simulation, the plotter 72 may omit these dimensions from the representation of the plot 130, e.g., in an effort to simplify the plotter's generating and updating of the representation of the result surface.

Therefore, if the plot 130 includes fewer dimensions than a simulation point, then one may refer to the points of the plot as "partial" simulation points, and may refer to the result surface, a representation of which the plotter 72 (FIG. 6) generates from these partial simulation points, as a "partial" result surface.

Conversely, if the plot 130 includes all of the dimensions of a simulation point, then one may refer to the points of the plot as "full" simulation points, and may refer to the result surface, a representation of which the plotter 72 (FIG. 6) generates from these full simulation points, as a "full" result surface.

Referring to FIGS. 6 and 12, in operation, an embodiment of the determiner 64 receives from the interface 74 input-data values and input-parameter values for any input parameters other than vaccination coverage and bed-net coverage, where these input-data and parameter values may have been previously entered or otherwise selected by an operator via the GUI 80 as discussed above in conjunction with FIG. 6.

The determiner 64 also randomly generates a respective value for each of the vaccination coverage (dimension $P_1$) and bed-net coverage (dimension $P_2$).

Next, the determiner 64 provides the input-data and input-parameter values (including the randomly generated values for vaccination and bed-net coverage) forming the simulation point to the system simulator 66.

Then, the simulator 66 runs, at this simulation point, a number (e.g., 100, 1,000, 10,000) of simulations sufficient for the calculator 70 to yield a probability of success (dimension SC) having one or more uncertainties and standard deviation/variance that are each less than a respective threshold.

Next, the plotter 72 receives the values of the vaccination coverage and bed-net coverage (i.e., dimensions $P_1$ and $P_2$) from the determiner 64, receives the value of the probability of successful elimination (i.e., dimension SC) from the calculator 70, and generates a representation of the plot 130 including a point 132 at coordinates corresponding to the received values of $P_1$, $P_2$, and SC.

Then, the determiner 64 receives from the interface 74 the same input-data values and the same other input-parameter values (i.e., the values of all input parameters except vaccination coverage and bed-net coverage) that the simulator 66 used for the last simulation run (i.e., the simulation tool 60 holds these input values constant), and randomly generates a respective next value for each of the vaccination coverage (dimension $P_1$) and bed-net coverage (dimension $P_2$).

Next, the determiner 64 provides the input-data and input-parameter values forming a next simulation point to the simulator 66, which runs, at this next simulation point, a number of simulations sufficient for the calculator 70 to yield a probability of success (dimension SC) having one or more uncertainties and standard deviation/variance that are each less than a respective threshold.

Then, the plotter 72 updates the representation of the plot 130 to include a next point 134 in addition to the previous point 132, where the point 134 has coordinates corresponding to the received next values of $P_1$, $P_2$, and SC.

The determiner 64, simulator 66, calculator 70, and plotter 72 repeat the sequence described in the preceding three paragraphs until the representation of the plot 130 includes a number of randomly generated points sufficient for the plotter 72 to generate a representation of an initial version of a result surface (not shown in FIG. 12) having the dimensions $P_1$, $P_2$, and SC. In FIG. 12, the random positioning of the points of the plot 130 in the $P_1$-$P_2$ plane results from the determiner 64 randomly generating the values for vaccination coverage (dimension $P_1$) and bed-net coverage (dimension $P_2$).

The plotter 72 may generate the representation of the initial version of the result surface according to a number of techniques. For example, the plotter 72 may use a conventional curve-fitting algorithm to generate, as the representation of the initial version of the result surface, a representation of a surface that best fits the points of the plot 130. Furthermore, the number of randomly generated points that is sufficient for the plotter 72 to generate the representation of the initial result surface may depend, e.g., on the surface-generating technique used. For example, a number of points ≥N, e.g., 10, 100, 1,000, or 10,000 may be sufficient for the plotter 72 to generate a representation of an initial result surface.

Examples of result surfaces are described below in conjunction of with FIGS. 14-22.

Figure 13:
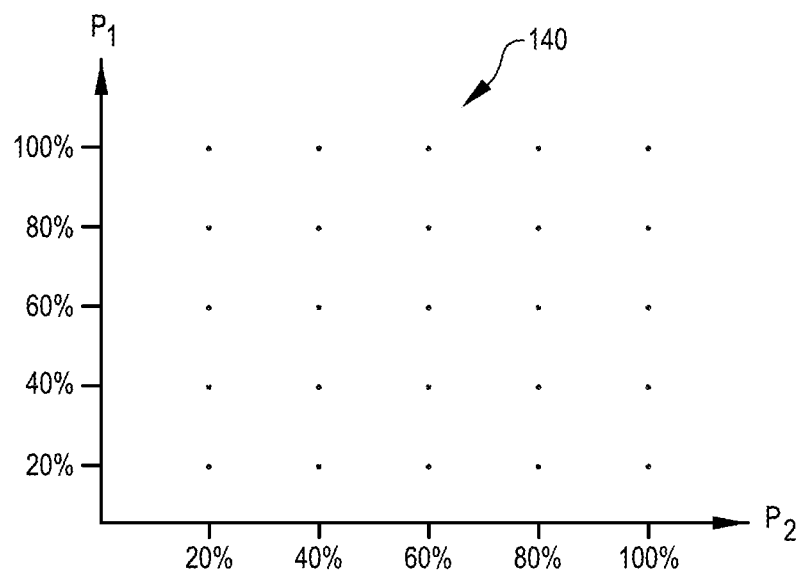
FIG. 13 is a plot of initial parameter points that are systematically generated by an embodiment of the determiner of FIG. 6.

FIG. 13 is a plan view of a plot 140 of simulation points that have coordinates that the determiner 64 (FIG. 6) may methodically generate, and from which the plotter 72 (FIG. 6) may generate a representation of an initial version of an N=3-dimensional result surface. In an embodiment, the determiner 64 methodically generates the points of the plot 140 according to a grid pattern.

Referring to FIGS. 6 and 13, assuming that the plot 140 has the same dimensions as the plot 130 of FIG. 12 (i.e., $P_1$=vaccination coverage, $P_2$=bed-net coverage, SC=probability of successfully eradicating malaria), the determiner 64, calculator 70, and plotter 72 operate as described above in conjunction with FIG. 12 such that the plotter generates a representation of an initial version of an N=3-dimensional result surface, except that instead of randomly selecting the values for vaccination coverage and bed-net coverage, the determiner methodically selects these values according to a grid pattern. For example, the determiner 64 may select values of vaccination coverage and bed-net coverage that yield points in the $P_1$-$P_2$ plane at the following ($P_1$, $P_2$) coordinates: (20%, 20%), (20%, 40%), (20%, 60%), . . . , (40%, 20%), (40%, 40%), (40%, 60%), . . . , (100%, 100%)—the determiner may select these pairs of $P_1$, $P_2$ values in any order. These points form a five-point-by-five-point grid, where adjacent points are equidistant from one another in the $P_1$ and $P_2$ dimensions.

Referring to FIGS. 12 and 13, alternate embodiments of a technique for generating a representation of an initial result surface are contemplated. For example, the determiner 64 (FIG. 6) may generate the input-parameter values according to techniques other than the random and methodical techniques described above in conjunction with FIGS. 12 and 13, respectively. Furthermore, the plotter 72 may generate a representation of an initial result surface having fewer or more than N=3 dimensions. Moreover, an initial result surface may include as dimensions input-data quantities and input parameters that remain constant throughout the simulation. In addition, regardless of the number N of dimensions of a result surface, the determiner 64 may generate values for fewer or more than two of these N dimensions.

Figure 14:
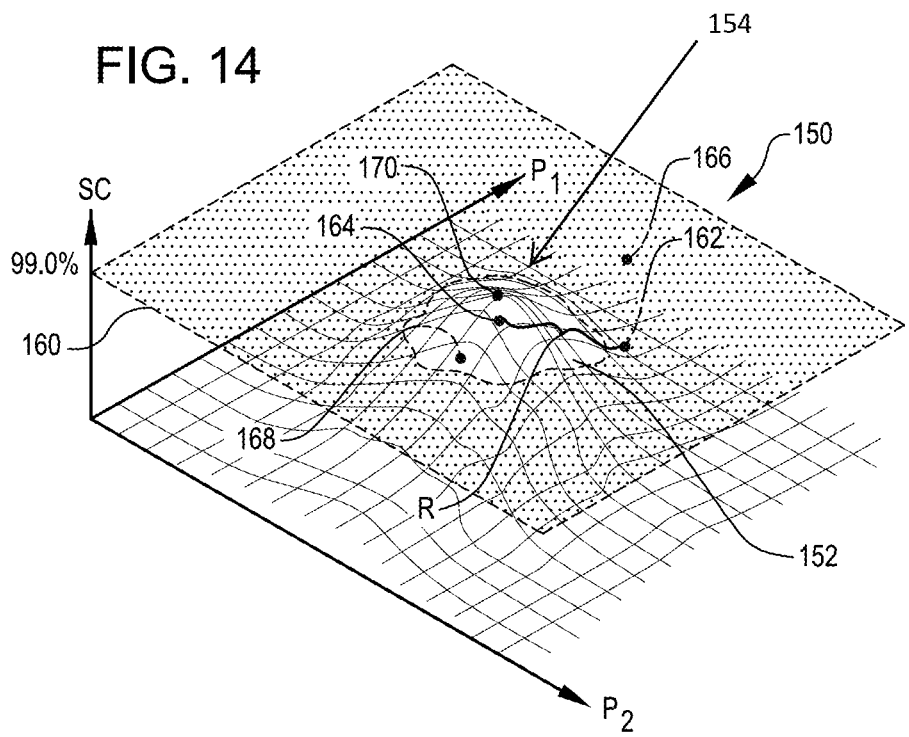
FIG. 14 is a plot of a simulation-result surface generated by an embodiment of the plotter of FIG. 6, where the surface includes a peak that extends to and above a state-characteristic threshold.

FIG. 14 is a plot 150 of an N=3-dimensional result surface 152, which includes a peak 154; as described above, the plotter 72 (FIG. 6) may generate a representation of the result surface 152, and the interface 74 (FIG. 6) may convert this representation into a form suitable for displaying the plot 150 of the result surface via the GUI 80 (FIG. 6).

Figure 15:
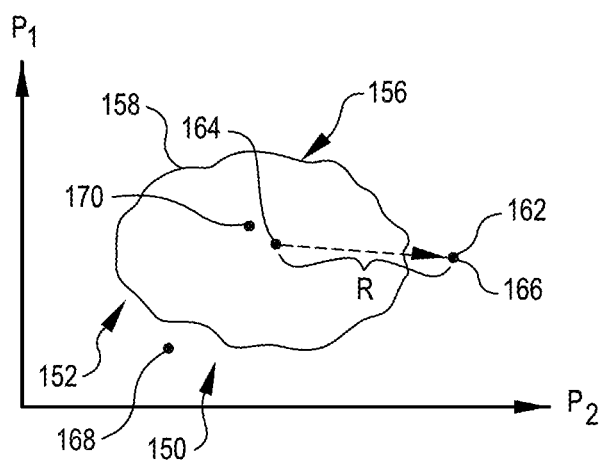
FIG. 15 is a top plan view of the plot of FIG. 14.

FIG. 15 is a plan view of the plot 150, result surface 152, a level-set region 156, and a level set 158.

As described below, the determiner 64 may determine a next value of an input parameter in response to the peak 154 and the level set 158 when an operator of the simulation tool 60 (FIG. 6) is searching for a value of the input parameter that corresponds to a sought-after result, such as a sought-after state characteristic, that is higher than a particular threshold represented by the level set 158.

For example, assume that the tool 60 (FIG. 6) is simulating a malaria-transmission system, the dimensions of the result surface 152 are $P_1$=vaccination coverage, $P_2$=bed-net coverage, and SC=probability of successfully eliminating malaria from a region, and an operator of the simulation tool 60 is desirous of discovering what, if any, values of $P_1$ and $P_2$ yield a value of SC greater than or equal to 99.0%.

Therefore, the plotter 72 (FIG. 6) determines if there is a level set at 99.0% that includes at least one point of the result surface 152. Conceptually, the plotter 72 may generate a representation of an imaginary plane 160 at SC=99.0% that is parallel with the $P_1$-$P_2$ plane, and any portions of the result surface 152 that are level with this plane form the 99.0% level set.

In this example, there are portions of the peak 154 of the result surface 152 that are level with and higher than the imaginary plane 160, and these portions respectively form a 99.0% level set 158 and a 99% level-set region 156, where the level set 158 is the intersection of the imaginary plane 160 with the result surface 152.

Referring to FIGS. 6, 14, and 15, operation of an embodiment of the determiner 64, simulator 66, calculator 70, and plotter 72 is described in conjunction with the result surface 152 and level set 158.

In an effort to further define the portions of the result surface 150 that form the level set 158 and the level-set region 156, the determiner 64 selects next values of vaccination coverage $P_1$ and bed-net coverage $P_2$ for simulation in response to the level set 158. For example, the determiner 64 may randomly select a point 162 of the plot 150 that is within a particular radial distance R from a reference point 164 of the result surface 152 within the level-set region 156, and the $P_1$ and $P_2$ coordinates of this randomly selected point 162 are the next values of vaccination coverage and bed-net coverage, respectively. The particular values for the radial distance R and the reference point 164 of the result surface 152 from which the radial distance R is measured may be selected by an operator of the tool 60 via the GUI 80. For example, the radial distance R may be $\sqrt{N}$, and the reference point 164 of the result surface 152 from which the radial distance R is measured may be the center of mass of the portion of the result surface within the level-set region 156. It is noted that neither the randomly selected point 162 nor the reference point 164 need lie on the result surface 152, although one or both points may lie on the result surface. Where the randomly selected point 162 lies on the result surface 152, a simulation using the $P_1$ and $P_2$ coordinates of the randomly selected point is typically not a "wasted" situation, because it is unlikely that the simulator 66 has simulated the $P_1$ and $P_2$ coordinates of the randomly selected point before. This is because, as described above, the plotter 72 may generate a representation of the result surface 152 from a relatively small number of points (as compared to the infinite number of points that form the result surface); therefore, there may be a good chance that the randomly selected point 162 is not one of the points from which the plotter previously generated the representation of the current result surface.

Consequently, instead of haphazardly selecting next values of the vaccination coverage and bed-net coverage, the determiner 64 selects the next values for these parameters in a methodical manner that may reduce the overall number of simulation points that the tool 60 needs to simulate before finding a range of values of the vaccination coverage and bed-net coverage that corresponds to the sought-after result of a 99.0% chance of successful malaria elimination. That is, by selecting the next values of vaccination coverage and bed-net coverage from near the level set 158, the determiner 64 may avoid a "wild goose chase" of next values that are unlikely to yield a probability of eradicating malaria that is 99.0% or better.

Still referring to FIGS. 6, 14, and 15, the determiner 64 then passes these next values of vaccination coverage and bed-net coverage, along with the values of any other input data and input parameters that define a full simulation point, to the simulator 66, which runs a number of simulations sufficient to allow the calculator 70 to yield a value of the probability of success having one or more uncertainties and standard deviation/variance within respective thresholds, for example, as described above in conjunction with FIG. 9.

Next, the plotter 72 generates a representation of a next point 166 of the plot 150 having coordinates ($P_1$, $P_2$, SC) respectively equal to the next values of the vaccination coverage and bed-net coverage selected by the determiner 64, and to the next value of the probability of success calculated by the calculator 70. Consequently, although the next point 166 has the same $P_1$ and $P_2$ coordinates as the point 162, it almost certainly will have a different SC coordinate than the point 162. Furthermore, it is noted that the point 162 is not actually part of the plot 150, but is shown in FIGS. 14 and 15 for purposes of explanation; therefore, the plotter 72 does not use the point 162 to update the result surface 152.

Then, the interface 74 saves the representation of the next plot point 166 of the plot 150 in the output database 76; that is, the interface saves all of the input-data and input-parameter values, i.e., the full simulation point, that yielded the next plot point 166, and also stores the SC value of this plot point. Note that the coordinates of the full simulation point are the same as N−1 coordinates of the next plot point 166, but the point 166 has an additional coordinate SC.

Next, the determiner 64 uses the level set 158 to select next values of the vaccination coverage ($P_1$) and bed-net coverage ($P_2$), and the simulator 66, calculator 70, and plotter 72 repeat their respective above-described operations, which result in a representation of a next point 168 of the plot 150.

The determiner 64, simulator 66, calculator 70, and plotter 72 continue to repeat their above-described operations until the plotter has generated a number of next plot points. An operator of the simulation tool 60 may select this number, which may be greater than or equal to one, via the interface 74.

Then, the plotter 72 updates the representation of the result surface 152 using the previously calculated points of the plot 150 (the points that the plotter used to generate the representation of the pre-updated version of the result surface) in combination with the next plot points just calculated. For example, the plotter 72 may use a curve-fitting algorithm to determine the updated result surface as a surface that best fits this combination of plot points. Therefore, because the plotter 72 uses all previously generated points of the plot 150 to update the representation of the result surface 152, the result surface typically becomes a more accurate indicator of the simulation results as the number of simulation points that the simulator 66 simulates increases. The plotter 72 may also update the location of the reference point 164 in response to the updated result surface.

Next, the plotter 72 updates the 99.0% level-set region 156 and level set 158 based on the representation of the updated result surface 152—because the result surface is updated, it may have a different shape than shown in FIGS. 14 and 15.

Then, the determiner 64, simulator 66, calculator 70, and plotter 72 repeat the above procedure until the iterations of the result surface 152 have sufficiently converged to a final result surface that is sufficient to allow an operator to select the values of vaccination coverage and bed-net coverage that he/she feels are the best values for actual implementation. For example, an operator may visually monitor the changes from updated result surface to updated result surface via the GUI 80, and instruct, via the interface 74, the determiner 64, simulator 66, calculator 70, and plotter 72 to repeat the above procedure until he/she feels that the result surface as sufficiently converged toward a final form. Or, an operator may configure the simulation tool 60, via the interface 74, to monitor the changes from updated result surface to updated result surface (e.g., to monitor the entropy of the result surface), and to halt the above procedure when the change from updated result surface to updated result surface is below an operator-selected surface-change threshold.

After obtaining a final result surface 152, or a representation thereof, from the simulation tool 60, an operator may select the values of the vaccination coverage and the bed-net coverage to be used in an actual malaria-elimination campaign from a point of the plot 150 that is on or off the final result surface 152. For example, an operator may select as the values of vaccination coverage and bed-net coverage the respective $P_1$ and $P_2$ coordinates of a peak point 170 within the level-set region 156 because this peak point has the highest value of the SC coordinate, and thus has the highest probability of successful eradication. Or, an operator may select as the values of vaccination coverage and bed-net coverage the respective $P_1$ and $P_2$ coordinates of a point that is not on the result surface 152, but that is near to a point of the result surface within the level-set region 156 or on the level set 158.

Still referring to FIGS. 6, 14, and 15, alternate embodiments of the above-described next-value-determination-and-result-surface-updating technique are contemplated. For example, although described in conjunction with the simulation of a malaria-transmission system, an embodiment of the technique may be applicable to the simulation of other disease-transmission systems and of non-disease-transmission systems. Furthermore, although described in conjunction with a single level set and single level-set region, an embodiment of the technique is compatible with the use of multiple level sets, multiple level-set regions, or both multiple level-sets and multiple level-set regions. Moreover, an embodiment of the technique is compatible with input parameters other than vaccination coverage and bed-net coverage, and with one or more state characteristics other than probability of successful malaria elimination. In addition, although the reference point 164 is described as being within the level-set region 156 in the $P_1$ and $P_2$ dimensions, the reference point may be located outside of the level-set region in the $P_1$ and $P_2$ dimensions.

Figure 16:
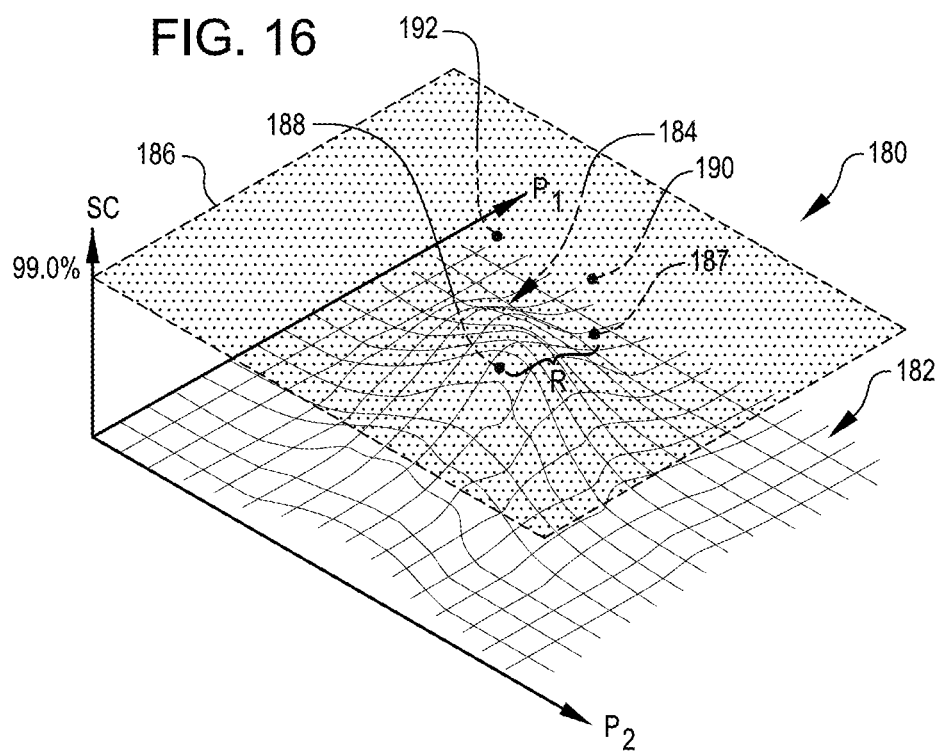
FIG. 16 is a plot of another simulation-result surface generated by an embodiment of the plotter of FIG. 6, where the surface includes peak that does not extend to or above a state-characteristic threshold.

FIG. 16 is a plot 180 of an N=3-dimensional result surface 182, which includes a peak 184; as described above, the plotter 72 (FIG. 6) may generate a representation of the result surface, and the interface 74 (FIG. 6) may convert this representation into a form suitable for displaying the plot of the result surface via the GUI 80 (FIG. 6).

Referring to FIGS. 6 and 16, in an example that is similar to that described above in conjunction with FIGS. 14-15, assume that the simulation tool 60 is simulating a malaria-transmission system, the dimensions of the result surface 182 are $P_1$=vaccination coverage, $P_2$=bed-net coverage, and SC=probability of successfully eliminating malaria from a region, and an operator of the simulation tool is desirous of discovering what, if any, values of $P_1$ and $P_2$ yield a value of SC greater than or equal to 99.0%.

Therefore, the plotter 72 (FIG. 6) determines if there is a level set at 99.0% that includes at least one point of the result surface 182. Conceptually, the plotter 72 may generate a representation of an imaginary plane 186 at SC=99.0% that is parallel with the $P_1$-$P_2$ plane, and any portions of the result surface 182 that are level with this plane form the 99.0% level set.

But in this example, unlike the example described above in conjunction with FIGS. 14-15, there are no portions of the peak 184 of the result surface 182 that are level with or higher than the imaginary plane 186; therefore, there is no 99.0% level set.

Referring to FIGS. 6 and 16, operation of an embodiment of the determiner 64, simulator 66, calculator 70, and plotter 72 is described in conjunction with the result surface 182.

In an effort to determine whether a 99.0% level set exists, the determiner 64 selects next values of vaccination coverage $P_1$ and bed-net coverage $P_2$ for simulation in response to the peak 184. For example, the determiner 64 may randomly select a point 187 of the plot 180 that is within a particular radial distance R from a reference point 188 of the peak 184, and the $P_1$ and $P_2$ coordinates of this randomly selected point 187 are the next values of vaccination coverage and bed-net coverage, respectively. The particular values for the radial distance R and the reference point 188 of the result surface 182 from which the radial distance R is measured may be selected by an operator of the simulation tool 60 via the GUI 80. For example, the radial distance R may be $\sqrt{N}$, and the reference point 188 of the result surface 182 may be the center of mass of the peak 184. It is noted that neither the randomly selected point 187 nor the reference point 188 need lie on the result surface 182, although one or both points may lie on the result surface. Where the randomly selected point 187 lies on the result surface 182, a simulation using the $P_1$ and $P_2$ coordinates of the randomly selected point is typically not a "wasted" situation for reasons similar to those described above in conjunction with FIGS. 14-15.

Consequently, instead of haphazardly selecting next values of the vaccination coverage and bed-net coverage, the determiner 64 selects the next values for these parameters in a methodical manner that may reduce the overall number of points that the tool 60 needs to simulate in order to determine whether there exist values of the vaccination coverage and bed-net coverage that yield the sought-after result of at least a 99.0% chance of successful malaria elimination. That is, by selecting the next values of vaccination coverage and bed-net coverage from nearby the peak 184, the determiner 64 may avoid a "wild goose chase" of next values that are unlikely to yield information as to whether there exist next values that yield a probability of eradicating malaria that is 99.0% or better.

Still referring to FIGS. 6 and 16, the determiner 64 then passes to the simulator 66 these next values of vaccination coverage and bed-net coverage, along with the values of any other input data and other input parameters that, together with the next values of vaccination and bed-net coverage, define a full simulation point.

Then, the simulator 66 runs a number of simulations sufficient to allow the calculator 70 to yield a value of the probability of success having one or more uncertainties and standard deviation/variance within respective thresholds as described above in conjunction with FIG. 9.

Next, the plotter 72 generates a representation of a next point 190 of the plot 180 having coordinates ($P_1$, $P_2$, SC) respectively equal to the next values of the vaccination coverage and bed-net coverage selected by the determiner 64, and to the next value of the probability of success calculated by the calculator 70. Although the next point 190 and point 187 have the same $P_1$ and $P_2$ coordinates, they almost certainly have different SC coordinates. Furthermore, the point 187 is not a point of the plot 180 that the plotter 72 will use to update the result surface 182, but is shown in FIG. 16 for purposes of explanation.

Then, the interface 74 saves the representation of the next point 190 of the plot 180 in the output database 76; that is, the interface saves the full coordinates (including input-data and other input-parameter values that are not dimensions of the plot 180) of the next point 190 in the output database.

Next, the determiner 64 selects next values of the vaccination coverage ($P_1$) and bed-net coverage ($P_2$) nearby the peak 184, and the simulator 66, calculator 70, and plotter 72 repeat their respective above-described operations, which result in the plotter generating a representation of a next point 192 of the plot 180.

The determiner 64, simulator 66, calculator 70, and plotter 72 continue to repeat their above-described operations until the plotter has generated a number of next plot points. An operator of the simulation tool 60 may select this number, which may be greater than or equal to one, via the interface 74.

Then, the plotter 72 generates a representation of an updated result surface 182 using the previously calculated points of the plot 180 (the points that the plotter used to generate the pre-updated version of the result surface) in combination with the next plot points just calculated. For example, the plotter 72 may use a curve-fitting algorithm to determine the representation of the updated result surface as a representation of a surface that best fits this combination of plot points. And the plotter 72 may also update the location of the reference point 188.

Next, the plotter 72 evaluates the representation of the updated result surface 182 and determines whether a 99.0% level set exists—because the result surface is updated, it may have a different shape than shown in FIG. 16.

If no 99.0% level set exists, then, the determiner 64, simulator 66, calculator 70, and plotter 72 repeat the above procedure until the iterations of the result surface 182 result in a 99% level set, or have sufficiently converged to a final result surface that is sufficient to indicate that no 99% level set is likely to exist. For example, an operator may visually monitor the changes from updated result surface to updated result surface via the GUI 80, and instruct, via the interface 74, the determiner 64, simulator 66, calculator 70, and plotter 72 to repeat the above procedure until a 99% level set exists, or until he/she feels that the result surface as sufficiently converged toward a final form sufficient to indicate that a 99% level set is unlikely to exist. Or, an operator may configure the interface 74 to monitor the changes from updated result surface to updated result surface (e.g., to monitor the entropy of the result surface), and to halt the above procedure when either a 99% level set is discovered or the change from updated result surface to updated result surface is below an operator-selected threshold.

If a 99% level set is found, then the determiner 64, simulator 66, calculator 70, and plotter 72 may revert to an embodiment of the procedure described above in conjunction with FIGS. 14-15.

If no 99% level set is found, then an operator may "tweak" one or more values of the input data and input parameters, other than vaccination coverage and bed-net coverage, that form the full simulation point, or an operator may take other action such as using the simulation tool 60 to simulate interventions other than vaccination coverage and bed-net coverage.

Still referring to FIGS. 6 and 16, alternate embodiments of the above-described next-value-determination-and-result-surface-updating technique where no sought-after level set exists (at least initially) are contemplated. For example, alternate embodiments described above in conjunction with FIGS. 14-15 may also be compatible with an embodiment described in conjunction with FIG. 16. Furthermore, although described as searching for the existence of a single level set, an embodiment of the technique may search for multiple level sets.

Figure 17:
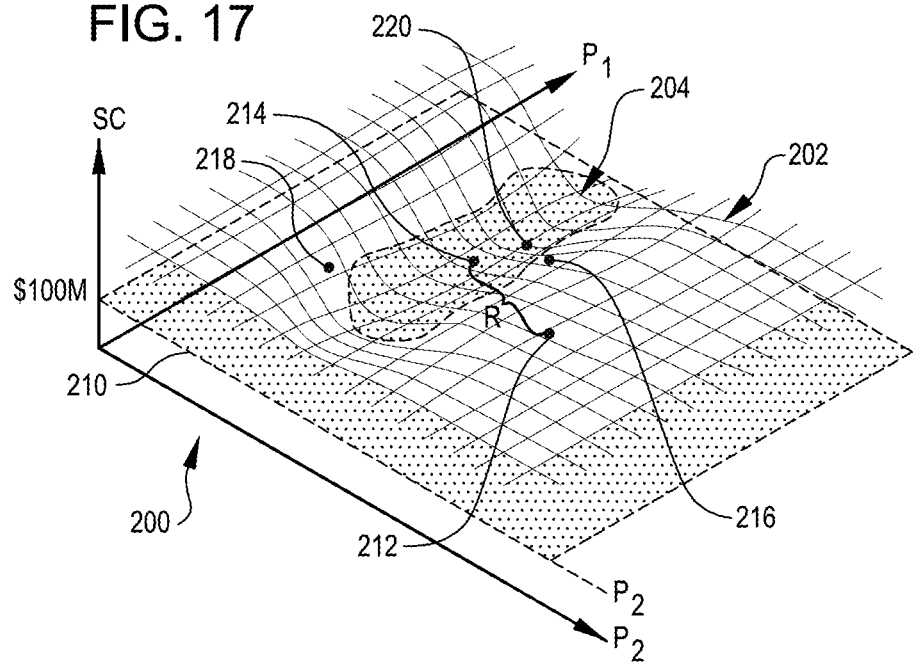
FIG. 17 is a plot of a simulation-result surface generated by an embodiment of the plotter of FIG. 6, where the surface includes a valley that extends to and below a state-characteristic threshold.

FIG. 17 is a plot 200 of an N=3-dimensional result surface 202, which includes a valley 204; as described above, the plotter 72 (FIG. 6) may generate a representation of the result surface, and the interface 74 (FIG. 6) may convert this representation into a form suitable for displaying the plot of the result surface via the GUI 80 (FIG. 6).

Figure 18:
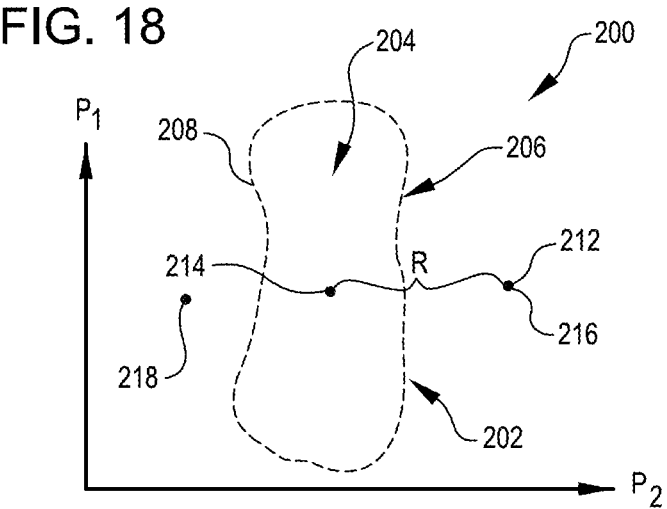
FIG. 18 is a top plan view of the plot of FIG. 17.

FIG. 18 is a plan view of the plot 200, result surface 202, valley 204, a level-set region 206, and a level set 208.

Referring to FIGS. 6, 17, and 18, as described below, the determiner 64 may determine a next value of an input parameter in response to the valley 204 and the level set 208 when an operator of the simulation tool 60 is searching for a value of the input parameter that corresponds to a sought-after result, such as a sought-after state characteristic, that is lower than a particular threshold represented by the level set 208.

For example, assume that the simulation tool 60 is simulating a malaria-transmission system, the dimensions of the result surface 202 are $P_1$=vaccination coverage, $P_2$=bed-net coverage, and SC=the average cost of providing the vaccination coverage and bed-net coverage, and an operator of the simulation tool is desirous of discovering what, if any, values of $P_1$ and $P_2$ yield a value of SC less than US$100,000,000 ($100 M). In this example, the system model 68 (FIG. 6) may define a state $S_1$=cumulative cost of the vaccination coverage over the campaign period and a state $S_2$=cumulative cost of the bed-net coverage over the campaign period; therefore, SC equals the average of $S_1+S_2$ over all simulation runs at a particular simulation point.

Consequently, the plotter 72 determines whether there is a level set at $100 M that includes at least one point of the result surface 202. Conceptually, the plotter 72 may generate a representation of an imaginary plane 210 at SC=$100 M that is parallel with the $P_1$-$P_2$ plane, and any portions of the result surface 202 that are level with this plane form the $100 M level set.

In this example, there are portions of the valley 204 of the result surface 202 that are level with and lower than the imaginary plane 210, and these portions respectively form the $100 M level set 208 and the $100 M level-set region 206, where the level set 208 is the intersection of the imaginary plane 210 with the result surface 202.

Referring to FIGS. 6, 17, and 18, operation of an embodiment of the determiner 64, simulator 66, calculator 70, and plotter 72 is described in conjunction with the result surface 202, level-set region 206, and level set 208.

In an effort to further define the portions of the result surface 200 within the level-set region 206 and that form the level set 208, the determiner 64 selects next values of vaccination coverage $P_1$ and bed-net coverage $P_2$ for simulation in response to the level set 208. For example, the determiner 64 may randomly select a point 212 of the plot 200 that is within a particular radial distance R from a reference point 214 of the result surface 202 within the level-set region 206, and the $P_1$ and $P_2$ coordinates of this randomly selected point 212 are the next values of vaccination coverage and bed-net coverage, respectively. The particular values for the radial distance R and the reference point 214 of the result surface 202 from which the radial distance R is measured may be selected by an operator of the tool 60 via the GUI 80. For example, the radial distance R may be $\sqrt{N}$, and the reference point 214 may be the center of mass of the portion of the result surface within the level-set region 206. It is noted that neither the randomly selected point 212 nor the reference point 214 need lie on the result surface 202, although one or both of these points may lie on the result surface. Where the randomly selected point 212 lies on the result surface 202, a simulation using the $P_1$ and $P_2$ coordinates of the randomly selected point is typically not a "wasted" situation for reasons similar to those described above in conjunction with FIGS. 14-15.

Consequently, instead of haphazardly selecting next values of the vaccination coverage and bed-net coverage, the determiner 64 selects the next values for these parameters in a methodical manner that may reduce the overall number of simulation points that the tool 60 needs to simulate before finding values of the vaccination coverage and bed-net coverage that correspond to the sought-after result of a cost of $100 M or less for vaccinations and bed nets. That is, by selecting the next values of vaccination coverage and bed-net coverage from within the level-set region 206 or nearby the level-set region or level set 208, the determiner 64 may avoid a "wild goose chase" of next values that are unlikely to yield a cost of no more than $100 M for vaccinations and bed nets.

Still referring to FIGS. 6, 17, and 18, the determiner 64 then passes these next values of vaccination coverage and bed-net coverage, along with the values of any input data and any other input parameters that define a full simulation point, to the simulator 66, which runs a number of simulations sufficient to allow the calculator 70 to yield a value of the vaccination-and-bed-net-coverage cost having one or more uncertainties and standard deviation/variance within respective thresholds, for example, as described above in conjunction with FIG. 9.

Next, the plotter 72 generates a representation of a next point 216 of the plot 200 having coordinates ($P_1$, $P_2$, SC) respectively equal to the next values of the vaccination coverage and bed-net coverage selected by the determiner 64, and to the next value of the vaccination and bed-net cost calculated by the calculator 70. Although the points 212 and 216 have the same $P_1$ and $P_2$ coordinates, they almost certainly have a different SC coordinate. Furthermore, the point 212 is not a point that the plotter will use to update the result surface 202, but this point is shown in the plot 200 for example purposes.

Then, the interface 74 saves the representation of the next point 216 of the plot 200 in the output database 76; that is, the interface saves in the output database all of the input-data and input-parameter values that yielded the next point 216, as well as the SC coordinate of this next point.

Next, the determiner 64 uses the level set 208 to select next values of the vaccination coverage ($P_1$) and bed-net coverage ($P_2$), and the simulator 66, calculator 70, and plotter 72 repeat their respective above-described operations, which results in the plotter generating a representation of a next point 218 of the plot 200.

The determiner 64, simulator 66, calculator 70, and plotter 72 continue to repeat their above-described operations until the plotter has generated a number of next plot points. An operator of the tool 60 may select this number, which may be greater than or equal to one, via the interface 74.

Then, the plotter 72 updates the result surface 202 using the previously calculated points of the plot 200 (the points that the plotter used to generate the pre-updated version of the result surface) in combination with the next plot points just calculated. For example, the plotter 72 may use a curve-fitting algorithm to generate a representation of the updated result surface equal to a representation of a surface that best fits this combination of plot points. The plotter 72 may also update the location of the reference point 214.

Next, the plotter 72 generates representations of the updated $100 M level-set region 206 and updated level set 208 based on the representation of the updated result surface 202—because the result surface is updated, it may have a different shape that shown in FIGS. 17-18.

Then, the determiner 64, simulator 66, calculator 70, and plotter 72 repeat the above procedure until the iterations of the updated result surface 202 have sufficiently converged to a final result surface that is sufficient to allow an operator to select the values of vaccination coverage and bed-net coverage that he/she feels are the best values for actual implementation. For example, the operator may visually monitor the changes from updated result surface to updated result surface via the GUI 80, and instruct, via the interface 74, the determiner 64, simulator 66, calculator 70, and plotter 72 to repeat the above procedure until he/she feels that the result surface has sufficiently converged toward a final form. Or, an operator may configure the interface 74 to monitor the changes from updated result surface to updated result surface (e.g., to monitor the entropy of the result surface), and to halt the above procedure when the change from updated result surface to updated result surface is below an operator-selected threshold.

An operator may select the values of the vaccination coverage and the bed-net coverage for implementation in an actual malaria-elimination campaign from a point of the plot 200 that is on or off the result surface 202. For example, an operator may select as these values of vaccination coverage and bed-net coverage the respective $P_1$ and $P_2$ coordinates of a valley point 220 within the level-set region 206 because this valley point has the lowest value of the SC coordinate, and thus has the lowest average cost of vaccinations and bed nets. Or, an operator may select as these values of vaccination coverage and bed-net coverage the respective $P_1$ and $P_2$ coordinates of a point that is not on the result surface 202, but that is near to a point of the result surface within the level-set region 206 or on the level set 208.

Still referring to FIGS. 6, 17, and 18, alternate embodiments of the above-described next-value-determination-and-result-surface-updating technique are contemplated. For example, alternate embodiments described above in conjunction with FIGS. 14-16 may be applicable to the technique described above in conjunction with FIGS. 17-18. Moreover, an embodiment of the technique described above in conjunction with FIGS. 17-18 may be useful for sought-after results other than a cost of a disease intervention being below a cost threshold.

Figure 19:
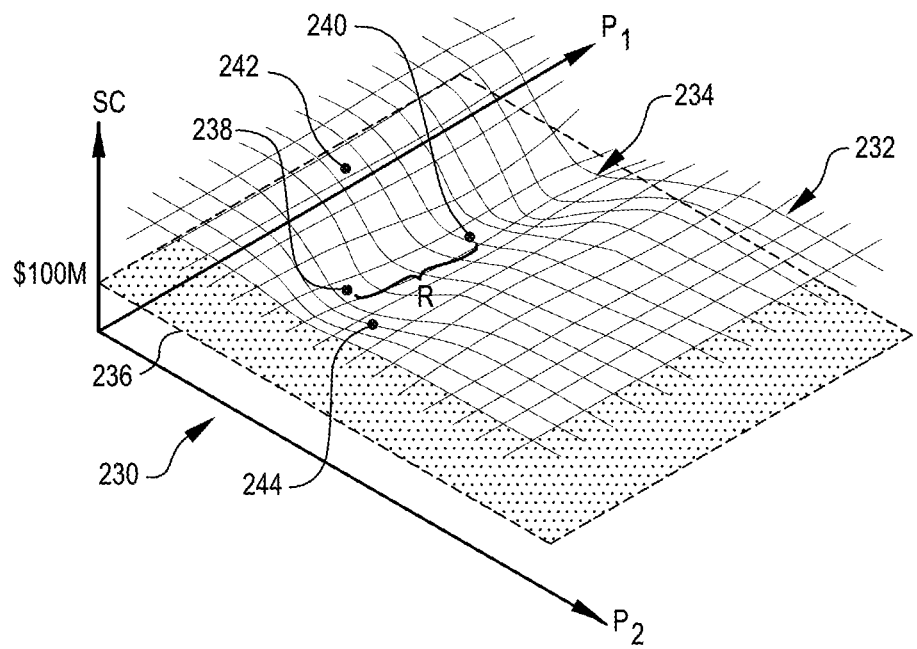
FIG. 19 is a plot of another simulation-result surface generated by an embodiment of the plotter of FIG. 6, where the surface includes valley that does not extend to or below a state-characteristic threshold.

FIG. 19 is a plot 230 of an N=3-dimensional result surface 232, which includes a valley 234; as described above, the plotter 72 (FIG. 6) may generate a representation of the result surface, and the interface 74 (FIG. 6) may convert this representation into a form suitable for displaying the plot of the result surface via the GUI 80 (FIG. 6).

Referring to FIGS. 6 and 19, in an example that is similar to that described above in conjunction with FIGS. 17-18, assume that the simulation tool 60 is simulating a malaria-transmission system, the dimensions of the result surface 232 are $P_1$=vaccination coverage, $P_2$=bed-net coverage, and SC=average cost of the vaccinations and bed nets over the course of a malaria-elimination campaign, and an operator of the simulation tool 60 is desirous of discovering what, if any, values of $P_1$ and $P_2$ yield a value of SC no higher than $100 M.

Therefore, the plotter 72 (FIG. 6) determines if there is a level set at $100 M that includes at least one point of the result surface 232. Conceptually, the plotter 72 may generate a representation of an imaginary plane 236 at SC=$100 M that is parallel with the $P_1$-$P_2$ plane, and any portions of the result surface 232 that are level with this plane form the $100 M level set.

But in this example, unlike the example described above in conjunction with FIGS. 17-18, there are no portions of the peak 234 of the result surface 232 that are level with or lower than the imaginary plane 236; therefore, there is no $100 M level set.

Referring to FIGS. 6 and 19, operation of an embodiment of the determiner 64, simulator 66, calculator 70, and plotter 72 is described in conjunction with the result surface 232.

In an effort to determine whether a $100 M level set exists, the determiner 64 selects next values of vaccination coverage $P_1$ and bed-net coverage $P_2$ for simulation in response to the peak 234. For example, the determiner 64 may randomly select a point 238 of the plot 230 that is within a particular radial distance R from a reference point 240 of the peak 234, and the $P_1$ and $P_2$ coordinates of this randomly selected point 238 are the next values of vaccination coverage and bed-net coverage, respectively. The particular values for the radial distance R and the reference point 240 of the result surface 232 from which the radial distance R is measured may be selected by an operator of the tool 60 via the GUI 80. For example, the radial distance R may be $\sqrt{N}$, and the reference point 240 of the result surface 232 may be the center of mass of the peak 234. It is noted that neither the randomly selected point 238 nor the reference point 240 need lie on the result surface 232, although one or both points may lie on the result surface. Where the randomly selected point 238 lies on the result surface 232, a simulation using the $P_1$ and $P_2$ coordinates of the randomly selected point is typically not a "wasted" situation for reasons similar to those described above in conjunction with FIGS. 14-15.

Consequently, instead of haphazardly selecting next values of the vaccination coverage and bed-net coverage, the determiner 64 selects the next values for these parameters in a methodical manner that may reduce the overall number of simulation points that the simulation tool 60 needs to simulate in order to determine whether there exist values of the vaccination coverage and bed-net coverage that yield the sought-after result of a not-more-than $100 M average cost for vaccinations and bed nets. That is, by selecting the next values of vaccination coverage and bed-net coverage from nearby the peak 234, the determiner 64 may avoid a "wild goose chase" of next values that are unlikely to yield information as to whether there exist values of vaccination coverage and bed-net coverage that yield an average cost that is $100 M or lower.

Still referring to FIGS. 6 and 19, the determiner 64 then passes these next values of vaccination coverage and bed-net coverage, along with the values of any other input data and input parameters that define a full simulation point, to the simulator 66, which runs a number of simulations sufficient to allow the calculator 70 to yield a value of the average cost having one or more uncertainties and standard deviation/variance within respective thresholds, for example, as described above in conjunction with FIG. 9.

Next, the plotter 72 generates a representation of a next point 242 of the plot 230 having coordinates ($P_1$, $P_2$, SC) respectively equal to the next values of the vaccination coverage and bed-net coverage selected by the determiner 64, and to the next value of the average cost calculated by the calculator 70. Although the next point 242 and the point 238 have the same $P_1$ and $P_2$ coordinates, they almost certainly have different SC coordinates for reasons similar to those described above in conjunction with FIGS. 14-15.

Then, the interface 74 saves the representation of the next point 242 of the plot 230 in the output database 76; that is, the interface saves in the output database the values of the input data and input parameters that yielded the next point 242 as well as the SC coordinate of this next point.

Next, the determiner 64 selects next values of the vaccination coverage ($P_1$) and bed-net coverage ($P_2$) nearby the peak 234, and the simulator 66, calculator 70, and plotter 72 repeat their respective above-described operations, which results in the plotter generating a representation of a next point 244 of the plot 230.

The determiner 64, simulator 66, calculator 70, and plotter 72 continue to repeat their above-described operations until the plotter has generated a number of next plot points. An operator of the tool 60 may select this number, which may be greater than or equal to one, via the interface 74.

Then, the plotter 72 generates a representation of an updated result surface 232 using the previously calculated points of the plot 230 (the points that the plotter used to generate the pre-updated version of the result surface) in combination with the next plot points just calculated. For example, the plotter 72 may use a curve-fitting algorithm to determine the updated result surface as a surface that best fits this combination of plot points. And the plotter 72 may also update the location of the reference point 240.

Next, the plotter 72 evaluates the updated result surface 232 and determines whether a $100 M level set exists—the updated result surface 232, because it is updated, may have a different shape than shown in FIG. 19.

If no $100 M level set exists, then the determiner 64, simulator 66, calculator 70, and plotter 72 repeat the above procedure until the iterations of the result surface 232 result in a $100 M level set, or have converged toward a final result surface that is sufficient to indicate that no $100 M level set is likely to exist. For example, an operator user may visually monitor the changes from updated result surface to updated result surface via the GUI 80, and instruct, via the interface 74, the determiner 64, simulator 66, calculator 70, and plotter 72 to repeat the above procedure until a $100 M level set exists, or until he/she feels that the result surface as sufficiently converged toward a final form sufficient to indicate that a $100 M level set is unlikely to exist. Or, an operator may configure the interface 74 to monitor the changes from updated result surface to updated result surface (e.g., to monitor the entropy of the result surface), and to halt the above procedure when either a $100 M level set is discovered or the average change from updated result surface to updated result surface is below an operator-selected threshold.

If a $100 M level set is found, then the determiner 64, simulator 66, calculator 70, and plotter 72 may revert to an embodiment of the procedure described above in conjunction with FIGS. 17-18.

If no $100 M level set is found, then an operator may "tweak" one or more values of the input data and input parameters other than vaccination coverage and bed-net coverage used to form the full simulation point, or the operator may take other action. For example, an operator may decide to investigate disease-intervention parameters other than vaccination coverage and bed-net coverage in a manner similar to that described above for the investigation of vaccination coverage and bed-net coverage.

Still referring to FIGS. 6 and 19, alternate embodiments of the above-described next-value-determination-and-result-surface-updating technique where no sought-after level set exists (at least initially) are contemplated. For example, alternate embodiments described above in conjunction with FIGS. 14-18 may also be compatible with an embodiment described in conjunction with FIG. 19.

Figure 20:
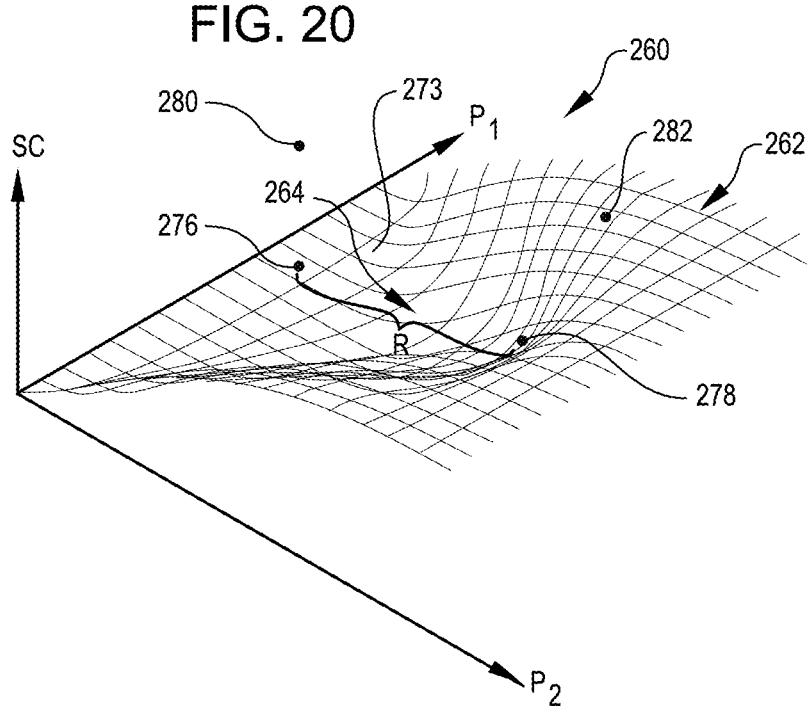
FIG. 20 is a plot of a simulation-result surface generated by an embodiment of the plotter of FIG. 6, where the surface includes a slope that exceeds a slope threshold.

FIG. 20 is a plot 260 of an N=3-dimensional result surface 262, which includes a slope 264; as described above, the plotter 72 (FIG. 6) may generate a representation of the result surface, and the interface 74 (FIG. 6) may convert this representation into a form suitable for displaying the plot of the result surface via the GUI 80 (FIG. 6).

Figure 21:
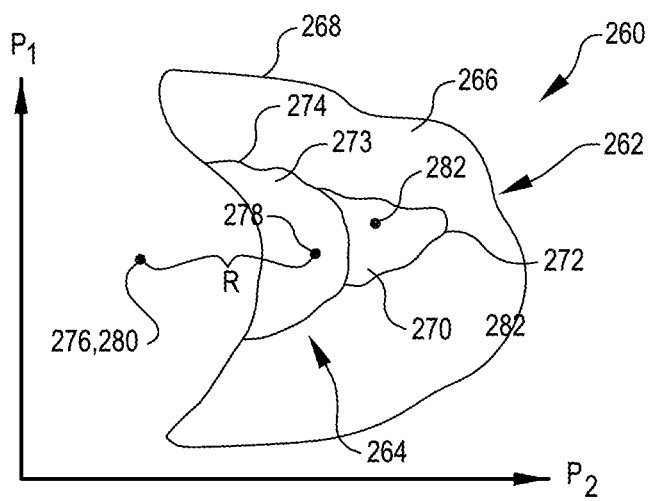
FIG. 21 is a top plan view of the plot of FIG. 20.

FIG. 21 is a plan view of the plot 260, result surface 262, slope 264, a level-set region 266 and a corresponding level set 268, a level-set region 270 and a corresponding level set 272, and a slope region 273 and a corresponding slope-region boundary 274.

Referring to FIGS. 6, 20, and 21 and as further described below, the determiner 64 may determine a next value of an input parameter in response to the level sets 268 and 272 and the slope-region boundary 274 when an operator of the simulation tool 60 is, for example, trying to determine the sensitivity of a sought-after result to one or more input parameters. That is, an operator may be trying to find regions of the result surface 262 where the simulated system may be unstable. As discussed above in conjunction with FIG. 9, an operator may do this to determine the possible effect that parameter, coverage, or model uncertainty may have on a simulation result.

For example, assume that the simulation tool 60 is simulating a malaria-transmission system, the dimensions of the result surface 262 are $P_1$=vaccination coverage, $P_2$=bed-net coverage, and SC=the probability of successful elimination of malaria, and an operator of the simulation tool is desirous of discovering and identifying values of $P_1$ and $P_2$ to which the value of SC is sensitive.

Along the slope 264 within the slope region 273, SC is sensitive to values of $P_1$ and $P_2$ because a relatively small increase in one or both of $P_1$ and $P_2$ may cause a relatively large increase in the value of SC, and because a relatively small decrease in one or both of $P_1$ and $P_2$ may cause a relatively large decrease in the value of SC.

If, for example, the level-set region 270 represents simulation points having a desired probability of success SC (e.g., 99.0% or greater), then an operator may wish to avoid selecting, for use in an actual malaria-elimination campaign, values of $P_1$ and $P_2$ within the level-set region 270 that are also near the slope region 273, because just a slight deviation in one of these values or in another parameter or system value (e.g., due to a simulation error, parameter, coverage, or model uncertainty, or other changes in the actual system compared to the simulated system) may cause the campaign to "fall off a cliff." That is, just a slight deviation in a campaign parameter (e.g., vaccination coverage, bed-net coverage) or in a system condition (e.g., average temperature, average rainfall) or other system quantity may reduce the probability of successful elimination to well below the sought-after level; or, to put it more succinctly, if one bases an elimination campaign on a simulation point that is within the level-set region 270 but that is also near the slope region 273, then even a slight deviation in the actual values of any of the campaign parameters or system conditions/quantities relative to the simulated values may mean the difference between a successful result and an unsuccessful, or even a disastrous, result.

Therefore, an operator may configure the plotter 72 to identify a slope of a result surface such as the slope 264, may identify a slope region, such as the slope region 273, that includes the slope and that is near one or more level sets (e.g., the level set 272) of interest, and may configure the determiner 64 to select values of $P_1$ and $P_2$ near the identified slope region so as to further define the slope region and its slope-region boundary. For example, the plotter 72 may identify as a slope region a region of the result surface 262 having a slope magnitude (rise/run) in the SC dimension that is greater than a threshold (e.g., 25°); or the plotter may identify as a slope region a region of the result surface having a slope magnitude in the SC dimension that is greater than a first threshold (e.g., 25°), and may define the slope-region boundary of the slope region as the points of the result surface were the slope magnitude drops to a second threshold (e.g., one half of the first threshold). The latter slope-region identification technique may impart an increased margin of stability for an actual campaign point that is selected away from the slope region because such a campaign point may be farther away from the steepest slope of the result surface than if the former slope-region identification technique were used.

Referring to FIGS. 6, 20, and 21, operation of an embodiment of the determiner 64, simulator 66, calculator 70, and plotter 72 is described in conjunction with the result surface 262, level-set regions 266 and 270, level sets 268 and 272, slope region 273, and slope-region boundary 274.

In an effort to further define the slope-region boundary 274 of the slope region 273, which includes the slope 264, the determiner 64 selects next values of vaccination coverage $P_1$ and bed-net coverage $P_2$ for simulation in response to the slope-region boundary 274. For example, the determiner 64 may randomly select a point 276 of the plot 260 that is within a particular radial distance R from a reference point 278 of the result surface 262, and the $P_1$ and $P_2$ coordinates of this randomly selected point 276 are the next values of vaccination coverage and bed-net coverage, respectively. The particular values for the radial distance R and the reference point 278 of the result surface 262 from which the radial distance R is measured may be selected by a user of the tool 60 via the GUI 80. For example, the radial distance R may be $\sqrt{N}$, and the reference point 278 may be the center of mass of the slope region 273. It is noted that neither the randomly selected point 276 nor the reference point 278 need lie on the result surface 262, although one or both of these points may lie on the result surface. Where the randomly selected point 276 lies on the result surface 262, a simulation using the $P_1$ and $P_2$ coordinates of the randomly selected point is typically not a "wasted" situation for reasons similar to those described above in conjunction with FIGS. 14-15.

Consequently, instead of haphazardly selecting next values of the vaccination coverage and bed-net coverage, the determiner 64 selects the next values for these parameters in a methodical manner that may reduce the overall number of points that the tool 60 needs to simulate for sufficiently defining the slope-region boundary 274. That is, by selecting the next values of vaccination coverage and bed-net coverage from within or nearby the slope region 273 or from on or nearby the slope-region boundary 274, the determiner 64 may avoid a "wild goose chase" of next values that are unlikely to yield significant information regarding the location of the slope-region boundary 274.

Still referring to FIGS. 6, 20, and 21, the determiner 64 then passes these next values of vaccination coverage and bed-net coverage, along with the values of any other input data or input parameters that define a full simulation point, to the simulator 66, which runs a number of simulations sufficient to allow the calculator 70 to yield a value of the probability of successful malaria elimination having one or more uncertainties and variance within respective thresholds, for example as described above in conjunction with FIG. 9.

Next, the plotter 72 generates a representation of a next point 280 of the plot 260 having coordinates ($P_1$, $P_2$, SC) respectively equal to the next values of the vaccination coverage and bed-net coverage selected by the determiner 64, and to the next value of the probability of success calculated by the calculator 70. Although the points 276 and 280 have the same $P_1$ and $P_2$ coordinates, they almost certainly have different SC coordinates as described above in conjunction with FIGS. 14-15.

Then, the interface 74 saves the representation of the next point 280 of the plot 260 in the output database 76; that is, the interface saves the $P_1$, $P_2$, and SC coordinates of the next point 280 as well as the values of the input data and other input parameters that yielded this next point.

Next, the determiner 64 uses the slope-region boundary 274 to select next values of the vaccination coverage ($P_1$) and bed-net coverage ($P_2$), and the simulator 66, calculator 70, and plotter 72 repeat their respective above-described operations, which result in a representation of a next point 282 of the plot 260.

The determiner 64, simulator 66, calculator 70, and plotter 72 continue to repeat their above-described operations until the plotter has generated a number of next plot points sufficient to update the result surface 262. An operator of the simulation tool 60 may select this number, which may be greater than or equal to one, via the interface 74.

Then, the plotter 72 updates the result surface 262 using the previously calculated points of the plot 260 (the points that the plotter used to generate the pre-updated version of the result surface) in combination with the next plot points (e.g., 280, 282) just calculated. For example, the plotter 72 may use a curve-fitting algorithm to determine the updated result surface as a surface that best fits this combination of plot points. The plotter 72 may also update the location of the reference point 278. The plotter 72 then generates a representation of the updated result surface 262; because the result surface is updated, it may have a different shape than appears in FIGS. 20 and 21.

Next, the plotter 72 updates the level sets 268 and 272 and the slope-region boundary 274 based on the updated result surface 262—because of the updating, these updated level sets and slope-region boundary may look different than they appear in FIGS. 20 and 21.

Then, the determiner 64, simulator 66, calculator 70, and plotter 72 repeat the above procedure until the iterations of the result surface 262 have sufficiently converged toward a final result surface with a final slope region 273 and slope-region boundary 274. For example, an operator of the simulation tool 60 may visually monitor the changes from updated result surface to updated result surface via the GUI 80, and instruct, via the interface 74, the determiner 64, simulator 66, calculator 70, and plotter 72 to repeat the above procedure until he/she feels that the result surface as sufficiently converged toward a final form. Or, an operator may configure the interface 74 to monitor the changes from updated result surface to updated result surface (e.g., to monitor the entropy of the result surface), and to halt the above procedure when the change from updated result surface to updated result surface is below an operator-selected threshold.

After the slope region 273 and slope-region boundary 274 are sufficiently defined, an operator may continue the simulation to find suitable values for vaccination coverage $P_1$ and bed-net coverage $P_2$ that correspond to a sought-after probability of success as described above in conjunction with FIGS. 14-16 to further develop, for example, the level set 268.

Then, an operator may select the values of the vaccination coverage and the bed-net coverage to be used in an actual disease-elimination campaign from a point of the plot 260 that is on or off the result surface 262 as described above in conjunction with FIGS. 14 and 15, with the additional restriction that the point is a safe distance away from the slope-region boundary 274. That is, an operator may select the values of vaccination coverage and bed-net coverage to be used in an actual campaign from a point that corresponds to a margin of system stability greater than a threshold that may be determined based on the disease to be eliminated or on other criteria.

Still referring to FIGS. 6, 20, and 21, alternate embodiments of the above-described next-value-determination-and-result-surface-updating technique are contemplated. For example, alternate embodiments described above in conjunction with FIGS. 14-19 may be application to the procedure described above in conjunction with FIGS. 20-21. Furthermore, although the slope-region boundary 274 is described as a being coincident with portions of the level sets 268 and 272, the boundary 274 may be coincident with only one, or with none, of the level sets 268 and 272.

Figure 22:
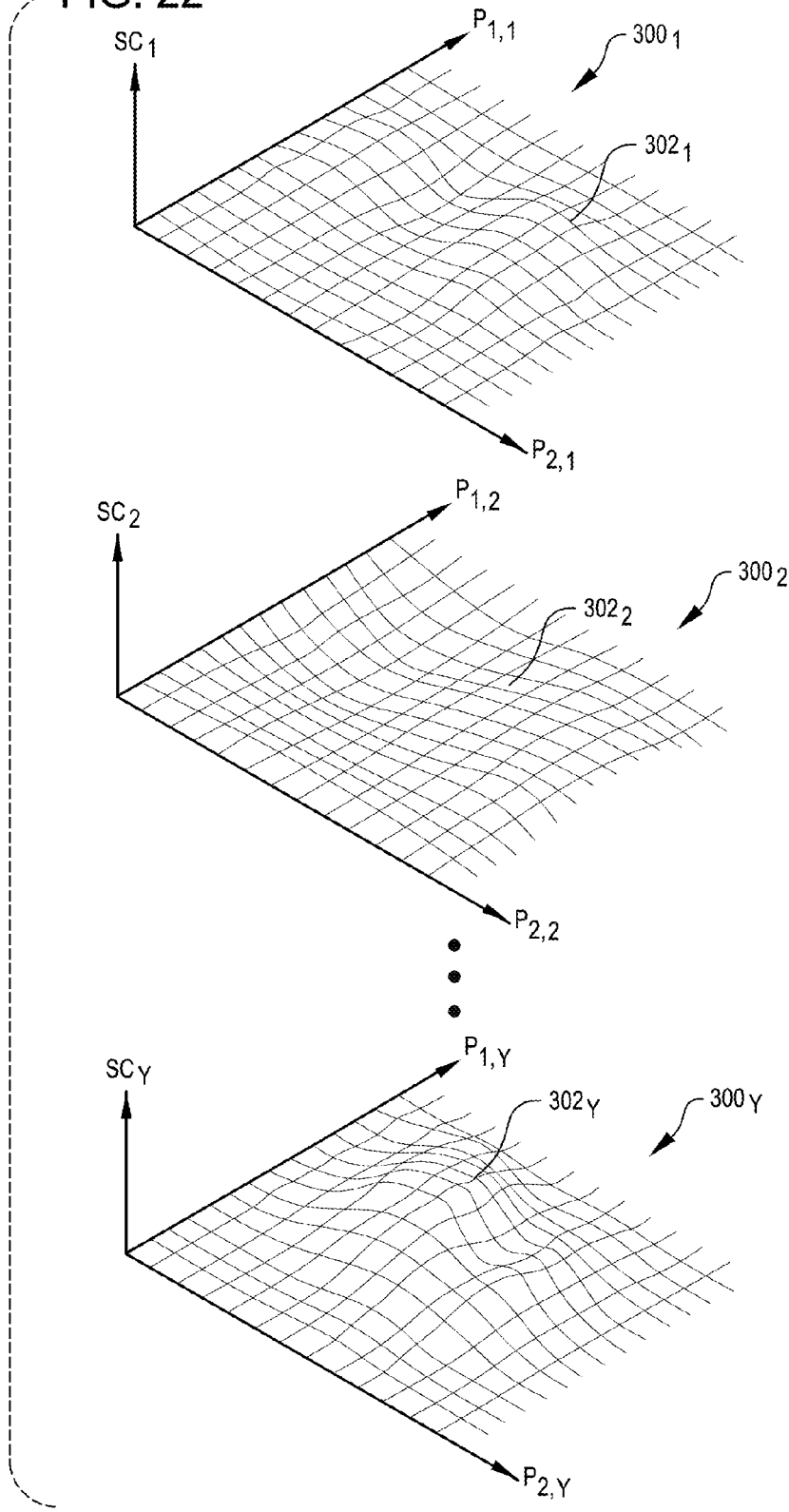
FIG. 22 is a group of plots of simulation-result surfaces generated by an embodiment of the plotter of FIG. 6, where the plots each have at least one common dimension.

FIG. 22 is a set of plots $300_1$-$300_y$ of respective result surfaces $302_1$-$302_y$, each having at least one common dimension; for example, one or more of the result surfaces $302_1$-$302_y$ may be similar to one or more of the result surfaces 152, 182, 202, 232, and 262 of FIGS. 14-21; as described above, the plotter 72 (FIG. 6) may generate respective representations of the result surfaces $302_1$-$302_y$, and the interface 74 (FIG. 6) may convert these representations into a forms suitable for displaying the plots of the result surfaces via the GUI 80 (FIG. 6).

Referring to FIGS. 6 and 22, the determiner 64 may select a respective next value of one or more input parameters based on more than one of the result surfaces $302_1$-$302_y$, for example, when an operator of the simulation tool 60 is desirous of finding values of the input parameter(s) that satisfy multiple criteria.

For example, suppose an operator wishes to determine whether there exist values of vaccination coverage and bed-net coverage that yield both a probability of successful malaria elimination that is 99% or greater at an average cost of $100 M or less.

He/she may configure the determiner 64 to use the plots 150 of FIGS. 14-15 and 200 of FIGS. 17-18 to select next values of vaccination coverage and bed-net coverage in response to both of the level sets 158 (FIGS. 14-15) and 208 (FIGS. 17-18). Specifically, the determiner 64 may select next values of vaccination coverage and bed-net coverage from respective simulation points that are within radii $R_1$ and $R_2$ of the reference points 164 and 214 of the plots 150 (FIGS. 14-15) and 200 (FIGS. 17-18), respectively—$R_1$ and $R_2$ may, but need not be, equal to one another.

Then, the determiner 64, simulator 66, calculator 70, and plotter 72 may operate as described above in conjunction with FIGS. 14-15 and 17-18 to develop the result surfaces 152 and 202 sufficiently for an operator to identify values of vaccination coverage and bed-net coverage that yield a probability of elimination of at least 99% at an average cost of no more than $100 M.

If the determiner 64 can find no next values of vaccination coverage and bed-net coverage that are within the specified ranges of both level sets 158 and 208, then it may notify an operator via the GUI 80.

In response to such notification, an operator may configure the simulation tool 60 to "relax" one or both of the next-point-selection criteria. For example, one may configure the determiner 64 to use a $150 M level set in the plot 200 instead of a $100 M level set, or to use a 98% level set in the plot 150 instead of a 99% level set. Or, an operator may shift the reference points 164 (FIGS. 14-15) and 214 (FIGS. 17-18), e.g., closer to the respective level sets 158 and 208 to allow selection of next values farther outside of these level sets and farther outside of the level-set regions 156 and 206.

Or, an operator may configure the simulation tool 60 to automatically relax one or both of the next-point-selection criteria. For example, an operator may configure the tool 60 such that it steps the probability level set down from 99% to 98% in 0.1% intervals, steps the average-cost level set up from $100 M to $150 M in $5 M intervals, or moves the reference points closer to the respective level sets in intervals of R/N until the determiner 64 is able to find a simulation point that is within $R_1$ and $R_2$ of both reference points, respectively.

An operator may also use multiple ones of the plots $300_1$-$300_y$ to determine which values of multiple input parameters yield a same sought-after result. For example, suppose an operator wants to determine which set of values of vaccination coverage, bed-net coverage, mosquitocide coverage, and malaria-prevention-education coverage yield a probability of eliminating malaria greater than or equal to 99%. Instead of configuring the plotter 72 (FIG. 6) to generate a representation of an N=5-dimensional plot, to reduce processing complexity and to facilitate plot display, an operator may configure the plotter to generate two N=3-dimensional plots having the following sets of dimensions: 1) $P_{1,1}$=vaccination coverage, $P_{2,1}$=bed-net coverage, $SC_1$=probability of elimination, and 2) $P_{1,2}$=mosquitocide coverage, $P_{2,2}$=education coverage, and $SC_2$=probability of elimination. Therefore, in this example, these two plots have only their SC dimensions in common.

Still referring to FIG. 22, alternate embodiments of the plots $300_1$-$300_y$ and procedures for using these plots to select one or more next input-parameter values are contemplated. For example, one or more of the alternate embodiments described above in conjunction with FIGS. 14-21 may be applicable to the plots $300_1$-$300_y$ and the procedures for using these plots. Furthermore, although all shown having the same number of dimensions, these plots may have different numbers of dimensions.

Figure 23:
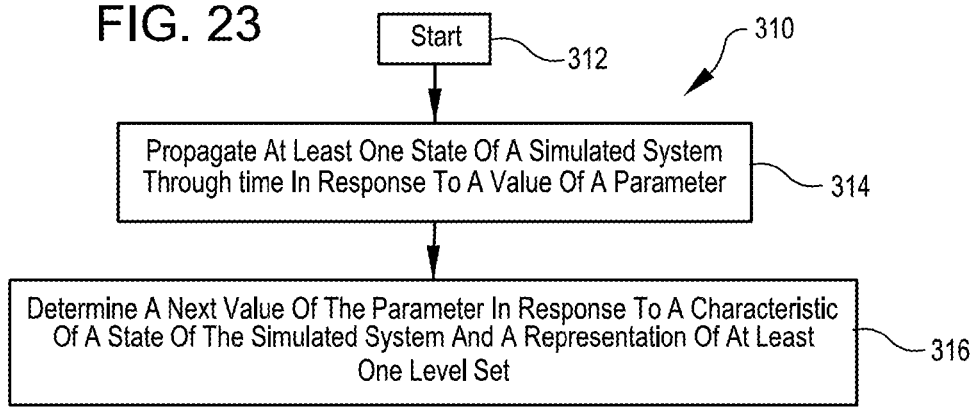
FIG. 23 is a flow chart of an embodiment of a technique for determining a next value of a parameter for system simulation.

FIG. 23 is a flow chart 310 of an embodiment of a system-simulation procedure that an embodiment of the simulation tool 60 of FIG. 6 may implement.

Referring to FIG. 6 and to a block 312 of FIG. 23, the tool 60 starts a simulation of a stochastically modeled system.

Next, referring to block 314 of FIG. 23, the simulator 66 propagates at least one state of the simulated system through time in response to a value of an input parameter received from the determiner 64. For example, if the system model 68 is model of a malaria-transmission system, then the simulator 66 may propagate through time a state that represents the number of mosquitos infected with malaria in response to one or more input-data and/or input-parameter values such as a value of vaccination coverage received from the determiner 64.

Then, referring to block 316, the determiner 64 determines a next value of the input parameter in response to a characteristic of a state of the model and a representation of at least one level set. For example, referring to FIGS. 14-15, the determiner 64 may determine a next value for vaccination coverage $P_1$ in response to the probability of successful eradication SC, which is a characteristic of a state that represents the number of malaria-infected individuals, and at least one level set 158. In this example, the points of the plot 150 from which the determiner 64 may determine the next value of vaccination coverage $P_1$ are within a radius R of a level-set reference point 164; therefore, these points are within a range of SC values dictated by the level set 158. That is, the determiner 64 determines a next value of vaccination coverage $P_1$ by selecting a point (e.g., point 166) of the plot 150 that is within a sphere of radius R from the level-set reference point 164; consequently, the only points that the determiner may select are in a spherical region of the plot 150 where the probability of success SC is within a certain range of values.

Still referring to FIGS. 6 and 23, alternate embodiments of the simulation procedure are contemplated. For example, alternate embodiments described above in conjunction with FIGS. 6-22 may be applicable to the simulation procedure of FIG. 23. Furthermore, although described as being different states, the state that the simulator 66 propagates through time may be the same as the state having the state characteristic. For example, the simulator 66 may propagate a state representing the number of infected individuals through time, and the state characteristic may be the probability of successful eradication, which is a characteristic of the state representing the number of infected individuals. Moreover, although described as determining a next value for only one parameter, an embodiment of the procedure may determine respective next values for multiple parameters. Moreover, although described as being responsive to a state characteristic and a level set, an embodiment of the procedure may be responsive to a state characteristic and multiple level sets, to multiple state characteristics and a level set, or to multiple state characteristics and multiple level sets. In addition, any step described as being performed by a component of the simulation tool 60 may be performed by another component of the tool, or by any combination of components of the tool. In addition, although described as a stochastically modeled system, the system may be modeled other than stochastically. Furthermore, although described as propagating a state of the simulated system through time, the simulator 66 (FIG. 6) may simulate the system in another manner.

Figure 24:
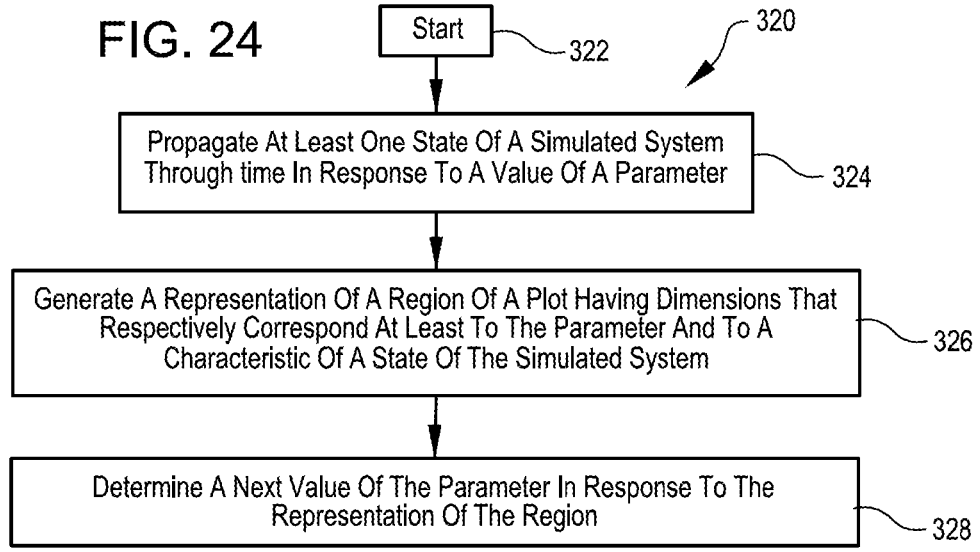
FIG. 24 is a flow chart of another embodiment of a technique for determining a next value of a parameter for system simulation.

FIG. 24 is a flow chart 320 of an embodiment of a simulation procedure that an embodiment of the simulation tool 60 of FIG. 6 may implement.

Referring to FIG. 6 and to block 322 of FIG. 24, the tool 60 starts a simulation of a stochastically modeled system.

Next, referring to block 324 of FIG. 24, the simulator 66 propagates at least one state of the simulated system through time in response to a value of an input parameter received from the determiner 64. For example, if the system model 68 is model of a malaria-transmission system, then the simulator 66 may propagate through time a state that represents the number of mosquitos infected with malaria in response to one or more input-data or input-parameter values, such as a value of vaccination coverage received, from the determiner 64.

Then, referring to block 326, the plotter 72 generates a representation of a region of a plot having dimensions that respectively correspond at least to the parameter and to a characteristic of a state of the simulated system. For example, referring to FIGS. 14-15, the plotter 72 may generate the result surface 152 (a region) of the plot 150, and the result surface has dimensions $P_1$ and SC that respectively correspond to the parameter such as vaccination coverage and to a probability of successful elimination, which is a characteristic of the simulated-system state representing the number of infected individuals.

Next, referring to block 328, the determiner 64 determines a next value of the parameter in response to the representation of the region of the plot. For example, referring to FIGS. 14-15, the determiner 64 may determine a next value of the input parameter vaccination coverage in response to a representation of the result surface 152 of the plot 150. More specifically, the determiner 64 may determine a next value of the input parameter vaccination coverage in response to the representation of the portion of the result surface 152 within the level-set region 156.

Still referring to FIGS. 6 and 24, alternate embodiments of the simulation procedure are contemplated. For example, alternate embodiments described above in conjunction with FIGS. 6-23 may be applicable to the simulation procedure of FIG. 23.

Figure 25:
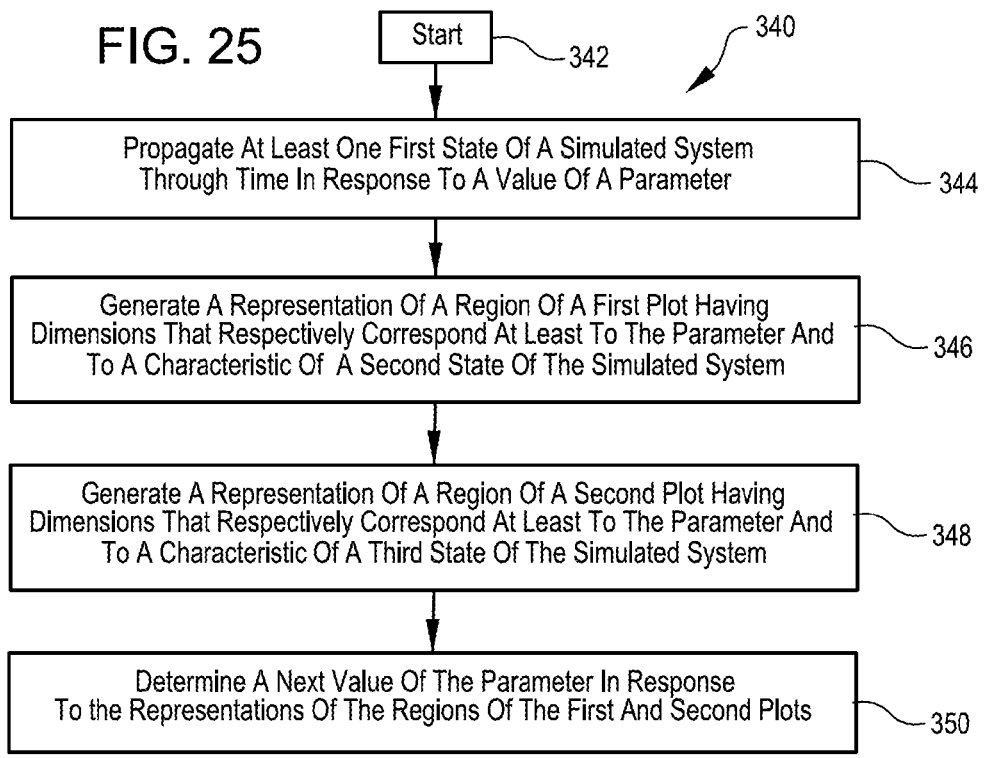
FIG. 25 is a flow chart of another embodiment of a technique for determining a next value of a parameter for system simulation.

FIG. 25 is a flow chart 340 of an embodiment of a simulation procedure that an embodiment of the simulation tool 60 of FIG. 6 may implement.

Referring to FIG. 6 and to a block 342 of FIG. 25, the tool 60 starts a simulation of a stochastically modeled system.

Next, referring to block 344 of FIG. 25, the simulator 66 propagates at least one state of the simulated system through time in response to a value of an input parameter received from the determiner 64. For example, if the system model 68 is model of a malaria-transmission system, then the simulator 66 may propagate through time a state that represents the number of mosquitos infected with malaria in response to one or more input-data or input-parameter values such as a value of vaccination coverage received from the determiner 64.

Then, referring to block 346, the plotter 72 generates a representation of a region of a first plot having dimensions that respectively correspond at least to the parameter and to a characteristic of a state of the simulated system. For example, referring to FIGS. 14-15, the plotter 72 may generate the result surface 152 (a region) of the plot 150, and the result surface has dimensions $P_1$ and SC that respectively correspond to the parameter such as vaccination coverage and to a probability of successful elimination, which is a characteristic of the simulated-system state representing the number of infected individuals.

Then, referring to block 348, the plotter 72 generates a representation of a region of a second plot having dimensions that respectively correspond at least to the parameter and to a characteristic of a state of the simulated system. For example, referring to FIGS. 17-18, the plotter 72 may generate the result surface 202 (a region) of the plot 200, and the result surface has dimensions $P_1$ and SC that respectively correspond to the parameter such as vaccination coverage and to an average cost of vaccination coverage and bed-net coverage, which is a characteristic of the simulated-system state representing the cumulative cost of vaccination coverage and bed-net coverage.

Next, referring to block 350, the determiner 64 determines a next value of the parameter in response to the representations of the regions of the first and second plots. For example, referring to FIGS. 14-15 and 17-18, the determiner 64 may determine a next value of the input parameter vaccination coverage in response to representations of the result surfaces 152 and 202 of the plots 150 and 200, respectively. More specifically, the determiner 64 may determine a next value of the input parameter vaccination coverage in response to the representations of the portions of the result surfaces 152 and 202 within the level-set regions 156 and 206, respectively, in an effort to find a value of vaccination coverage that corresponds to an elimination probability of 99% or greater and an average cost of $100 M or less.

Still referring to FIGS. 6 and 25, alternate embodiments of the simulation procedure are contemplated. For example, alternate embodiments described above in conjunction with FIGS. 6-24 may be applicable to the simulation procedure of FIG. 25. Furthermore, although described as being different, two or more of the described states may be the same, and the described state characteristics may be the same. Moreover, although described as using the regions from two plots, the procedure may be responsive to regions from more than two plots, and these plots may collectively include as dimensions more than two state characteristics and more than two input parameters.

Figure 26:
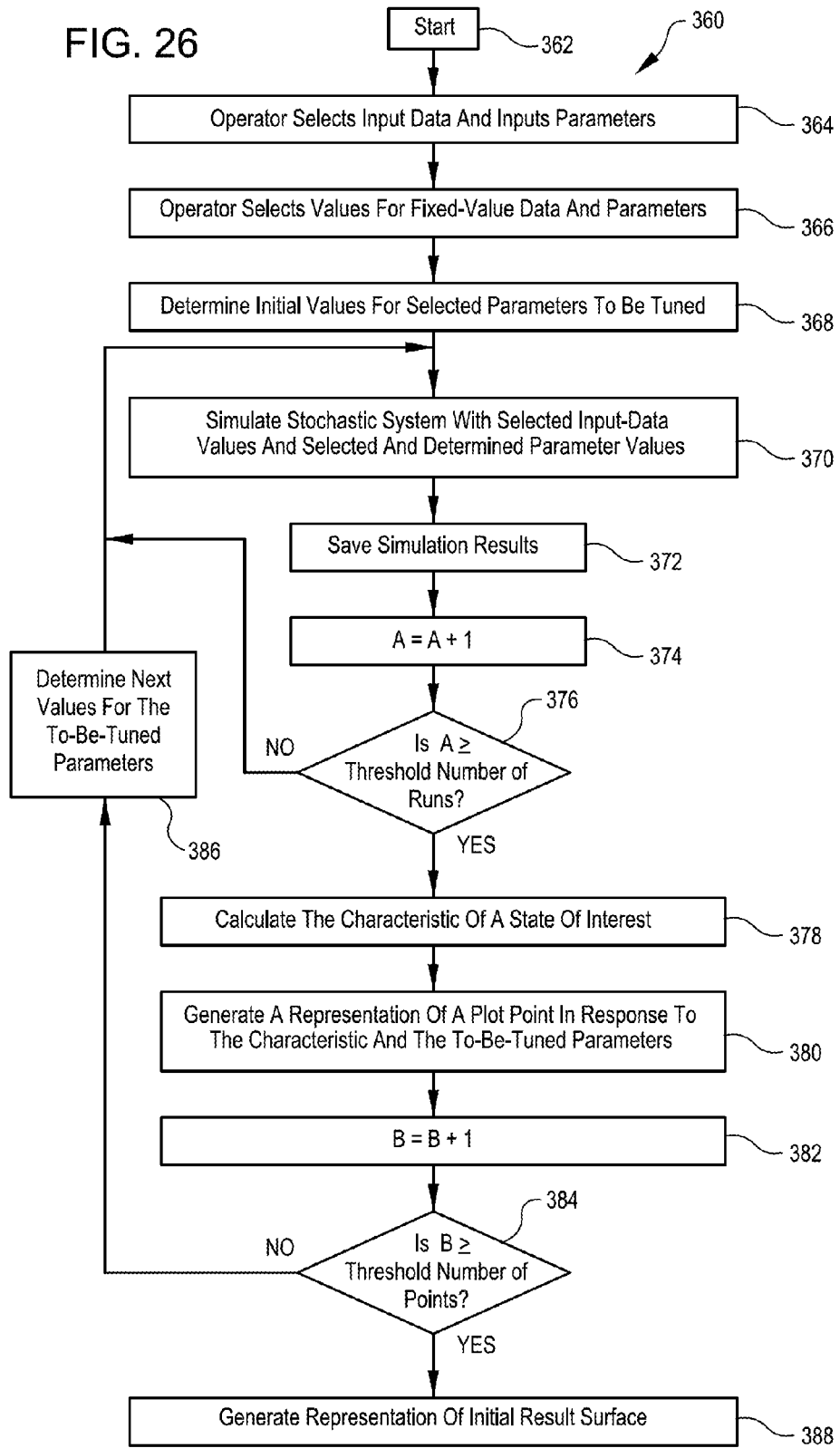
FIG. 26 is a flow chart of an embodiment of a technique for generating an initial simulation-result surface.

FIG. 26 is a flow chart 360 of an embodiment of a procedure that an embodiment of the simulation tool 60 of FIG. 6 may implement to generate respective representations of one or more initial result surfaces.

Referring to FIG. 6 and to a block 362 of the FIG. 26, the tool 60 starts a simulation of a stochastically modeled system.

Next, referring to block 364 of FIG. 26, an operator of the tool 60 selects, via the GUI 80, the input data and the input parameters that will collectively form a simulation point. For example, if an operator wishes to model a malaria-transmission system in Madagascar, then he/she may select input-data categories (e.g., average temperature, average rainfall, population) that the input data base 62 stores for Madagascar, and may select input parameters specific to malaria elimination (e.g., vaccination coverage, bed-net coverage, mosquitocide coverage).

Then, referring to block 366, an operator selects, via the GUI 80, the values for any input data (e.g., weather-related input data) or input parameters that are to remain constant or otherwise unchanged from their respective initial values during the simulation. For example, for the input data, an operator may select values that are stored in the input database 62.

Next, referring to block 368, the determiner 64 determines initial values of the input parameters to be "tuned," i.e., the input parameters for which the determiner will attempt to find values that correspond to a sought-after result. For example, for a malaria-transmission system, an operator may configure the determiner 64 to find values of vaccination coverage and bed-net coverage that correspond to at least a 99% probability of successful elimination. For example, the determiner 64 may determine the initial values of the input parameters to be tuned according to an embodiment described above in conjunction with FIGS. 12 and 13.

Then, referring to block 370, the simulator 66 simulates the stochastically modeled system over the period of interest (e.g., a disease-elimination campaign) in response to the input-data values and the input-parameter values (including the initial values for the input parameters to be tuned) received from the determiner 64.

Next, referring to block 372, the interface 74 saves the simulation results (e.g., a snapshot of the states of the simulated system at each time step) in the output database 76.

Then, referring to block 374, the calculator 70 increments a value A, which has an initial value of zero and which represents the number of simulation runs that the simulator 66 has performed at the current simulation point.

Next, referring to block 376, the calculator 70 determiners if A is greater than or equal to a threshold number of simulation runs. In an embodiment, the threshold number is a number sufficient for the calculator 70 to yield a state characteristic (e.g., probability of successful elimination) having one or more uncertainties and standard deviation/variance within respective thresholds. The threshold number of simulation runs may be selected by an operator of the simulation tool 60. Or, the calculator 70 may effectively calculate the threshold number by calculating the uncertainty(ies) and standard deviation/variance of the result after each simulation run, and by effectively indicating that A is greater than or equal to the threshold number when the uncertainty(ies) and standard deviation/variance of the result are within respective thresholds.

If A is not actually or effectively greater than or equal to the threshold number of runs through the simulator 66, then the procedure returns to block 370, and repeats the steps represented by the blocks 370, 372, 374, and 376 until A is actually or effectively greater than the threshold number of simulation runs.

Then, referring to block 378, the calculator 70 calculates a characteristic (e.g., probability of successful elimination) of a state of interest (e.g., the number of infected individuals at the end of a simulated disease-elimination campaign period), where the calculated characteristic has one or more uncertainties and standard deviation/variance within respective thresholds.

Next, referring to block 380, the plotter 72 generates a representation of a plot point in response to the calculated characteristic (e.g., probability of successful elimination) and the to-be-tuned input parameters (e.g., vaccination coverage and bed-net coverage). In an embodiment, the plotter 72 generates the plot point having coordinates equal to the values of the calculated characteristic and the values of the to-be-tuned input parameters.

Then, referring to block 382, the plotter 72 increments a value B, which is initially zero and which represents the number of plot points generated by the plotter.

Next, referring to block 384, the plotter 72 determines whether B is greater than or equal to a threshold number of points that the plotter needs to generate an initial version of a result surface. In an embodiment, the threshold number may be selected by an operator of the simulation tool 60. Or, the plotter 72 may effectively calculate the threshold number on a case-by-case basis depending on the number and locations of the points, and by effectively indicating that B is greater than or equal to the threshold number when the number of points is sufficient for generating an initial result surface.

If B is not greater than or equal to the threshold number of points, then, referring to block 386, the determiner 64 determines next values of the to-be-tuned input parameters, and the procedure repeats the steps represented by the blocks 370, 372, 374, 376, 378, 380, 382, 384, and 386 until B is greater than or equal to the threshold number of points. The determiner 64 may determine the next values of the to-be-tuned input parameters according to an embodiment described above in conjunction with FIGS. 12-13.

Referring again to block 384, if B is greater than or equal to the threshold number of points, then, referring to block 388, the plotter 72 generates a representation of an initial result surface from the generated plot points. In an embodiment, the plotter 72 generates a representation of the initial result surface by applying a conventional curve-fitting algorithm to the plot points.

Still referring to FIGS. 6 and 26, alternate embodiments of the procedure are contemplated. Embodiments described above in conjunction with FIGS. 12-25 may be applicable to an embodiment of the procedure of FIG. 26. Furthermore, although described as calculating a single state characteristic for a single state, an embodiment of the procedure may calculate multiple state characteristics for a single state, a single state characteristic for multiple states, or multiple state characteristics for multiple states. Moreover, although described as generating a representation of an initial result surface, an embodiment of the procedure may generate respective representations of multiple initial result surfaces; for example, the simulator tool 60 may repeat the procedure represented by the flow chart 360 multiple times either consecutively or concurrently, one time per each initial result surface to be generated.

FIG. 27 is a flow chart 400 of an embodiment of a procedure that an embodiment of the simulation tool 60 of FIG. 6 may implement to find a value of an input parameter that corresponds to a sought-after result, or to discover that no such value exists.

Referring to FIG. 6 and to block 402 of FIG. 27, the tool 60 starts after the plotter 72 has generated representations of one or more initial result surfaces, for example, as described above in conjunction with FIG. 26.

Next, referring to block 404, the plotter 72 generates a representation of a respective at least one level set for each initial result surface represented. For example, the plotter 72 may generate such a level set according to an embodiment described above in conjunction with FIGS. 14-22. An operator of the tool 60 may define these level sets via the GUI 80. For example, for simulating a malaria transmission system, an operator may define a level set for probability of successful elimination equal to 99%.

Then, referring to block 406, the determiner 64 attempts to determine a respective next value for each of the to-be-tuned input parameters in response to at least one region of at least one result surface and in response to a respective at least one level set for each of these result surfaces. For example, for a malaria-transmission system, the determiner 64 may select a next value of vaccination coverage from a plot point that is within a radius R of a reference point corresponding to a 99%-success level set according to an embodiment described above in conjunction with FIGS. 14-15.

Next, referring to block 408, if the determiner 64 does not find next values for all of the to-be-tuned input parameters, then the procedure proceeds to block 410.

Then, referring to block 410, the tool 60 "decides" whether the determiner 64 is to retry determining a next value of the parameter for which it could not find a next value. For example, the tool 60 may notify an operator, who may decide to relax the next-value-determination criteria according to an embodiment described above in conjunction with FIGS. 16 and 19. Or, an operator may have previously configured the tool 60 to automatically relax the next-value-determination criteria according to an embodiment described above in conjunction with FIGS. 16 and 19.

If the tool 60 or operator decides to retry the next-value determination, then the procedure returns to block 406.

If, however, the tool 60 or operator decides not to retry the next-value determination, for example, because a threshold number of retries has already been made, then the tool notifies the operator of the problem via the GUI 80 and finishes at a block 432.

Referring again to block 408, if the determiner 64 is able to find next values for all of the to-be-tuned parameters, then the simulation tool 60 proceeds to the step represented by a block 412.

Next, referring to block 412, the simulator 66 simulates the stochastically modeled system over the period of interest (e.g., a disease-elimination campaign) in response to the input-data values and the input-parameter values (including the determined next values for the input parameters to be tuned) received from the determiner 64.

Then, referring to block 414, the interface 74 saves the simulation results (e.g., a snapshot of the states of the simulated system at each time step) in the output database 76.

Next, referring to block 416, the calculator 70 increments a value C, which has an initial value of zero and which represents the number of simulation runs that the simulator 66 has performed at the current simulation point.

Then, referring to block 418, the calculator 70 determiners if C is greater than or equal to a threshold number of simulation runs. In an embodiment, the threshold number is a number sufficient for the calculator 70 to yield a state characteristic (e.g., probability of successful elimination) having one or more uncertainties and standard deviation/variance within respective thresholds. The threshold number of simulation runs may be selected by an operator of the simulation tool 60. Or, the calculator 70 may effectively calculate the threshold number by calculating the uncertainty(ies) and standard deviation/variance of the result after each simulation run, and by effectively indicating that C is greater than or equal to the threshold number of simulation runs when the uncertainty(ies) and standard deviation/variance of the result are within respective thresholds.

If C is not actually or effectively greater than or equal to the threshold number of runs through the simulator 66, then the procedure returns to block 412, and repeats the steps represented by the blocks 412, 414, 416, and 418 until C is actually or effectively greater than the threshold number of simulation runs.

Next, referring to block 420, the calculator 70 calculates a respective characteristic (e.g., probability of successful elimination) for each of at least one state of interest (e.g., the number of infected individuals remaining at the end of a simulated campaign period), where the calculated characteristic has one or more uncertainties and standard deviation/variance within respective thresholds.

Then, referring to block 422, the plotter 72 generates a representation of a respective plot point for each result surface in response to the corresponding calculated characteristic (e.g., probability of successful elimination) and the corresponding to-be-tuned input parameters (e.g., vaccination coverage and bed-net coverage). In an embodiment, the plotter 72 generates the representation of each plot point having coordinates equal to the values of the corresponding at least one calculated characteristic and the values of the at least one to-be-tuned input parameters.

Next, referring to block 424, the plotter 72 increments a value D, which is initially zero and which represents the number of plot points that the plotter has generated for each result-surface plot. Alternatively, the plotter 72 may increment a respective value D for each result surface.

Then, referring to block 426, the plotter 72 determines whether D is greater than or equal to a threshold number of points. In an embodiment, the threshold number of points that the plotter 72 generates for producing an updated version of a result surface may be selected by an operator of the simulation tool 60. Or, the plotter 72 may effectively calculate the threshold number of plot points on a case-by-case basis depending on the number and locations of the points within a plot, and by effectively indicating that D is greater than or equal to the threshold number when the number of points is sufficient for generating an updated result surface. If the threshold number is different for each of multiple result surfaces, then the plotter 72 may use as D the threshold number of the result surface needing the greatest number of points for updating, or the plotter may generate separate D values for each result surface per above, and may indicate that the threshold number of points has been reached for all result surfaces when each of these D values is greater than or equal to the number of points needed for updating the corresponding result surface.

If D is not greater than or equal to the threshold number of points, then the simulation tool 60 returns to the step represented by the block 406, and repeats the steps represented by the blocks 406, 408, 410 (if applicable), 412, 414, 416, 418, 420, 422, 424, and 426 until D is greater than or equal to the threshold number of points.

Referring again to block 426, if D is greater than or equal to the threshold number of points, then, referring to block 428, the plotter 72 updates the representations of the result surfaces from the previously generated plot points (used for generation of the initial result surface and any prior updates of the result surface) and just-generated plot points. In an embodiment, the plotter 72 updates the representation of each result surface by applying respective curve-fitting algorithms to the respective sets of plot points.

Next, referring to block 430, the tool 60 determines whether the result surfaces are sufficiently developed to yield final results. For example, as described above in conjunction with FIGS. 14-22, either an operator or the tool 60 may monitor the changes (e.g., the entropy) in the result surfaces from update to update, and determine that the surfaces are sufficiently developed if the level of change is less than or equal to a threshold level of change. The monitoring algorithm may be the same or different for each result surface, and the operator/tool 60 may find one surface sufficiently developed before it finds another surface sufficiently developed.

If at least one of the result surfaces is not sufficiently developed to yield a final result, then the simulation tool 60 returns to the step represented by the block 406, and repeats the steps represented by the blocks 406, 408, 410 (if applicable), 412, 414, 416, 418, 420, 422, 424, 426, 428, and 430 until all of the result surfaces are sufficiently developed, or until the tool 60 times out because at least one of the result surfaces is not converging toward a final surface. The tool 60 may repeat these steps only for the result surfaces that are not sufficiently developed.

But if all result surfaces are sufficiently developed to yield a final result, then the tool 60 ends the procedure at block 432, and an operator may analyze the plots of the result surfaces and level sets via the GUI 80 (or in some other manner) and select values of the now-tuned input parameters for use in an actual system.

Still referring to FIGS. 6 and 27, alternate embodiments of the procedure are contemplated. Embodiments described above in conjunction with FIGS. 12-26 may be applicable to an embodiment of the procedure of FIG. 27. Furthermore, an embodiment of the procedure may be applicable to any number of state characteristics and any number of to-be-tuned input parameters per result-surface plot.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus, comprising:
   a simulator that includes one or more computing circuits and that is configured to simulate a system and to propagate at least one state of the simulated system through time in response to a value of a parameter;
   a generator configured to generate a representation of a region of a plot having dimensions that respectively correspond at least to the parameter and to a characteristic of another state of the simulated system, the representation of the region including
      a representation of a multi-point first subregion of the plot, the first subregion spanning a multi-value range of the characteristic, and
      a representation of a second subregion of the plot in which a rate of change in the characteristic relative to the parameter has a magnitude that is greater than a first threshold; and
   a determiner configured to determine a next value of the parameter in response to the representation of the second subregion.

2. The apparatus of claim 1 wherein the simulator is configured to propagate the at least one state of the simulated system through time by randomly generating a value of the at least one state.

3. The apparatus of claim 1 wherein the simulator is configured to propagate the at least one state of the simulated system through time by generating a value of the at least one state in response to a probability distribution of possible values of the at least one state.

4. The apparatus of claim 1 wherein:
   the simulator is configured to simulate the system in response to a model of the system; and
   the model includes a model of a disease-transmission system.

5. The apparatus of claim 1 wherein:
   the simulator is configured to simulate the system in response to a model of the system; and
   the parameter includes a parameter of the model.

6. The apparatus of claim 1 wherein:
   the simulator is configured to propagate the at least one state through time in response to a model of an environment of the system; and
   the parameter includes a parameter of the model of the environment.

7. The apparatus of claim 1 wherein:
   the simulator is configured to propagate the at least one state through time in response to a value of another parameter; and
   wherein the simulator is configured to modify the value of the other parameter in response the value of the parameter.

8. The apparatus of claim 1 wherein:
   the simulator is configured to propagate the at least one state through time in response to a value of another parameter; and
   wherein the simulator is configured to determine the value of the other parameter in response the value of the parameter.

9. The apparatus of claim 1 wherein the representation of the region of the plot includes a representation of a region of a result surface.

10. The apparatus of claim 1 wherein:
    the representation of the region of the plot includes a representation of a region of a result surface; and the determiner is configured to determine the next value of the parameter to discover a feature of the representation of the region of the result surface.

11. The apparatus of claim 1 wherein:
the representation of the region of the plot includes a representation of a region of a result surface including a feature; and
the determiner is configured to determine the next value of the parameter to further define the feature of the representation of the region of the result surface.

12. The apparatus of claim 1 wherein:
the representation of the region of the plot includes a representation of a region of a result surface including a feature; and
the determiner is configured to determine the next value of the parameter in response to a portion of the region of the result surface remote from the feature.

13. The apparatus of claim 1 wherein:
the representation of the region of the plot includes a representation of a region of a result surface; and
the determiner is configured to determine the next value of the parameter to discover a slope of the representation of the region of the result surface.

14. The apparatus of claim 1 wherein the representation of the region of the plot includes a representation of a region of a result surface including a peak of the result surface.

15. The apparatus of claim 1 wherein:
the representation of the region of the plot includes a representation of a region of a result surface; and
the determiner is configured to determine the next value of the parameter to discover a peak of the representation of the region of the result surface.

16. The apparatus of claim 1 wherein the representation of the region of the plot includes a representation of a region of a result surface including a valley of the result surface.

17. The apparatus of claim 1 wherein:
the representation of the region of the plot includes a representation of a region of a result surface; and
the determiner is configured to determine the next value of the parameter to discover a valley of the representation of the region of the result surface.

18. The apparatus of claim 1, further including:
wherein the representation of the region of the plot includes a representation of a region of a result surface;
wherein the simulator is configured to propagate the at least one state through time for groups of simulation runs in response to a respective value of the parameter for each group;
a calculator configured to calculate a respective value of the characteristic of the other state of the simulated system for each group; and
wherein the generator is configured
to generate for each group a respective representation of a point having coordinates at least at the respective values of the parameter and the characteristic for the group, and
to generate the representation of the region of the result surface from the representations of the points.

19. The apparatus of claim 1, further including:
wherein the representation of the region of the plot includes a representation of a region of a result surface;
wherein the simulator is configured to propagate the at least one state through time for groups of simulation runs in response to a respective value of the parameter for each group, the simulations runs each having a same period;

a calculator configured to calculate a respective value of the characteristic of the other state of the simulated system for each group; and
wherein the generator is configured
to generate for each group a respective representation of a point having coordinates at least at the respective values of the parameter and the characteristic for the group, and
to generate the representation of the region of the result surface from the representations of the points.

20. The apparatus of claim 1, further including:
wherein the representation of the region of the plot includes a representation of a region of a result surface;
wherein the simulator is configured to propagate the at least one state through time for groups of simulation runs in response to a respective value of the parameter for each group;
a calculator configured to calculate a respective value of the characteristic of the other state of the simulated system for each group; and
wherein the generator is configured
to generate for each group a respective representation of a point having coordinates at least at the respective values of the parameter and the characteristic for the group, and
to generate the representation of the region of the result surface equal to a representation of a region of a surface, the region of the surface fitting the representations of the points.

21. The apparatus of claim 1, further including:
wherein the representation of the region of the plot includes a representation of a region of a result surface;
wherein the simulator is configured to propagate the at least one state through time for groups of simulation runs in response to a respective value of the parameter for each group;
a calculator configured to calculate a respective value of the characteristic of the other state for each group; and
wherein the generator is configured
to generate for each group a respective representation of a point having coordinates at least at the respective values of the parameter and the characteristic for the group, and
to generate the representation of the region of the result surface equal to a representation of a region of a surface, the region of the surface fitting the representations of the points such that at least one of the representations of the points is located off of the representation of the region of the surface.

22. The apparatus of claim 1, further including:
wherein the representation of the region of the plot includes a representation of a region of a result surface;
wherein the simulator is configured to propagate the at least one state through time for groups of simulation runs in response to a respective value of the parameter for each group;
a calculator configured to calculate a respective value of the characteristic of the other state for each group; and
wherein the generator is configured
to generate for each group a respective representation of a point having coordinates at least at the respective values of the parameter and the characteristic for the group, and
to generate the representation of the region of the result surface equal to a representation of a region of a surface, the region of the surface fitting the representations of the points such that at least one of the representations of the points is located on the representation of the region of the surface.

23. The apparatus of claim 1, further including:
wherein the representation of the region of the plot includes a representation of a region of a result surface;
wherein the simulator is configured to propagate the at least one state through time for groups of runs and for groups of subsequent runs in response to a respective value of the parameter for each group;
a calculator configured to calculate a respective value of the characteristic of the other state for each group; and
wherein the generator is configured
to generate for each group of runs and subsequent runs a respective representation of a point having coordinates at the respective values of the parameter and the characteristic for the group,
to generate the representation of the region of the result surface from the representations of the points generated for the groups of runs; and
to modify the representation of the region of the result surface from the representations of the points generated for the groups of subsequent runs.

24. The apparatus of claim 1 wherein the determiner is configured to determine the next value of the parameter by selecting the next value of the parameter equal to a coordinate of a representation of a point that lies within the representation of the region of the plot.

25. The apparatus of claim 1 wherein the determiner is configured to determine the next value of the parameter by selecting the next value of the parameter equal to a coordinate of a representation of a point that lies outside of the representation of the region of the plot.

26. The apparatus of claim 1 wherein:
the generator is configured to generate a representation of a level set; and
the determiner is configured to determine the next value of the parameter by selecting the next value of the parameter equal to a coordinate of a representation of a point that lies on a same side of the level set as the region.

27. The apparatus of claim 1 wherein the characteristic of the other state includes a probability that a value of the other state is within a particular range.

28. The apparatus of claim 1 wherein the characteristic of the other state includes an uncertainty that a value of the other state is within a particular range.

29. The apparatus of claim 1, further including:
wherein the simulator is configured
to propagate the at least one state through time for a number of simulation runs, and
to generate a respective value for the other state after each of the simulation runs; and
a calculator configured to calculate from the respective values of the other state a value of the characteristic of the other state.

30. The apparatus of claim 1, further including:
wherein the simulator is configured
to propagate the at least one state through time for a number of simulation runs, and
to generate a respective value for the other state after each of the simulation runs; and
a calculator configured
to calculate a Bayesian prior of the respective values of the other state, and
to calculate a value of the characteristic of the other state from the Bayesian prior.

31. The apparatus of claim 1, further including:
wherein the simulator is configured
to propagate the at least one state through time for a number of simulation runs, and
to generate a respective value for the other state after each of the simulation runs;
wherein the characteristic of the other state includes a probability that a value of the other state is within a particular range; and
a calculator configured to calculate from the respective values of the other state a value of the probability.

32. The apparatus of claim 1, further including:
wherein the simulator is configured
to propagate the at least one state through time for a number of simulation runs, and
to generate a respective value for the other state after each of the simulation runs;
wherein the characteristic of the other state includes a probability that a value of the other state is within a particular range; and
a calculator configured
to calculate a Bayesian prior of the respective values of the other state, and
to calculate a value of the probability from the Bayesian prior.

33. The apparatus of claim 1, further including:
wherein the simulator is configured
to propagate the at least one state through time for a number of simulation runs, and
to generate a respective value for the other state after each of the simulation runs;
wherein the characteristic of the other state includes an uncertainty that a value of the other state is within a particular range; and
a calculator configured to calculate from the respective values of the other state a value of the uncertainty.

34. The apparatus of claim 1, further including:
wherein the simulator is configured
to propagate the at least one state through time for a number of simulation runs, and
to generate a respective value for the other state after each of the simulation runs;
wherein the characteristic of the other state includes an uncertainty that a value of the other state is within a particular range; and
a calculator configured
to calculate a Bayesian prior of the respective values of the other state, and
to calculate a value of the uncertainty from the Bayesian prior.

35. The apparatus of claim 1, further including:
wherein the simulator is configured to simulate the system in response to a model of the system; and
the model of the system.

36. The apparatus of claim 1, further including:
wherein the representation of the region of the plot includes a representation of a region of the result surface;
wherein the simulator is configured to propagate the at least one state through time for groups of simulation runs in response to a respective value of the parameter for each group, at least two of the simulations runs each having a different period;

a calculator configured to calculate a respective value of the characteristic of the other state of the simulated system for each group; and wherein the generator is configured
to generate for each group a respective representation of a point having coordinates at least at the respective values of the parameter and the characteristic for the group, and
to generate the representation of the region of the result surface from the representations of the points.

37. The apparatus of claim 1 wherein:
the representation of the region of the plot includes a representation of a region of a result surface; and
wherein the representations of the first and second subregions of the plot include representations of first and second subregions of the result surface.

38. The apparatus of claim 1 wherein the second subregion spans at least a portion of the multi-value range of the characteristic.

39. The apparatus of claim 38 wherein the generator is configured to generate the representation of the region of the plot including a representation of a boundary subregion located between the first and second subregions.

40. The apparatus of claim 39 wherein the boundary subregion includes a level set.

41. The apparatus of claim 1 wherein the second subregion is outside of the multi-value range of the characteristic.

42. The apparatus of claim 41 wherein the generator is configured to generate the representation of the region of the plot including a representation of a boundary subregion located between the first and second subregions.

43. The apparatus of claim 42 wherein the boundary subregion includes a level set.

44. The apparatus of claim 1 wherein the second subregion is within the first subregion.

45. The apparatus of claim 1 wherein the second subregion is outside of the first subregion.

46. The apparatus of claim 1 wherein the second subregion overlaps the first subregion.

47. The apparatus of claim 1 where in the first subregion, a rate of change in the characteristic relative to the parameter has a magnitude that is less than the first threshold.

48. The apparatus of claim 1 wherein the determiner is configured to determine the next value of the parameter in further response to the representation of the first subregion of the plot.

49. The apparatus of claim 1 wherein the determiner is configured to determine another next value of the parameter in response to the representation of the first subregion of the plot.

50. An apparatus, comprising:
a simulator that includes one or more computing circuits and that is configured to simulate a system and to propagate at least one state of the simulated system through time in response to a value of a parameter;
a generator configured to generate
a representation of a region of a plot having dimensions that respectively correspond at least to the parameter and to a characteristic of another state of the simulated system, and
a representation of a level set; and
a determiner configured to determine a next value of the parameter in response to the representation of the region by selecting the next value of the parameter equal to a coordinate of a representation of a point that lies on a same side of the level set as the region.

51. An apparatus, comprising:
means for simulating a system and for propagating at least one first state of the simulated system through time in response to a value of a first parameter;
means for generating a representation of a region of a plot having dimensions that respectively correspond at least to the parameter and to a characteristic of a second state of the simulated system, the representation of the region including
a representation of a multi-point first subregion of the plot, the first subregion spanning a multi-value range of the characteristic, and
a representation of a second subregion of the plot in which a rate of change in the characteristic relative to the parameter has a magnitude that is greater than a threshold; and
means for determining a next value of the parameter in response to the representation of the second subregion of the plot.

52. The apparatus of claim 51 wherein the second subregion spans at least a portion of the multi-value range of the characteristic.

53. The apparatus of claim 51 wherein the means for generating a representation of a region of a plot includes means for generating the representation of the region of the plot including a representation of a boundary subregion located between the first and second subregions.

54. The apparatus of claim 53 wherein the boundary subregion includes a level set.

55. The apparatus of claim 53 wherein the means for determining include means for determining the next value of the parameter in further response to the representation of the first subregion of the plot.

56. The apparatus of claim 53 wherein the means for determining include means for determining another next value of the parameter in response to the representation of the first subregion of the plot.

57. A method, comprising:
simulating a system;
propagating at least one first state of the simulated system through time in response to a value of a first parameter;
generating a representation of a region of a plot having dimensions that respectively correspond at least to the parameter and to a characteristic of a second state of the simulated system;
searching the representation of the region of the plot for a representation of a multi-point first subregion of the plot spanning a multi-value range of the characteristic;
searching the representation of the region of the plot for a representation of a second subregion of the plot in which a rate of change in the characteristic relative to the parameter has a magnitude that is greater than a threshold; and
determining a next value of the parameter in response to the representation of one of the first and second subregions of the plot if the one of the first and second subregions exists.

58. The method of claim 57 wherein determining the next value includes determining the next value of the parameter in response to a representation of a portion of the region of the plot other than the first and second subregions if neither of the first and second subregions exists.

59. The method of claim 57 wherein if the second subregion of the plot exists, then the second subregion is outside of the multi-value range of the characteristic.

60. The method of claim 57 wherein generating the representation of the region of the plot includes generating a representation of a boundary subregion located between the first and second subregions if the first and second subregions exist.

61. The method of claim 57 wherein the boundary subregion includes a level set.

62. A non-transitory computer-readable medium storing instructions that, when executed by at least one computing apparatus, cause the at least one computing apparatus:
- to simulate a system;
- to propagate at least one first state of the simulated system through time in response to a value of a first parameter;
- to generate a representation of a region of a plot having dimensions that respectively correspond at least to the parameter and to a characteristic of a second state of the simulated system;
- to search the representation of the region of the plot for a representation of a multi-point first subregion of the plot spanning a multi-value range of the characteristic;
- to search the representation of the region of the plot for a representation of a second subregion of the plot in which a rate of change in the characteristic relative to the parameter has a magnitude that is greater than a threshold; and
- to determine a next value of the parameter in response to the representation of one of the first and second subregions of the plot if the one of the first and second subregions exists.

63. The non-transitory computer-readable medium of claim 62 wherein the instructions, when executed by the at least one computing apparatus, cause the at least one computing apparatus to determine the next value of the parameter in response to a representation of a portion of the region of the plot other than the first and second subregions if neither of the first and second subregions exists.

64. The non-transitory computer-readable medium of claim 62 wherein if the first and second subregions exist, then the second subregion is within the first subregion.

65. The non-transitory computer-readable medium of claim 62 wherein if the first and second subregions exist, then the second subregion is outside of the first subregion.

66. The non-transitory computer-readable medium of claim 62 wherein if the first and second subregions exist, then the second subregion overlaps the first subregion.

67. The non-transitory computer-readable medium of claim 62 wherein if the first subregion exists, then in the first subregion a rate of change in the characteristic relative to the parameter has a magnitude that is less than the threshold.

68. The non-transitory computer-readable medium of claim 62 wherein the instructions, when executed by the at least one computing apparatus, cause the at least one computing apparatus to determine the next value of the parameter in response to the representations of the first and second subregions of the plot if the first and second subregions exist.

* * * * *